United States Patent
Sun et al.

(10) Patent No.: US 10,441,565 B2
(45) Date of Patent: Oct. 15, 2019

(54) CONJUGATE OF MEMANTINE AND ARCTIGENIN, AND COMPOSITION AND USE THEREOF

(71) Applicant: Shenzhen Qingyaqirui Bio-Tech Co., Ltd., Shenzhen, Guangdong (CN)

(72) Inventors: Haifeng Sun, Guangdong (CN); Zhiyuan Zhu, Guangdong (CN); Jun Liu, Guangdong (CN); Wei Yan, Guangdong (CN); Ding Zhang, Guangdong (CN); Jing Yang, Guangdong (CN)

(73) Assignee: SHENZHEN QINGYAQIRUI BIO-TECH CO., LTD., Shenzhen (CN)

( * ) Notice: Subject to any disclaimer, the term of this patent is extended or adjusted under 35 U.S.C. 154(b) by 0 days.

(21) Appl. No.: 15/756,342

(22) PCT Filed: Aug. 31, 2015

(86) PCT No.: PCT/CN2015/088585
§ 371 (c)(1),
(2) Date: Feb. 28, 2018

(87) PCT Pub. No.: WO2017/035733
PCT Pub. Date: Mar. 9, 2017

(65) Prior Publication Data
US 2018/0280344 A1  Oct. 4, 2018

(51) Int. Cl.
| | | |
|---|---|---|
| *A61K 31/13* | (2006.01) |
| *A61K 31/365* | (2006.01) |
| *A61K 47/54* | (2017.01) |
| *A61P 25/28* | (2006.01) |
| *A61K 45/06* | (2006.01) |
| *A61K 47/55* | (2017.01) |
| *A61K 31/445* | (2006.01) |
| *A61K 31/473* | (2006.01) |
| *A61K 31/4748* | (2006.01) |

(52) U.S. Cl.
CPC ............ *A61K 31/365* (2013.01); *A61K 31/13* (2013.01); *A61K 31/445* (2013.01); *A61K 31/473* (2013.01); *A61K 31/4748* (2013.01); *A61K 45/06* (2013.01); *A61K 47/542* (2017.08); *A61K 47/55* (2017.08); *A61P 25/28* (2018.01)

(58) Field of Classification Search
None
See application file for complete search history.

(56) References Cited

FOREIGN PATENT DOCUMENTS

| | | | |
|---|---|---|---|
| CN | 101348461 A | 1/2009 | |
| CN | 103467417 A | 12/2013 | |
| WO | WO-2012019113 A2 * | 2/2012 | ........... A61K 31/353 |

OTHER PUBLICATIONS

Wu et al., Toxicology, vol. 236, pp. 1-6 (Year: 2007).*

* cited by examiner

*Primary Examiner* — Zinna Northington Davis
(74) *Attorney, Agent, or Firm* — Arent Fox LLP

(57) ABSTRACT

Provided are a conjugate of memantine and arctigenin, and a pharmaceutical composition comprising the conjugate. The conjugate can treat diseases associated with Aβ or Tau protein pathways, such as Alzheimer's disease or Parkinson's disease.

14 Claims, 2 Drawing Sheets genetic control group: 2U*H29.3

AD test group P35*H29.3

CONJUGATE OF MEMANTINE AND ARCTIGENIN, AND COMPOSITION AND USE THEREOF

FIELD OF THE INVENTION

The present invention is in the fields of medicinal chemistry and treatment of diseases. Specifically, the present invention relates to a conjugate of memantine and arctigenin, a pharmaceutical composition comprising the same, and use thereof in the treatment of a disease associated with the Amyloid beta (Aβ) or Tau protein pathway, especially use thereof in the treatment of a neurodegenerative disease, such as Alzheimer's disease or Parkinson's disease, etc.

BACKGROUND OF THE INVENTION

Alzheimer's disease (AD) is a highly age-related, progressive central nervous system degenerative disease. Its early clinical manifestations are memory and cognition, executive dysfunction such as recent memory loss, aphasia, apraxia, agnosia, etc. and abnormal personality changes etc.; mid-term clinical manifestations are personality and behavior changes such as irritability, panic, sleep disorder, hallucination and the like; and late clinical manifestations are lack of logical thinking, bedridden, incompetence of taking care of oneself and the like.

Statistics show that there are currently about 30 million AD patients worldwide, and with the aging of the world's population, the number of AD patients worldwide will exceed 100 million by the year of 2050. AD patients will not be able to live independently in the middle and late stages, and need to be taken care of by medical staff. According to statistics, the US currently spends more than 300 billion dollars annually on AD care (US, Alzheimer's Disease Association). According to the latest statistics released by China's National Bureau of Statistics, by the end of 2014, the number of the elderly aged 60 and above in China had reached 212.42 million, accounting for 15.5% of the total population, and the population aged 65 and above was 137.55 million, accounting for 10.1% of the total population. At present, the number of AD patients in China has exceeded 8 million. With the aging of the population in China, the number of AD patients will increase dramatically. It is estimated that by 2050, the number of AD patients in China will reach nearly 30 million, and AD thus has become a significant burden on society and families of China.

AD patients have two important histopathological features: in the brain tissues associated with learning and memory such as cerebral cortex, hippocampus, forebrain basal ganglia and thalamus, there are a large number of senile plaques (SP) formed by the aggregation of Aβ, and neurofibrillary tangles resulted from hyperphosphorylation of Tau proteins. Studies show that when Aβ increases in the brain of AD patients, Aβ protein aggregates to form highly neurotoxic oligomers, resulting in changes of oxidative stress, inflammation and hyperphosphorylation of Tau proteins in the brain, and inducing neuronal death ultimately. Therefore, Aβ, as an initiation factor in the pathological changes of AD, plays a crucial role in the pathological process of AD patients.

Aβ, no matter in the brains of familial AD patients or non-familial scattered AD patients, has increased significantly before the onset of AD symptoms, indicating that Aβ is an initiation factor that leads to pathological changes of AD. In addition, it is also found in the AD model mice with high expression of Aβ that the increase of Aβ is earlier than the appearance of memory impairment; meanwhile, when BACE1 (the rate-limiting enzyme in the production of Aβ) is knocked out in the AD model mice, memory impairment and neuronal apoptosis are significantly reversed with notable decease of Aβ. As such, Aβ has become an important target for new anti-AD therapeutics, and AD model mice with high expression of Aβ have also become a well-accepted model for evaluating the efficacy of such anti-AD therapeutics. APP/PS1 double transgenic AD model mice (B6C3 transgenic mice, APPswe, PS1dE9) have high expression of chimeric mouse/human Swedish mutation APP (Mo/HuAPP695swe) and presenilin-1 that is humanized with the deletion of the 9$^{th}$ exon (PS1-dE9). Both of the two gene mutations are recognized as the main pathogenic mutations in familial AD. Such APP/PS1 transgenic AD model mice begin to develop Aβ deposits at about 6 months, and memory impairment occurs at about 7 months. As such, APP/PS1 transgenic mice become model mice suitable for the efficacy evaluation in the development of anti-AD therapeutics.

Memantine is currently used in clinic for the treatment of AD. However, memantine can only ameliorate the symptoms of AD without blocking its pathological progression (Areosa S A et al., Memantine for dementia. (2005) Cochrane Database Syst Rev. (3): CD003154). It is urgently needed to develop a drug which can ameliorate the symptoms of AD while blocking its pathological progression.

It is reported in Chinese patent application No. CN 103467417 A that arctigenin has the effect of inhibiting the production of Aβ by activating phosphorylation of AMPK and reducing the phosphorylation of AKT, inhibiting the mTOR pathway which results in increased autophagy, thereby increasing the clearance of Aβ, and thus has a therapeutic effect on AD. However, according to further investigations of the present inventors, arctigenin has poor oral bioavailability, and thus cannot be used for oral administration. Developing arctigenin derivatives with improved oral bioavailability would benefit in improving patient compliance.

SUMMARY OF THE INVENTION

In one aspect, the present invention provides a conjugate, comprising memantine and arctigenin,

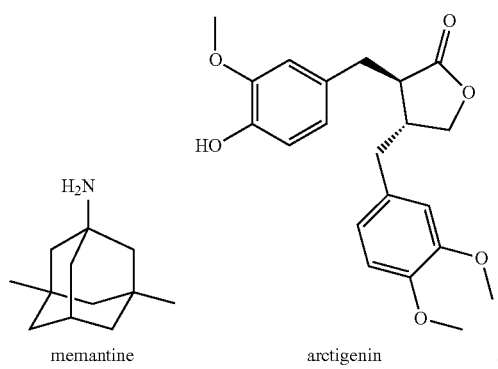

The conjugate can be a compound of general formula (I), or a pharmaceutically acceptable salt, stereoisomer, polymorph, solvate or prodrug thereof, wherein linker 1 is as defined below,

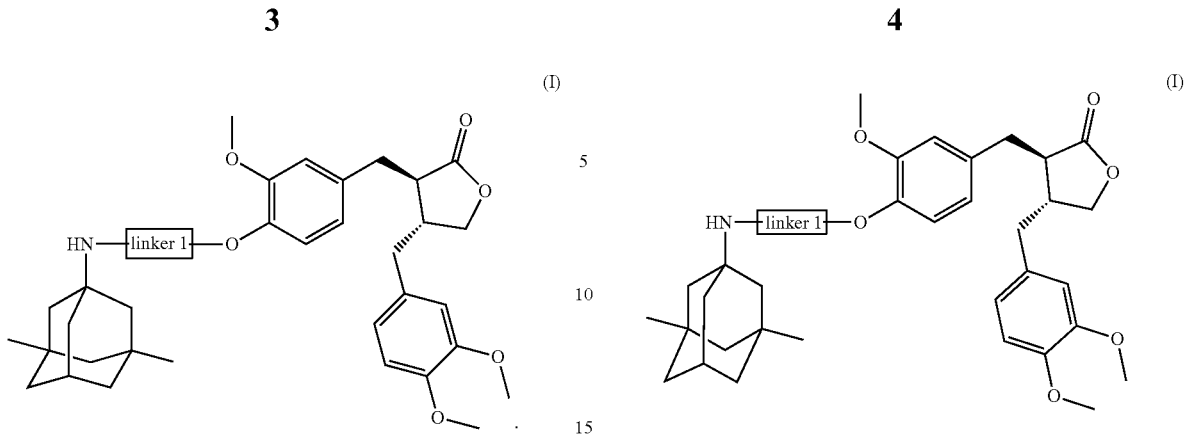

(I)

The conjugate can be used for the treatment of a disease associated with the Aβ or Tau protein pathway.

In another aspect, the present invention provides a pharmaceutical composition, comprising the conjugate of the present invention and one or more pharmaceutically acceptable carriers, and optionally further comprising one or more additional agents for the treatment of a disease associated with the Aβ or Tau protein pathway.

In still another aspect, the present invention provides a method for treating a disease associated with the Aβ or Tau protein pathway, comprising administering to a subject in need thereof a therapeutically effective amount of the conjugate or the pharmaceutical composition of the present invention, and optionally comprising administering to the subject in need thereof an additional agent for the treatment of a disease associated with the Aβ or Tau protein pathway.

In still another aspect, the present invention provides use of the conjugate of the present invention in the manufacture of a medicament for the treatment of a disease associated with the Aβ or Tau protein pathway.

DETAILED DESCRIPTION OF THE INVENTION

Conjugate

Figure 1:
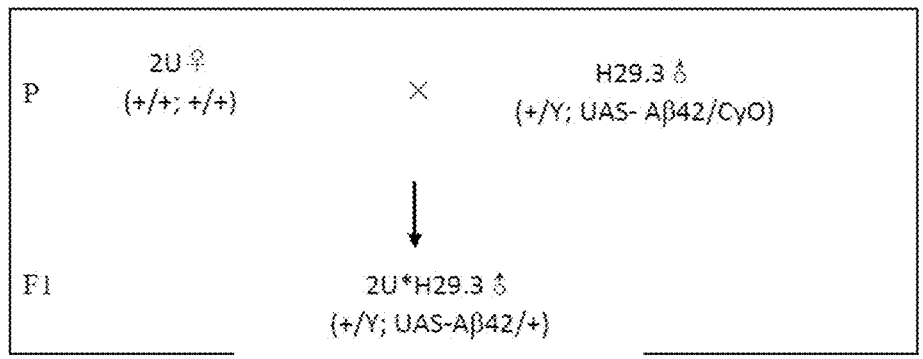
FIG. 1 is a genetic illustration of the *drosophila*.
Figure 1:
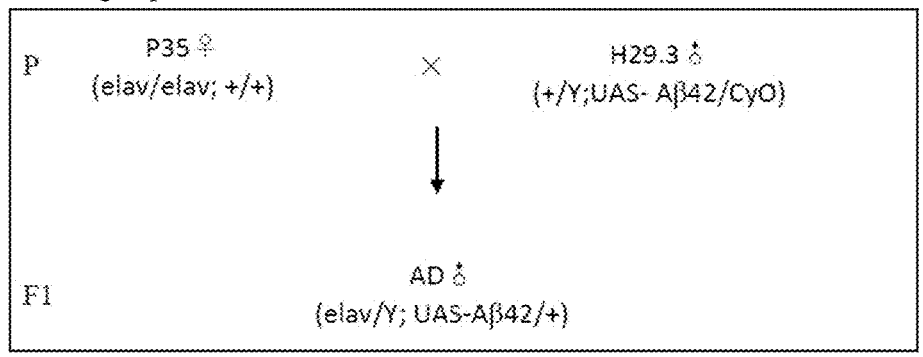

In one aspect, the present invention provides a conjugate, comprising memantine and arctigenin.

In one embodiment, the conjugate of the present invention is a compound of general formula (I), or a pharmaceutically acceptable salt, stereoisomer, polymorph, solvate or prodrug thereof:

wherein:

Linker 1 is selected from the group consisting of —C(O)—, —C(O)$L_1$C(O)—, —C(O)O$L_1$C(O)—, —C(O)O$L_1$OC(O)—, —C(O)O$Q_1L_2Q_2$-, —C(O)$Q_1L_2Q_2$N($R_1$)C(O)—, —C(O)$Q_1L_2Q_2$OC(O)—, —C(O)$Q_1L_2Q_2$C(O)—, —C(O)O$Q_1L_2Q_2$OC(O)—, —C(O)O$Q_1L_1Q_2$N($R_1$)C(O)—, —C(O)O$Q_1L_2Q_2$N($R_1$)C(O)— and —C(O)O$Q_1L_2Q_2$C(O)—;

$L_1$ is a direct bond, or is selected from the group consisting of —O—, —S—, —N$R_2$—, substituted or unsubstituted C1-C6 straight or branched alkylene, substituted or unsubstituted C2-C6 straight or branched alkenylene, substituted or unsubstituted C2-C6 straight or branched alkynylene, substituted or unsubstituted C3-C10 cycloalkylene, substituted or unsubstituted C3-C10 non-aromatic heterocyclylene, substituted or unsubstituted C6-C14 arylene, substituted or unsubstituted C6-C14 heteroarylene, and substituted or unsubstituted C6-C20 aralkylene;

$L_2$ is a direct bond, or is selected from the group consisting of —N$R_2$—, —O—, —C(O)—, —N($R_3$)C(O)—, —C(O)N($R_3$)—, —C(O)O—, —OC(O)—, —N($R_3$)$Q_3$O—, —N($R_3$)C(O)$Q_3$O—, —N($R_3$)C(O)$Q_3$C(O)—, —N($R_3$)C(O)$Q_3$N($R_3$)—, —N($R_3$)C(O)$Q_3$C(O)N($R_3$)—, —N($R_3$)C(O)$Q_3$N($R_3$)C(O)—, —N($R_3$)C(O)$Q_3$C(O)O—, —N($R_3$)C(O)$Q_3$OC(O)—, —C(O)N($R_3$)$Q_3$C(O)N($R_3$)—, —C(O)N($R_3$)$Q_3$C(O)O—, —C(O)N($R_3$)$Q_3$N($R_3$)C(O)—, —C(O)N($R_3$)$Q_3$OC(O)—, —N($R_3$)$Q_3$C(O)N($R_3$)—, —N($R_3$)$Q_3$C(O)O—, —N($R_3$)$Q_3$N($R_3$)C(O)—, —N($R_3$)$Q_3$OC(O)—, —O$Q_3$N($R_3$)—, —O$Q_3$C(O)N($R_3$)—, —O$Q_3$C(O)O—, —O$Q_3$N($R_3$)C(O)—, —O$Q_3$OC(O)—, —OC(O)$Q_3$-, —OC(O)$Q_3$C(O)N($R_3$)—, —OC(O)$Q_3$C(O)O—, —OC(O)$Q_3$N($R_3$)—, —OC(O)$Q_3$N($R_3$)C(O)—, —OC(O)$Q_3$N($R_3$)$L_1$O—, —OC(O)$Q_3$OC(O)—, —C(O)O$Q_3$-, —C(O)O$Q_3$O—, —C(O)O$Q_3$C(O)N($R_3$)—, —C(O)O$Q_3$C(O)O—, —C(O)O$Q_3$N($R_3$)C(O)— or —C(O)O$Q_3$OC(O)—;

$Q_1$, $Q_2$ and $Q_3$ are each independently selected from the group consisting of substituted or unsubstituted C1-C6 straight or branched alkylene, substituted or unsubstituted C3-C10 cycloalkylene, substituted or unsubstituted C2-C6 straight or branched alkenylene, substituted or unsubstituted C2-C6 straight or branched alkynylene, substituted or unsubstituted C3-C10 non-aromatic heterocyclylene, substituted or unsubstituted C6-C14 arylene, substituted or unsubstituted C6-C14 heteroarylene, and substituted or unsubstituted C6-C20 aralkylene; and $R_1$, $R_2$ and $R_3$ are each independently selected from the group consisting of H and C1-C6 alkyl.

In a preferred embodiment, Linker 1 is selected from the group consisting of —C(O)—, —C(O)L$_1$C(O)—, —C(O)OL$_1$C(O)—, —C(O)OL$_1$OC(O)—, —C(O)OQ$_1$L$_2$Q$_2$-, —C(O)OQ$_1$L$_2$Q$_2$OC(O)—, —C(O)OQ$_1$L$_1$Q$_2$N(R$_1$)C(O)—, —C(O)OQ$_1$L$_2$Q$_2$N(R$_1$)C(O)— and —C(O)OQ$_1$L$_2$Q$_2$C(O)—.

In a preferred embodiment, $L_1$ is a direct bond, or is selected from the group consisting of methylene, ethylene, propylene, pyrrolidinylene, piperidinylene, piperazinylene, phenylene, benzylidene or pyridylene, and the group is optionally substituted with one or more substituents selected from the group consisting of cyano, amino, halogen or C1-C6 alkyl.

In a preferred embodiment, $L_2$ is a direct bond, or is selected from the group consisting of —NR$_2$—, —C(O)—, —C(O)N(R$_3$)—, —C(O)O—, —OC(O)—, —N(R$_3$)Q$_3$O—, —N(R$_3$)C(O)Q$_3$C(O)—, —N(R$_3$)C(O)Q$_3$C(O)N(R$_3$)—, —OQ$_3$N(R$_3$)—, —OC(O)Q$_3$-, —OC(O)Q$_3$C(O)O—, —OC(O)Q$_3$N(R$_3$)—, —OC(O)Q$_3$N(R$_3$)L$_1$O—, —C(O)OQ$_3$-, —C(O)OQ$_3$O—.

In a preferred embodiment, $Q_1$, $Q_2$ and $Q_3$ are each independently selected from the group consisting of methylene, ethylene, propylene, cyclohexylene, pyrrolidinylene, piperidinylene, piperazinylene, phenylene, benzylidene or pyridylene, and the group is optionally substituted with one or more substituents selected from the group consisting of cyano, amino, halogen or C1-C6 alkyl.

In a preferred embodiment, $R_1$, $R_2$ and $R_3$ are each independently selected from the group consisting of H and C1-C4 alkyl, e.g., methyl.

The present invention encompasses the conjugate of general formula (I) obtained by any combination of the preferred groups.

In a preferred embodiment, the conjugate of the present invention is a compound of general formula (II), or a pharmaceutically acceptable salt, stereoisomer, polymorph, solvate or prodrug thereof:

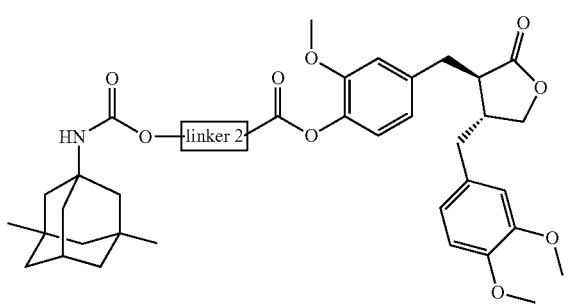

(II)

wherein:

Linker 2 is selected from the group consisting of -L$_1$-, -L$_1$O—, -Q$_1$L$_1$Q$_2$N(R$_1$)—, -Q$_1$L$_2$Q$_2$N(R$_1$)—, -Q$_1$L$_2$Q$_2$O— or -Q$_1$L$_2$Q$_2$-;

$L_1$ is selected from the group consisting of substituted or unsubstituted C1-C6 straight or branched alkylene, substituted or unsubstituted C2-C6 straight or branched alkenylene, substituted or unsubstituted C2-C6 straight or branched alkynylene, substituted or unsubstituted C3-C10 cycloalkylene, substituted or unsubstituted C3-C10 non-aromatic heterocyclylene, substituted or unsubstituted C6-C14 arylene, substituted or unsubstituted C6-C14 heteroarylene, and substituted or unsubstituted C6-C20 aralkylene; and $L_2$, $Q_1$, $Q_2$, $Q_3$, $R_1$, $R_2$ and $R_3$ are as defined above for general formula (I).

In another preferred embodiment, the conjugate of the present invention is a conjugate of general formula (III), or a pharmaceutically acceptable salt, stereoisomer, polymorph, solvate or prodrug thereof:

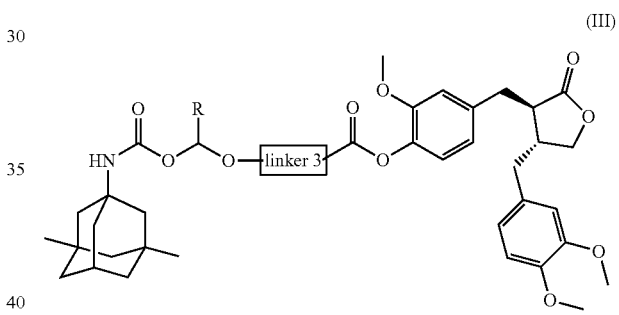

(III)

wherein:

Linker 3 is a direct bond, or is selected from the group consisting of —C(O)Q$_3$N(R$_3$)Q$_2$-, —C(O)Q$_3$N(R$_3$)Q$_2$N(R$_1$)—, —C(O)Q$_2$O—, —C(O)Q$_2$N(R$_1$)—, —C(O)Q$_3$N(R$_3$)L$_1$OQ$_2$N(R$_1$)— and —C(O)Q$_3$Q$_2$N(R$_1$)—;

$L_1$, $Q_2$, $Q_3$, $R_1$ and $R_3$ are as defined above for general formula (II); and R is selected from the group consisting of H or C1-C6 alkyl.

In another preferred embodiment, when any two groups of $L_1$, $Q_1$, $Q_2$ or $Q_3$ are linked directly, the two groups are not of the same type. In other words, when any two groups of $L_1$, $Q_1$, $Q_2$ or $Q_3$ are linked directly, the two groups are not simultaneously alkylene, cycloalkylene, alkenylene, alkynylene, non-aromatic heterocyclylene, arylene, heteroarylene or aralkylene.

In another embodiment, the conjugate of the present invention is selected from, but is not limited to those listed in the table below:

| No. | Conjugate Structure |
|---|---|
| A01 | 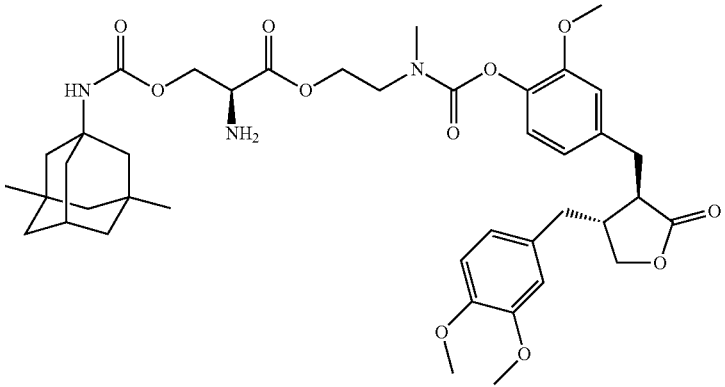 [SMILES: COc1ccc(C[C@H]2COC(=O)[C@@H]2Cc2ccc(OC(=O)N(C)CCOC(=O)[C@@H](N)COC(=O)NC34CC5CC(C)(CC(C)(C5)C3)C4)c(OC)c2)cc1OC] |
| A02 | 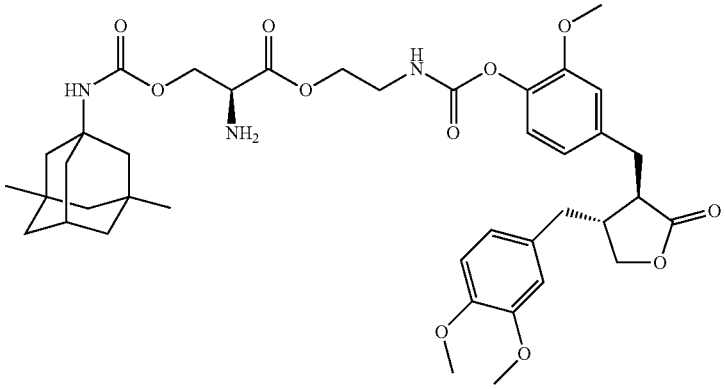 [SMILES: COc1ccc(C[C@H]2COC(=O)[C@@H]2Cc2ccc(OC(=O)NCCOC(=O)[C@@H](N)COC(=O)NC34CC5CC(C)(CC(C)(C5)C3)C4)c(OC)c2)cc1OC] |
| A03 | 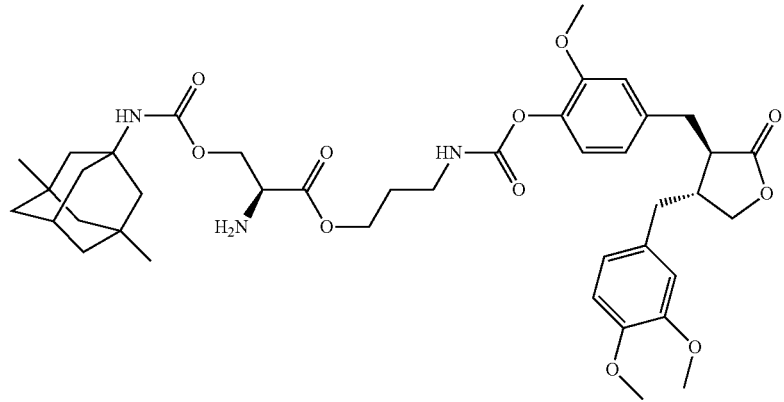 [SMILES: COc1ccc(C[C@H]2COC(=O)[C@@H]2Cc2ccc(OC(=O)NCCCOC(=O)[C@@H](N)COC(=O)NC34CC5CC(C)(CC(C)(C5)C3)C4)c(OC)c2)cc1OC] |
| A04 | 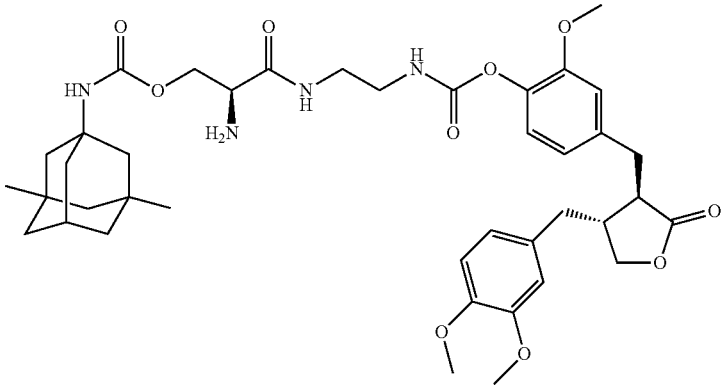 [SMILES: COc1ccc(C[C@H]2COC(=O)[C@@H]2Cc2ccc(OC(=O)NCCNC(=O)[C@@H](N)COC(=O)NC34CC5CC(C)(CC(C)(C5)C3)C4)c(OC)c2)cc1OC] |

| No. | Conjugate Structure |
|-----|---------------------|
| A05 | 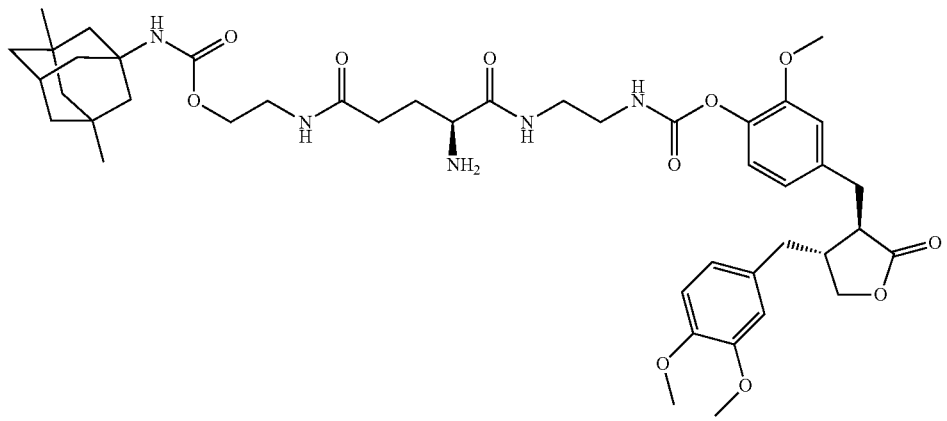 [SMILES: COc1ccc(C[C@H]2COC(=O)[C@@H]2Cc2ccc(OC(=O)NCCNC(=O)[C@@H](N)CCC(=O)NCCOC(=O)NC34CC5CC(C)(CC(C)(C5)C3)C4)c(OC)c2)cc1OC] |
| A06 | 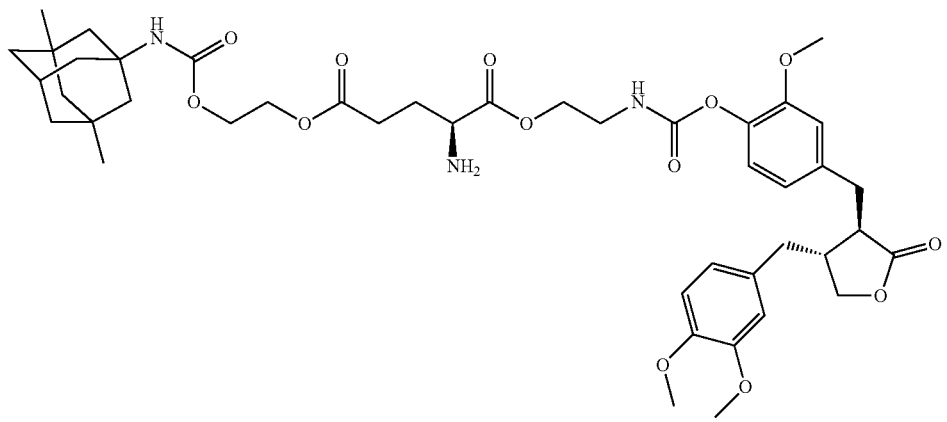 [SMILES: COc1ccc(C[C@H]2COC(=O)[C@@H]2Cc2ccc(OC(=O)NCCOC(=O)[C@@H](N)CCC(=O)OCCOC(=O)NC34CC5CC(C)(CC(C)(C5)C3)C4)c(OC)c2)cc1OC] |
| A07 | 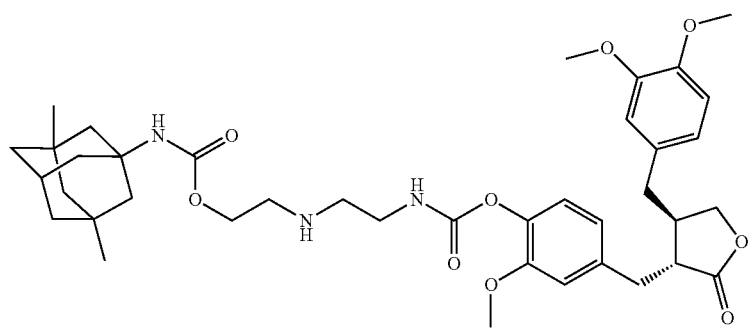 [SMILES: COc1ccc(C[C@H]2COC(=O)[C@@H]2Cc2ccc(OC(=O)NCCNCCOC(=O)NC34CC5CC(C)(CC(C)(C5)C3)C4)c(OC)c2)cc1OC] |
| A08 | 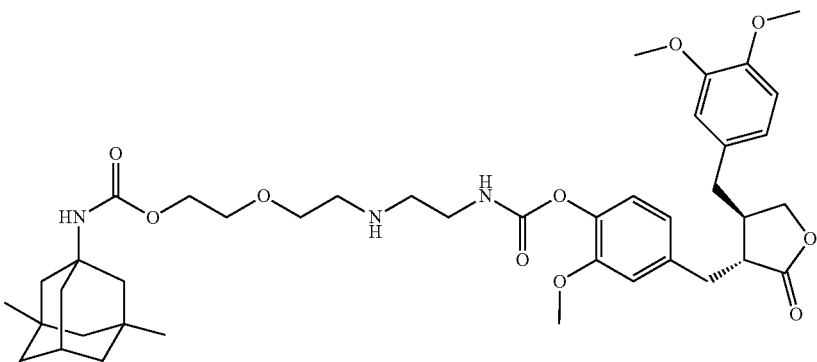 [SMILES: COc1ccc(C[C@H]2COC(=O)[C@@H]2Cc2ccc(OC(=O)NCCNCCOCCOC(=O)NC34CC5CC(C)(CC(C)(C5)C3)C4)c(OC)c2)cc1OC] |

| No. | Conjugate Structure |
|---|---|
| A09 | 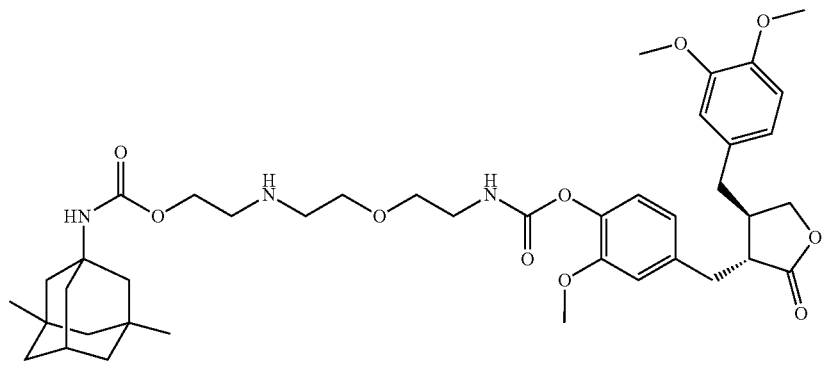 [SMILES: COc1ccc(C[C@H]2COC(=O)[C@@H]2Cc2ccc(OC(=O)NCCOCCNCCOC(=O)NC34CC5CC(C)(CC(C)(C5)C3)C4)c(OC)c2)cc1OC] |
| A10 | 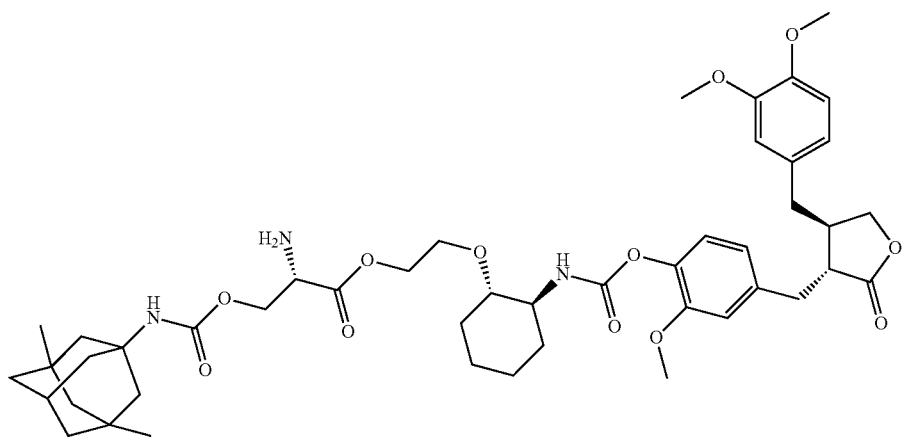 [SMILES: COc1ccc(C[C@H]2COC(=O)[C@@H]2Cc2ccc(OC(=O)N[C@H]3CCCC[C@@H]3OCCOC(=O)[C@@H](N)COC(=O)NC34CC5CC(C)(CC(C)(C5)C3)C4)c(OC)c2)cc1OC] |
| A11 | 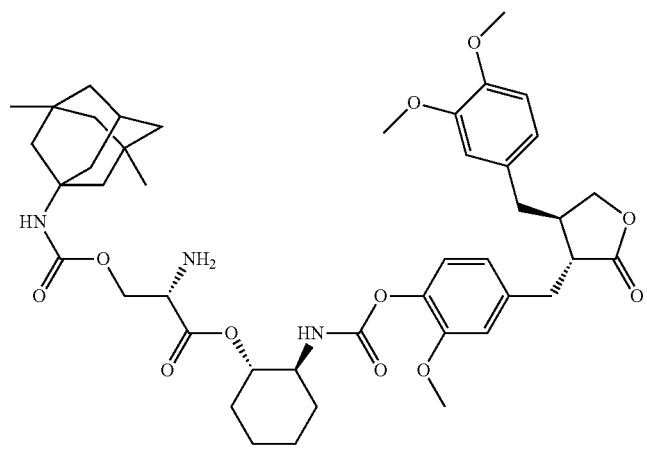 [SMILES: COc1ccc(C[C@H]2COC(=O)[C@@H]2Cc2ccc(OC(=O)N[C@H]3CCCC[C@@H]3OC(=O)[C@@H](N)COC(=O)NC34CC5CC(C)(CC(C)(C5)C3)C4)c(OC)c2)cc1OC] |
| A12 | 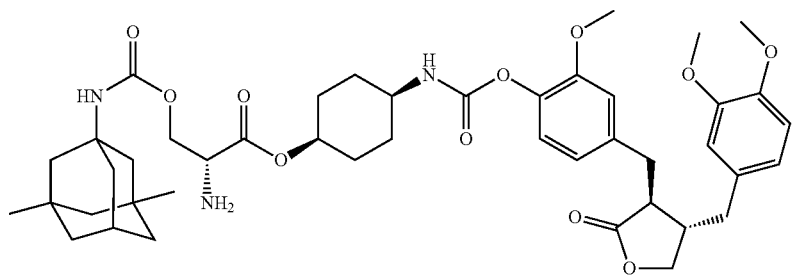 [SMILES: COc1ccc(C[C@@H]2COC(=O)[C@H]2Cc2ccc(OC(=O)N[C@H]3CC[C@@H](OC(=O)[C@H](N)COC(=O)NC45CC6CC(C)(CC(C)(C6)C4)C5)CC3)c(OC)c2)cc1OC] |

| No. | Conjugate Structure |
|---|---|
| A13 | 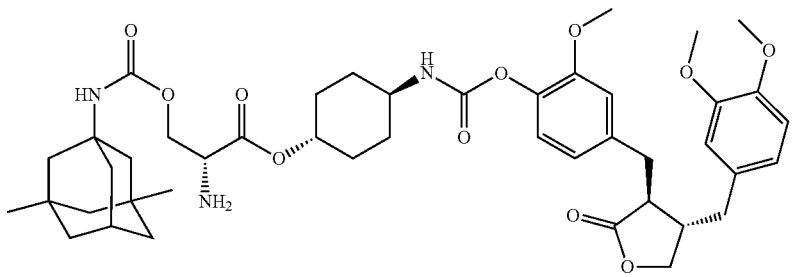 [SMILES: COc1ccc(C[C@@H]2COC(=O)[C@H]2Cc2ccc(OC(=O)N[C@H]3CC[C@H](OC(=O)[C@H](N)COC(=O)NC45CC6CC(C)(CC(C)(C6)C4)C5)CC3)c(OC)c2)cc1OC] |
| A14 | 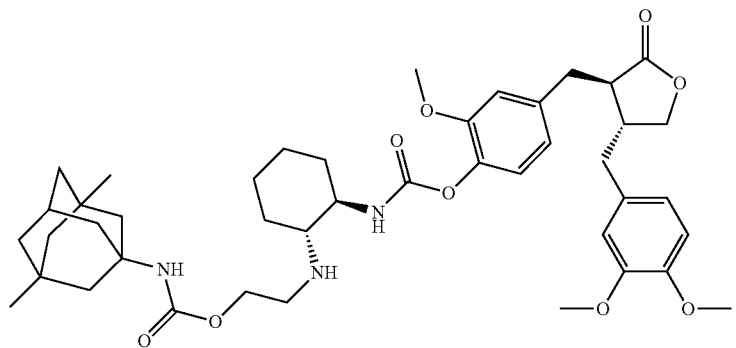 |
| A15 | 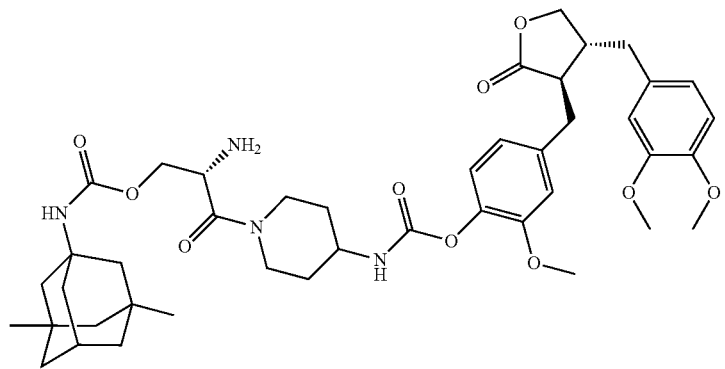 [SMILES: COc1ccc(C[C@H]2COC(=O)[C@@H]2Cc2ccc(OC(=O)NC3CCN(C(=O)[C@@H](N)COC(=O)NC45CC6CC(C)(CC(C)(C6)C4)C5)CC3)c(OC)c2)cc1OC] |
| A16 | 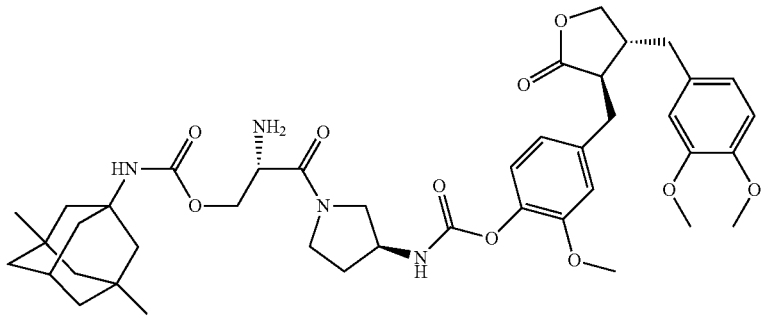 [SMILES: COc1ccc(C[C@H]2COC(=O)[C@@H]2Cc2ccc(OC(=O)N[C@H]3CCN(C(=O)[C@@H](N)COC(=O)NC45CC6CC(C)(CC(C)(C6)C4)C5)C3)c(OC)c2)cc1OC] |

| No. | Conjugate Structure |
|---|---|
| A17 | 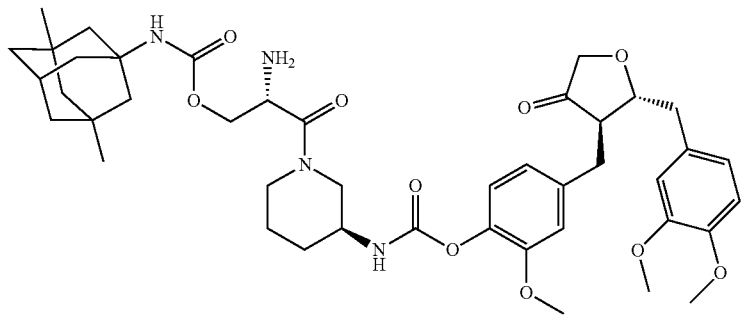 [SMILES: COc1ccc(C[C@H]2OCC(=O)[C@@H]2Cc2ccc(OC(=O)N[C@H]3CCCN(C(=O)[C@@H](N)COC(=O)NC45CC6CC(C)(CC(C)(C6)C4)C5)C3)c(OC)c2)cc1OC] |
| A18 | 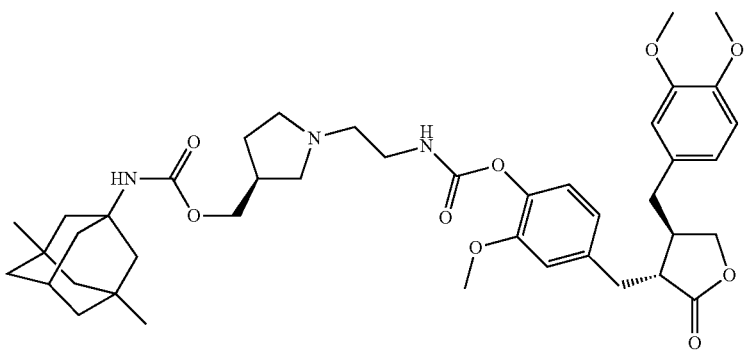 [SMILES: COc1ccc(C[C@H]2COC(=O)[C@@H]2Cc2ccc(OC(=O)NCCN3CC[C@H](COC(=O)NC45CC6CC(C)(CC(C)(C6)C4)C5)C3)c(OC)c2)cc1OC] |
| A19 | 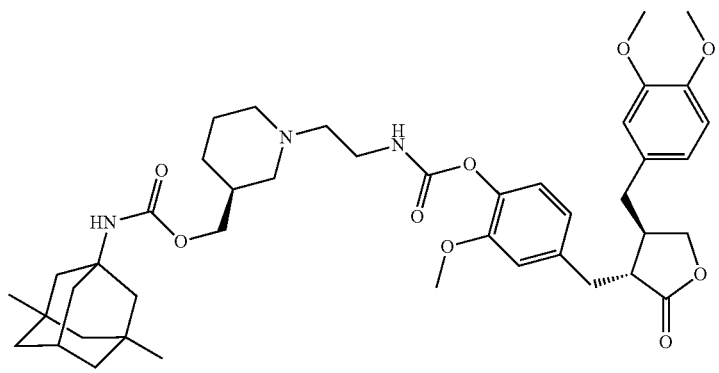 [SMILES: COc1ccc(C[C@H]2COC(=O)[C@@H]2Cc2ccc(OC(=O)NCCN3CCC[C@H](COC(=O)NC45CC6CC(C)(CC(C)(C6)C4)C5)C3)c(OC)c2)cc1OC] |
| A20 | 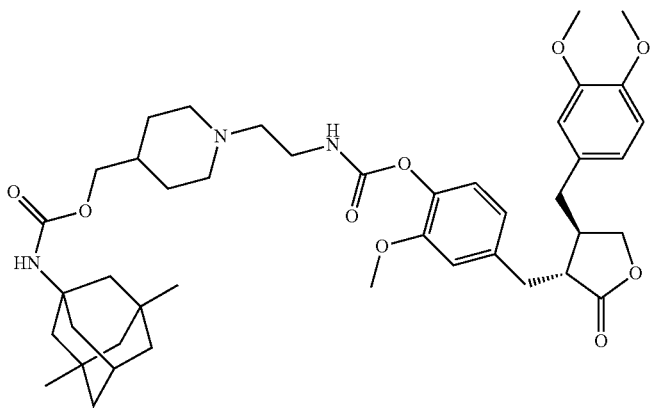 [SMILES: COc1ccc(C[C@H]2COC(=O)[C@@H]2Cc2ccc(OC(=O)NCCN3CCC(COC(=O)NC45CC6CC(C)(CC(C)(C6)C4)C5)CC3)c(OC)c2)cc1OC] |

| No. | Conjugate Structure |
|---|---|
| A21 | 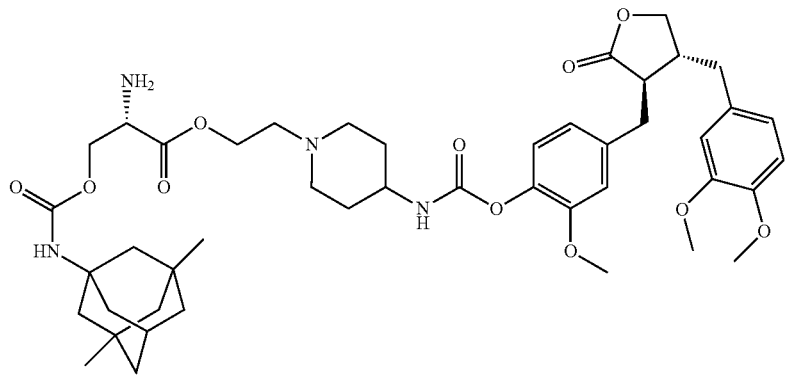 [SMILES: COc1ccc(C[C@H]2COC(=O)[C@@H]2Cc2ccc(OC(=O)NC3CCN(CCOC(=O)[C@@H](N)COC(=O)NC45CC6CC(C)(CC(C)(C6)C4)C5)CC3)c(OC)c2)cc1OC] |
| A22 | 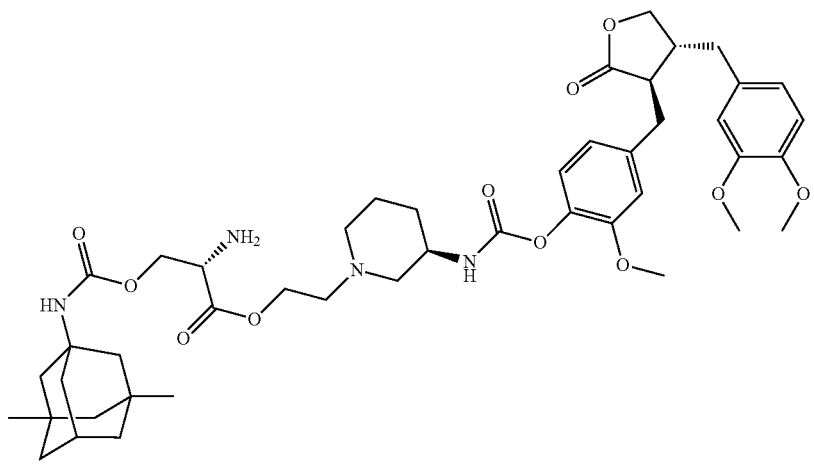 [SMILES: COc1ccc(C[C@H]2COC(=O)[C@@H]2Cc2ccc(OC(=O)N[C@@H]3CCCN(CCOC(=O)[C@@H](N)COC(=O)NC45CC6CC(C)(CC(C)(C6)C4)C5)C3)c(OC)c2)cc1OC] |
| A23 | 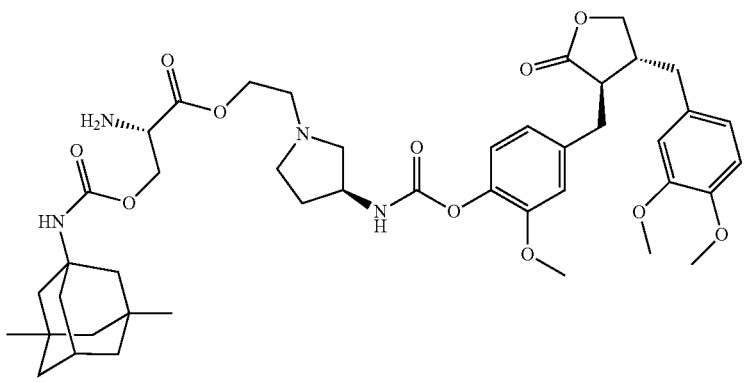 [SMILES: COc1ccc(C[C@H]2COC(=O)[C@@H]2Cc2ccc(OC(=O)N[C@H]3CCN(CCOC(=O)[C@@H](N)COC(=O)NC45CC6CC(C)(CC(C)(C6)C4)C5)C3)c(OC)c2)cc1OC] |
| A24 | 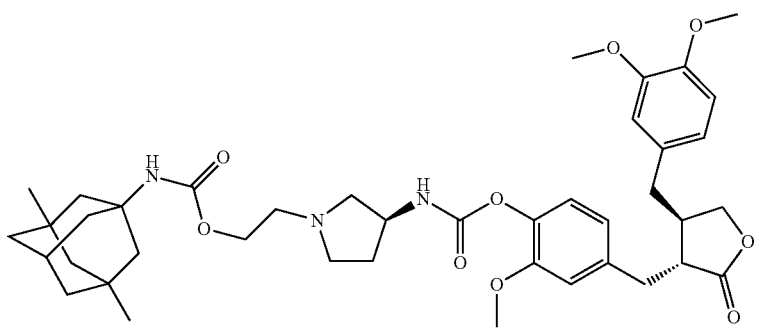 [SMILES: COc1ccc(C[C@H]2COC(=O)[C@@H]2Cc2ccc(OC(=O)N[C@H]3CCN(CCOC(=O)NC45CC6CC(C)(CC(C)(C6)C4)C5)C3)c(OC)c2)cc1OC] |

| No. | Conjugate Structure |
|---|---|
| A25 | 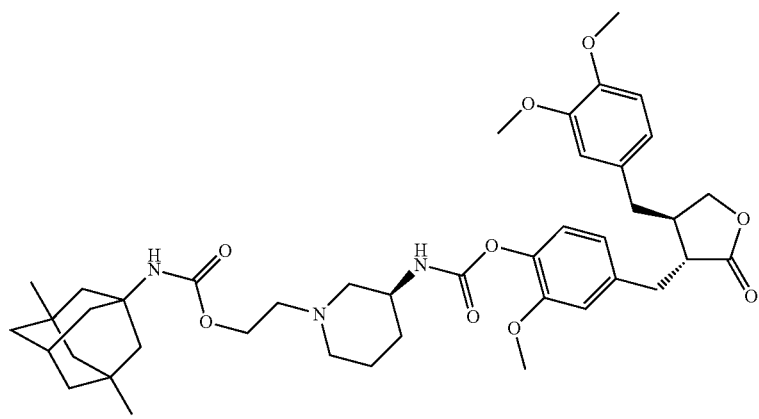 [SMILES: COc1ccc(C[C@H]2COC(=O)[C@@H]2Cc2ccc(OC(=O)N[C@H]3CCCN(CCOC(=O)NC45CC6CC(C)(CC(C)(C6)C4)C5)C3)c(OC)c2)cc1OC] |
| A26 | 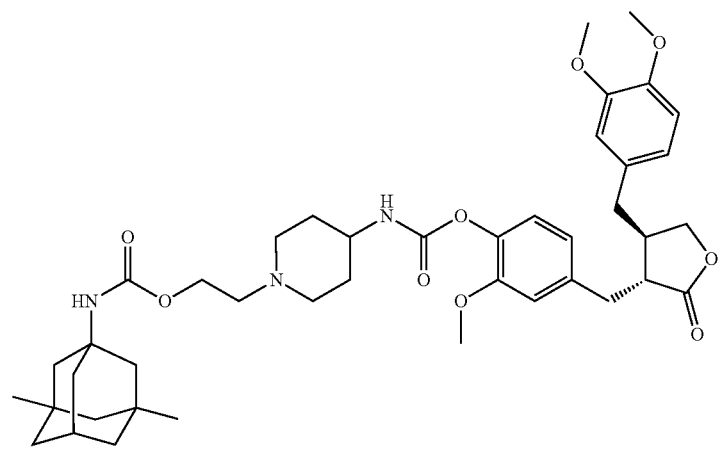 [SMILES: COc1ccc(C[C@H]2COC(=O)[C@@H]2Cc2ccc(OC(=O)NC3CCN(CCOC(=O)NC45CC6CC(C)(CC(C)(C6)C4)C5)CC3)c(OC)c2)cc1OC] |
| A27 | 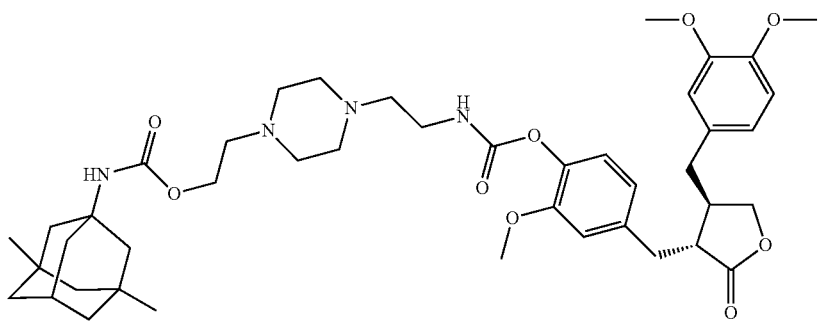 [SMILES: COc1ccc(C[C@H]2COC(=O)[C@@H]2Cc2ccc(OC(=O)NCCN3CCN(CCOC(=O)NC45CC6CC(C)(CC(C)(C6)C4)C5)CC3)c(OC)c2)cc1OC] |
| A28 | 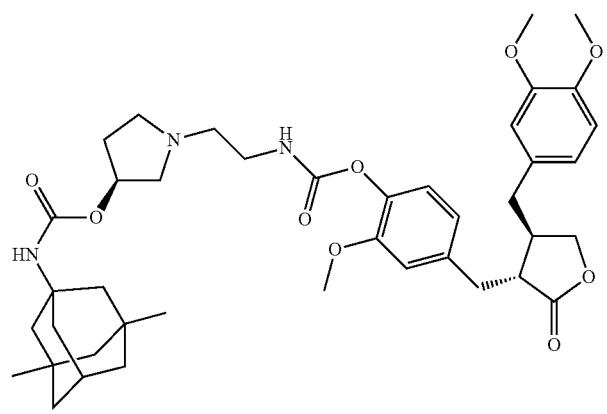 [SMILES: COc1ccc(C[C@H]2COC(=O)[C@@H]2Cc2ccc(OC(=O)NCCN3CC[C@H](OC(=O)NC45CC6CC(C)(CC(C)(C6)C4)C5)C3)c(OC)c2)cc1OC] |

| No. | Conjugate Structure |
|---|---|
| A29 | 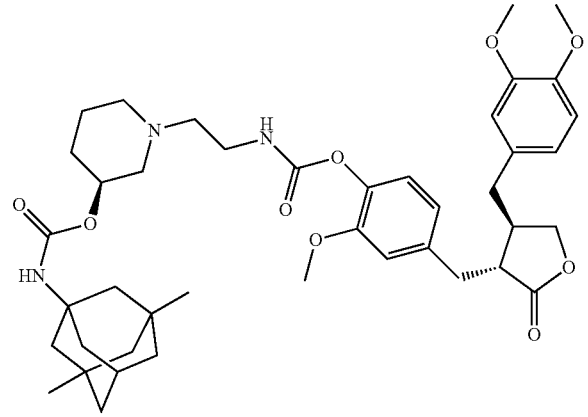 [SMILES: COc1ccc(C[C@H]2COC(=O)[C@@H]2Cc2ccc(OC(=O)NCCN3CCC[C@H](OC(=O)NC45CC6CC(C)(CC(C)(C6)C4)C5)C3)c(OC)c2)cc1OC] |
| A30 | 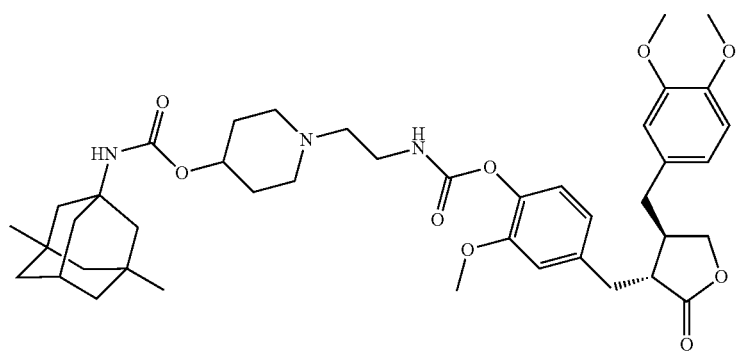 [SMILES: COc1ccc(C[C@H]2COC(=O)[C@@H]2Cc2ccc(OC(=O)NCCN3CCC(OC(=O)NC45CC6CC(C)(CC(C)(C6)C4)C5)CC3)c(OC)c2)cc1OC] |
| A31 | 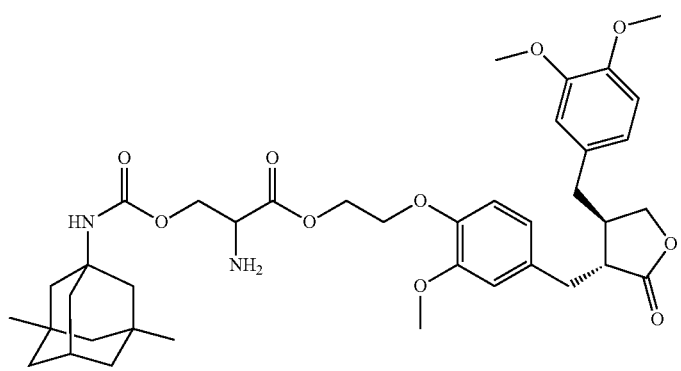 [SMILES: COc1ccc(C[C@H]2COC(=O)[C@@H]2Cc2ccc(OCCOC(=O)C(N)COC(=O)NC34CC5CC(C)(CC(C)(C5)C3)C4)c(OC)c2)cc1OC] |
| A32 | 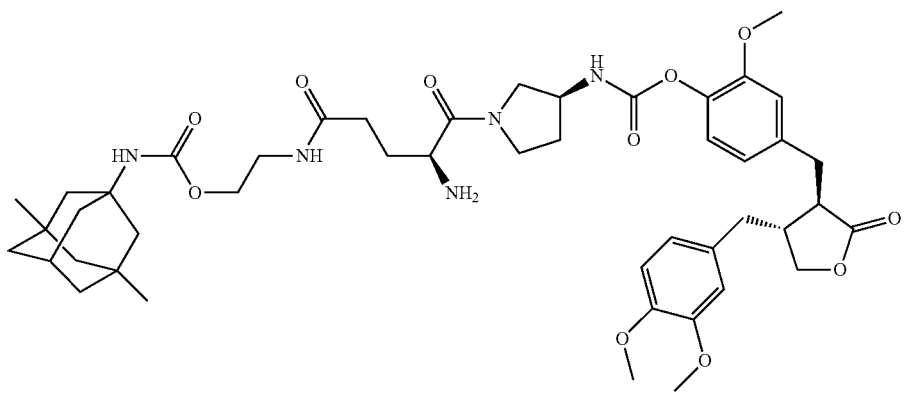 [SMILES: COc1ccc(C[C@H]2COC(=O)[C@@H]2Cc2ccc(OC(=O)N[C@H]3CCN(C(=O)[C@@H](N)CCC(=O)NCCOC(=O)NC45CC6CC(C)(CC(C)(C6)C4)C5)C3)c(OC)c2)cc1OC] |

| No. | Conjugate Structure |
|---|---|
| A33 | 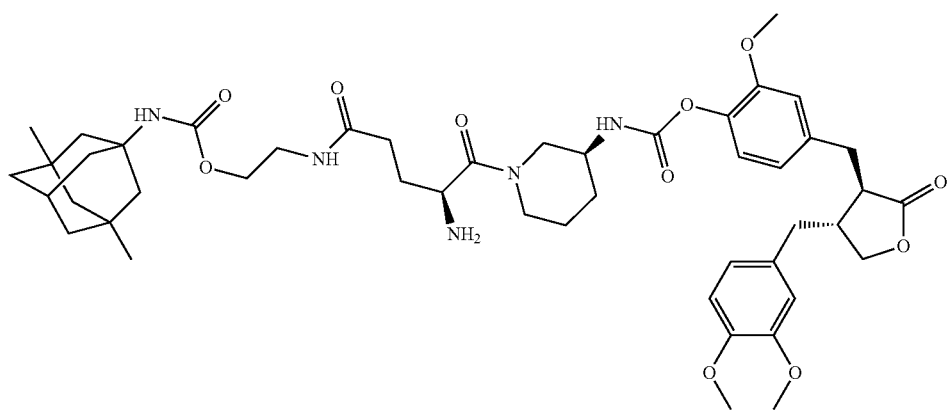 [SMILES: COc1ccc(C[C@H]2COC(=O)[C@@H]2Cc2ccc(OC(=O)N[C@H]3CCCN(C(=O)[C@@H](N)CCC(=O)NCCOC(=O)NC45CC6CC(C)(CC(C)(C6)C4)C5)C3)c(OC)c2)cc1OC] |
| A34 | 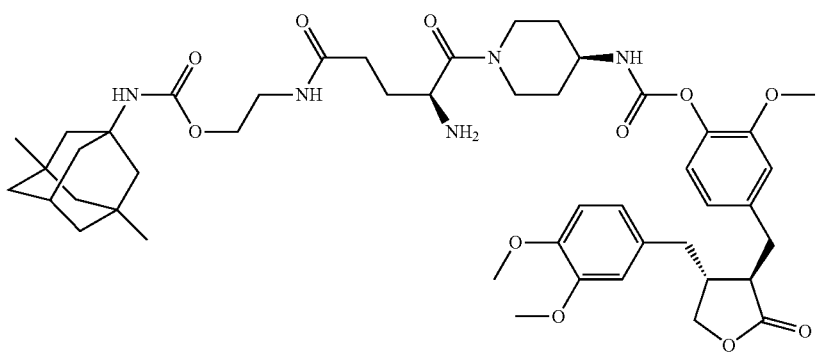 |
| A35 | 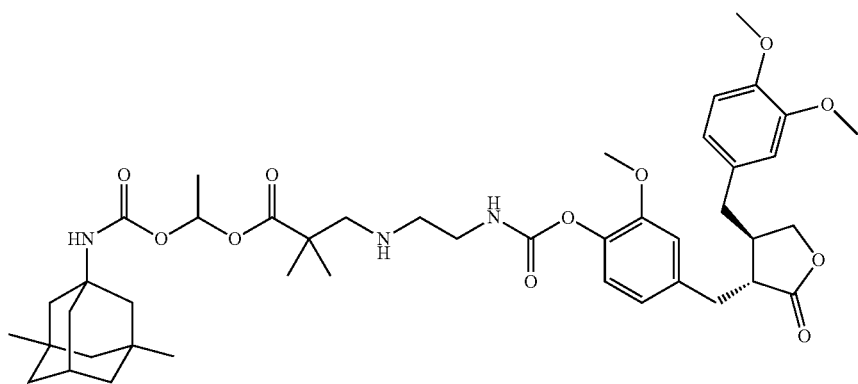 |
| A36 | 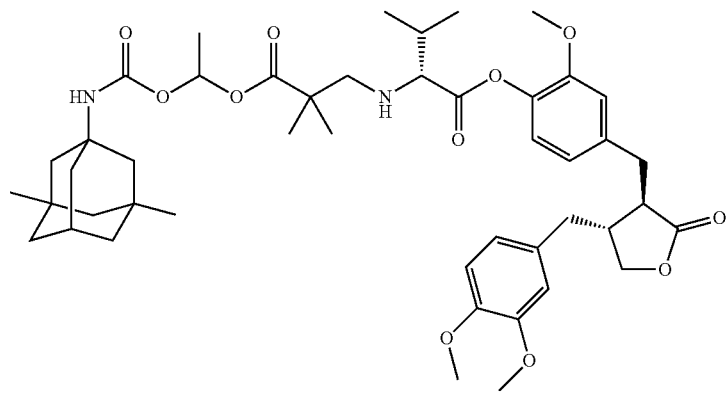 [SMILES: COc1ccc(C[C@H]2COC(=O)[C@@H]2Cc2ccc(OC(=O)[C@H](NCC(C)(C)C(=O)OC(C)OC(=O)NC34CC5CC(C)(CC(C)(C5)C3)C4)C(C)C)c(OC)c2)cc1OC] |

| No. | Conjugate Structure |
|---|---|
| A37 | 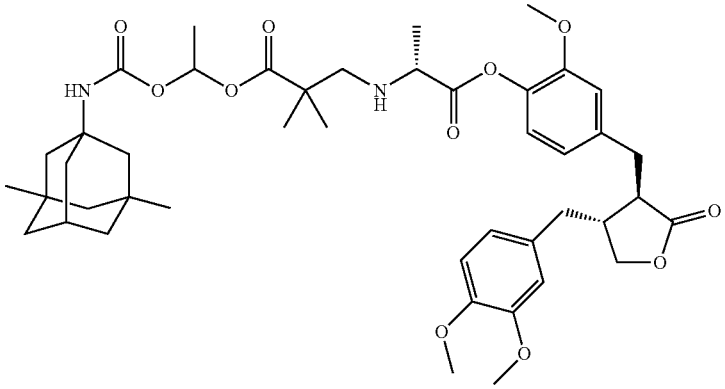 [SMILES: COc1ccc(C[C@H]2COC(=O)[C@@H]2Cc2ccc(OC(=O)[C@@H](C)NCC(C)(C)C(=O)OC(C)OC(=O)NC34CC5CC(C)(CC(C)(C5)C3)C4)c(OC)c2)cc1OC] |
| A38 | 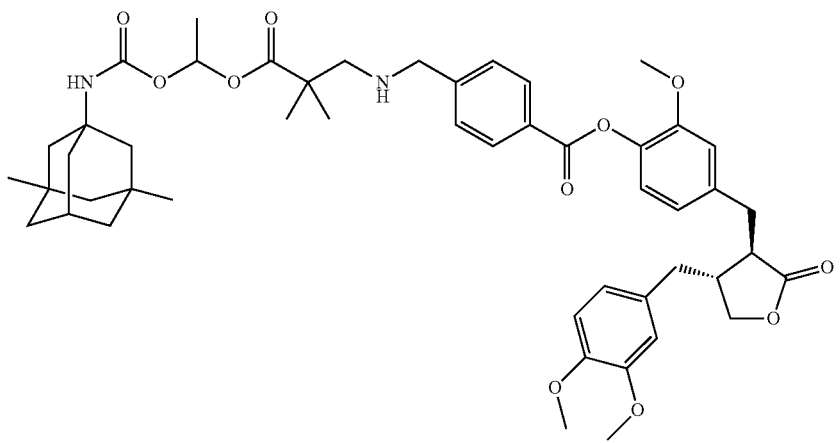 [SMILES: COc1ccc(C[C@H]2COC(=O)[C@@H]2Cc2ccc(OC(=O)c3ccc(CNCC(C)(C)C(=O)OC(C)OC(=O)NC45CC6CC(C)(CC(C)(C6)C4)C5)cc3)c(OC)c2)cc1OC] |
| A39 | 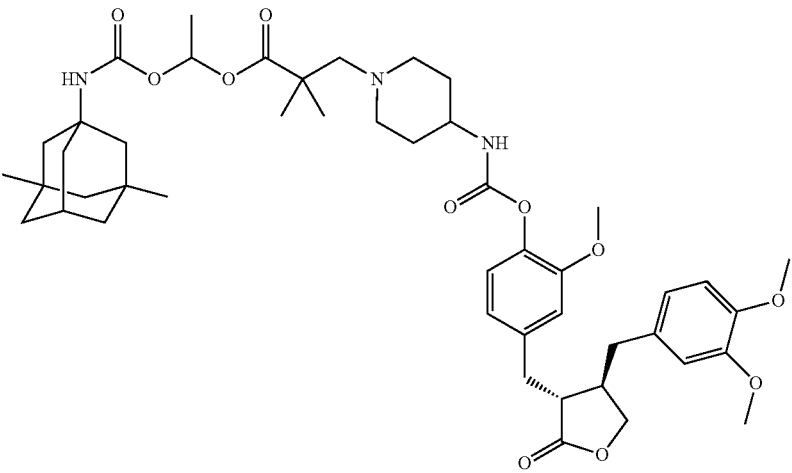 |
| A40 | 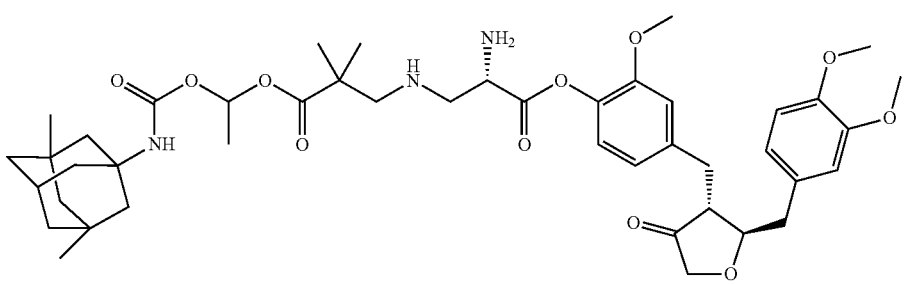 |

-continued
| No. | Conjugate Structure |
|---|---|
| A41 | 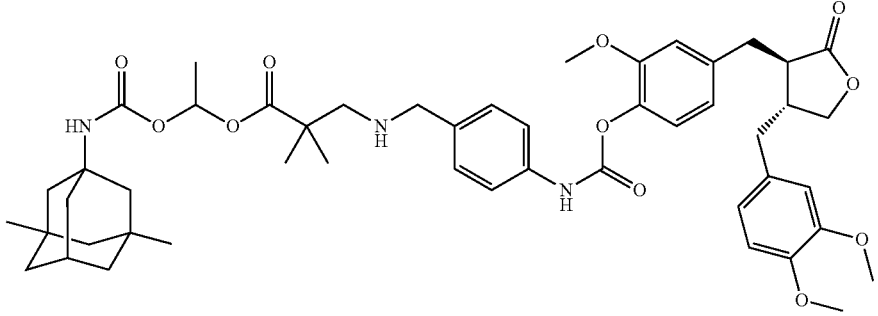 |
| A42 | 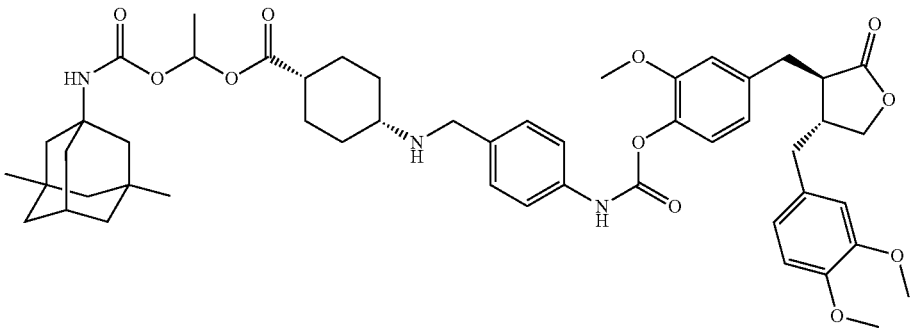 |
| A43 | 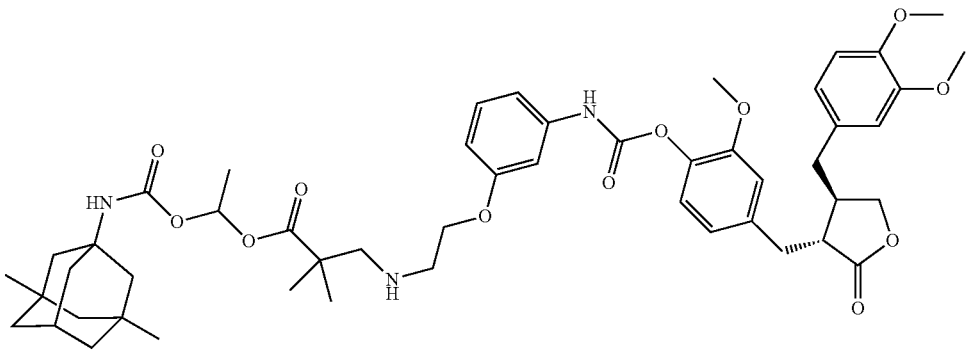 |
| A44 | 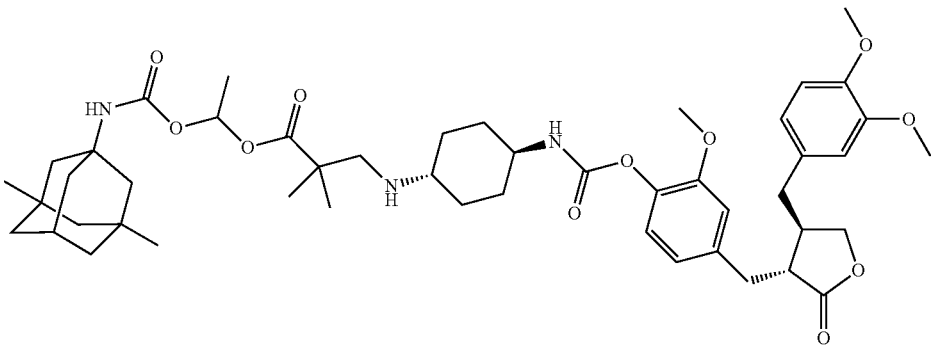 |

| No. | Conjugate Structure |
|---|---|
| A45 | 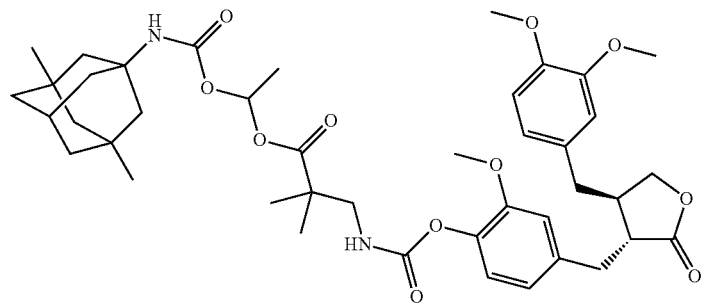 [SMILES: COc1ccc(C[C@H]2COC(=O)[C@@H]2Cc2ccc(OC(=O)NCC(C)(C)C(=O)OC(C)OC(=O)NC34CC5CC(C)(CC(C)(C5)C3)C4)c(OC)c2)cc1OC] |
| A46 | 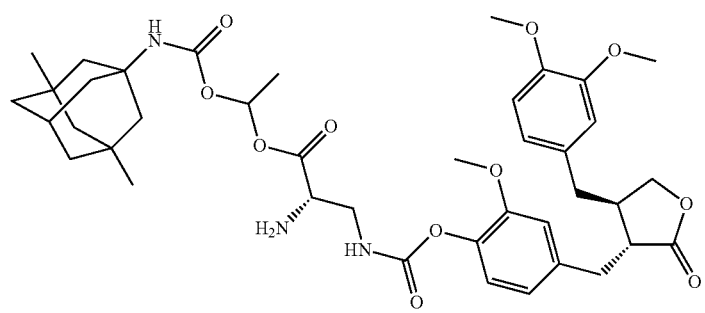 [SMILES: COc1ccc(C[C@H]2COC(=O)[C@@H]2Cc2ccc(OC(=O)NC[C@H](N)C(=O)OC(C)OC(=O)NC34CC5CC(C)(CC(C)(C5)C3)C4)c(OC)c2)cc1OC] |
| A47 | 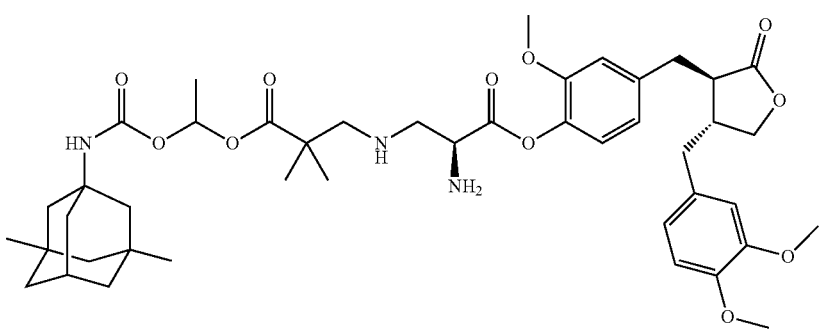 |
| A48 | 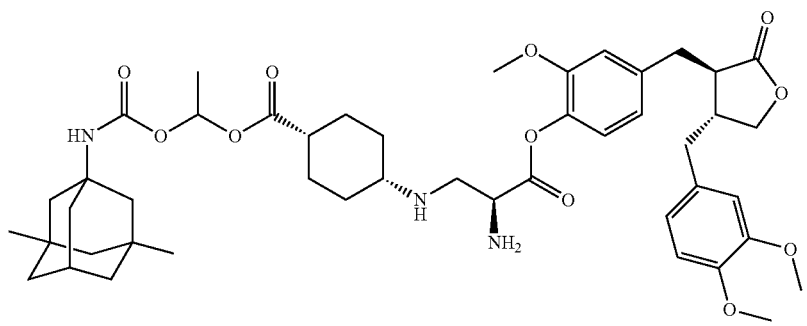 |

| No. | Conjugate Structure |
|---|---|
| A49 | 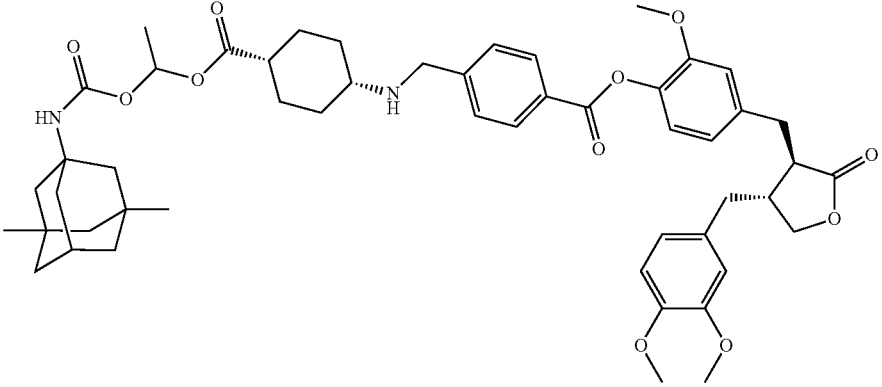 [SMILES: COc1ccc(C[C@H]2COC(=O)[C@@H]2Cc2ccc(OC(=O)c3ccc(CN[C@H]4CC[C@@H](C(=O)OC(C)OC(=O)NC56CC7CC(C)(CC(C)(C7)C5)C6)CC4)cc3)c(OC)c2)cc1OC] |
| A50 | 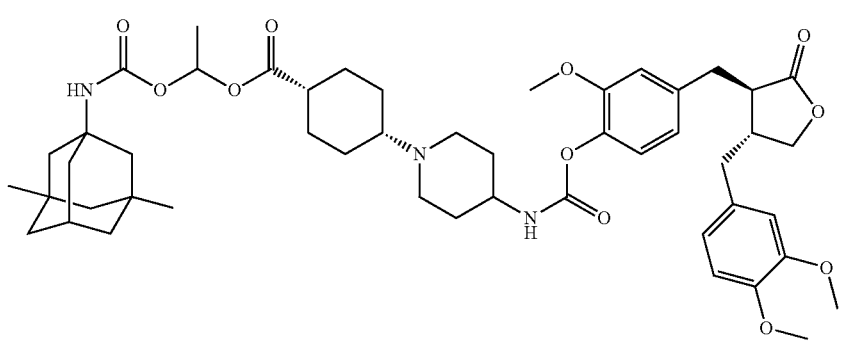 |
| A51 | 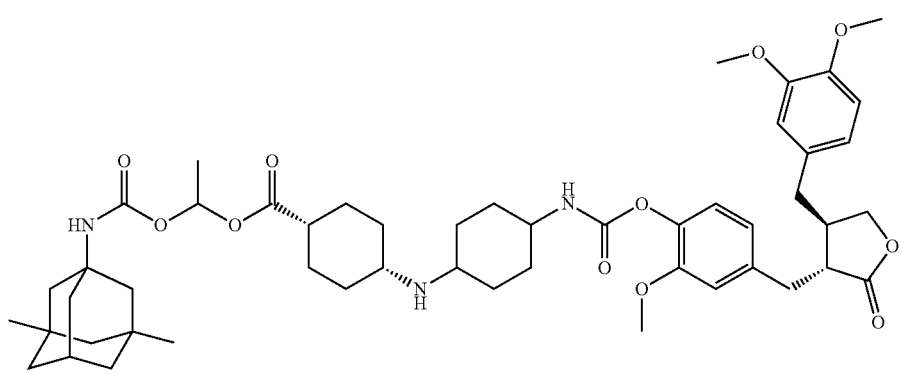 [SMILES: COc1ccc(C[C@H]2COC(=O)[C@@H]2Cc2ccc(OC(=O)NC3CCC(N[C@H]4CC[C@@H](C(=O)OC(C)OC(=O)NC56CC7CC(C)(CC(C)(C7)C5)C6)CC4)CC3)c(OC)c2)cc1OC] |
| A52 | 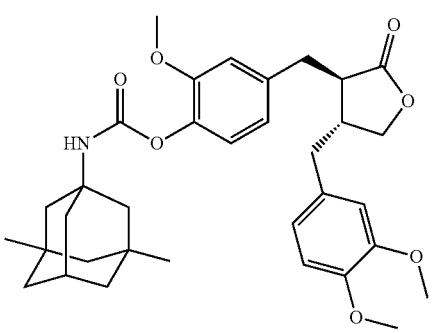 |

| No. | Conjugate Structure |
|---|---|
| A53 | |
| A54 | |
| A55 | |

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

The term "alkyl" preferably refers to a saturated monovalent hydrocarbon radical having 1, 2, 3, 4, 5 or 6 carbon atoms, such as methyl, ethyl, propyl, butyl, isopropyl, isobutyl, sec-b utyl, or tert-butyl.

The term "alkylene" preferably refers to a saturated divalent hydrocarbon radical having 1, 2, 3, 4, 5 or 6 carbon atoms, e.g., methylene, ethylene, propylene or butylene.

The term "alkenylene" preferably refers to a divalent hydrocarbon radical comprising one or more double bonds, such as ethenylene, propenylene or allylene.

The term "alkynylene" preferably refers to a divalent hydrocarbon radical comprising one or more triple bonds, such as ethynylene or propynylene.

The term "cycloalkylene" preferably refers to a saturated, divalent, mono-, or bicyclic hydrocarbon ring, such as cyclopropylene, cyclobutylene, cyclopentylene, cyclohexylene, cycloheptylene, cyclooctylene, cyclononylene, cyclodecylene, or decalinene ring.

The term "heterocyclylene" preferably refers to a saturated or unsaturated, divalent ring system containing one or more heteroatoms selected from the group consisting of $C(=O)$, O, S, $S(=O)$, $S(=O)_2$, $NR^a$, wherein $R^a$ represents a hydrogen atom or C1-C6 alkyl or alkylene; it being possible for said heterocyclylene to be attached to the rest of the molecule via any of the ring atoms, or via any one of the ring atoms and a carbon atom of $R^a$ (when $R^a$ represents C1-C6 alkyl). The heterocyclylene is for example, but is not limited to a 4-membered ring, such as azetidinylene, oxetanylene, or a 5-membered ring, such as tetrahydrofuranylene, dioxolinylene, pyrrolidinylene, pyrrolidinonylene, imidazolidinylene, pyrazolidinylene, pyrrolinylene, or a 6-membered ring, such as tetrahydropyranylene, piperidinylene, morpholinylene, piperazinylene.

The term "arylene" preferably refers to a divalent, aromatic, mono-, bi- or tricyclic hydrocarbon ring, such as phenylene, biphenylene or naphthylene.

The term "heteroarylene" preferably refers to a divalent, mono-, bi- or tricyclic aromatic ring system containing at least one heteroatom (such as oxygen, nitrogen, or sulfur), which can be same to different, such as thienylene, furylene, pyrrolylene, oxazolylene, thiazolylene, imidazolylene, pyrazolylene, isoxazolylene, isothiazolylene, pyridylene, pyridazinylene, pyrimidinylene, pyrazinylene, triazinylene.

The term "aralkylene" preferably refers to arylene substituted alkylene, wherein the arylene and alkylene are as defined herein. Normally, the arylene group may have 6-14 carbon atoms, and the alkylene group may have at most 6 carbon atoms. Exemplary aralkylene group includes, but is not limited to, benzylene, phenylethylene, phenylpropylene, phenylbutylene.

The term "substituted" means that one or more hydrogens on a designated atom is replaced with a substituent, provided that the designated atom's normal valency under the existing circumstances is not exceeded, and that the substitution results in a stable compound. Combinations of substituents and/or variables are permissible only if such combinations result in stable compounds. The substituent can be selected from the group consisting of hydroxyl, amino, halogen, cyano, nitro, carboxyl, C1-C6 alkyl or C6-C14 aryl.

The term "halogen" or "halo" preferably refers to any one of fluorine, chlorine, bromine or iodine.

The conjugate of general formula (I), (II) or (III) may also contain one or more isotopes. For example, in the compound of the present invention, hydrogen or H may be in any isotopic form, including $^1H$, $^2H$ (D or deuterium) and $^3H$ (T or tritium); carbon or C may be in any isotopic form, including $^{12}C$, $^{13}C$ and $^{14}C$; and oxygen or O may be in any isotopic form, including $^{16}O$ and $^{18}O$, etc.

The term "stereoisomer" refers to isomers formed due to the presence of at least one asymmetric center. A compound having one or more asymmetric centers can give rise to a racemate, racemic mixture, single enantiomer, diastereomer mixture and individual diastereomer. Certain individual molecules may exist as geometric isomers (cis/trans). Similarly, the conjugate of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

As to any specific conjugate disclosed herein, any of the general structure further encompasses all conformers, regioisomers as well as tautomers which might result from a set of specific substituents.

Unless otherwise indicated, when a compound as disclosed has one or more asymmetric centers but the stereochemistry is not clearly indicated in its name or structure, it should be understood that all possible stereoisomers of the compound are represented.

The present invention includes all possible crystalline forms or polymorphs of the conjugate of the present invention, either as single polymorphs, or as a mixture of more than one polymorphs, in any ratio.

The term "solvate" is defined as a form of the conjugate of the present invention, which is a complex in a liquid or solid state with a solvent molecule. Hydrate is a specific form of solvate, where the coordination is with water. In the present invention, the hydrate is the preferred solvate.

A salt, a pharmaceutically acceptable sale, of the conjugate of the present invention can be easily prepared, purified, and/or processed. An example of the pharmaceutically acceptable sale is discussed in the following reference: Berge et al., 1977, "Pharmaceutically Acceptable Salts." *J. Pharm. Sci.* Vol. 66, pp. 1-19.

For example, if the conjugate is anionic, or has a functional group which may be anionic (e.g., —COOH may be —COO$^-$), then a salt may be formed by the conjugate with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$(R)$_2^+$, NH(R)$_3^+$, N(R)$_4^+$). Examples of suitable substituted ammonium ions include, but are not limited to those derived from the following organic amines: ethylamine, ethylenediamine, dicyclohexylamine, triethylamine, butylamine, diaminocyclohexane, ethanolamine, diethanolamine, piperazine, benzylamine, phenylbenzylamine, choline and tromethamine, as well as amino acids, such as lysine and arginine. An exemplary examples of quaternary ammonium is N(CH$_3$)$_4^+$.

If the conjugate is cationic, or has a functional group which may be cationic (e.g., —NH$_2$ may be —NH$_3^+$), then a salt may be formed by the conjugate with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous acids. Examples of suitable organic anions include, but are not limited to, those derived from the following organic acids: 2-acetoxybenzoicacid, acetic acid, ascorbic acid, aspartic acid, benzoic acid, camphorsulfonic acid, cinnamic acid, citric acid, edetic acid, ethylene sulfonic acid, ethanesulfonic acid, fumaric acid, glucoheptonic acid, gluconic acid, glutamic acid, glycolic acid, hydroxymaleic acid, hydroxynaphthoic acid, isethionic acid, lactic acid, lactobionic acid, lauric acid, maleic acid, malic acid, methanesulfonic acid, mucic acid, oleic acid, oxalic acid, palmitic acid, pamoic acid, pantothenic acid, phenylacetic acid, benzenesulfonic acid, propionic acid, pyruvic acid, salicylic acid, stearic acid, succinic acid, sulfanilic acid, tartaric acid, toluene sulfonic acid and pentanoic acid. Examples of suitable polymeric organic anions include, but are not limited to, those derived from the following polymers: tannic acid or carboxymethyl cellulose.

Unless otherwise specifically indicated, specific compounds involved also encompass the salt form thereof.

Pharmaceutical Composition and Therapeutic Method

In another aspect, the present invention provides a pharmaceutical composition, comprising the conjugate of the present invention and one or more pharmaceutically acceptable carriers.

In still another aspect, the present invention provides a method for treating a disease associated with the Aβ or Tau protein pathway, comprising administering to a subject in need thereof a therapeutically effective amount of the conjugate or the pharmaceutical composition of the present invention.

The pharmaceutical composition and method of the present invention can be used for the treatment of e.g., a neurodegenerative disease, particularly Alzheimer's disease or Parkinson's disease.

The term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to, sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, rice, wheat flour, chalk, silica gel, sodium stearate, glycerol monostearate, talc, sodium chloride, dried skim milk, glycerol, propylene glycol, water, ethanol and the like. The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g., Remington's Pharmaceutical Sciences (1990).

The composition of the present invention can act systemically and/or topically. To this end, it can be administered through a suitable route, such as through injection, intravenous, intraarterial, subcutaneous, intraperitoneal, intramuscular or transdermal administration, or administered via oral, buccal, nasal, transmucosal, topical, as an ophthalmic formulation, or via inhalation.

For these routes of administration, the pharmaceutical composition of the present invention can be administered in a suitable dosage form.

Such dosage forms include, but are not limited to tablets, capsules, lozenges, hard candies, powders, sprays, creams, salves, suppositories, gels, pastes, lotions, ointments, aqueous suspensions, injectable solutions, elixirs, and syrups.

The pharmaceutical composition may be in the form of a sterile injectable preparation, for example a sterile injectable aqueous or oleaginous suspension. This suspension may be formulated according to techniques known in the art using suitable dispersing or wetting agents (such as, for example, Tween 80) and suspending agents. The sterile injectable preparation can also be formulated in a pharmaceutical acceptable diluent or solvent, such as 1,3-butylene glycol, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides, such as olive oil or castor oil, especially in their polyoxyethylated versions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical composition of this invention may be orally administered in any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and corn starch. When aqueous suspensions and/or emulsions are administered orally, the active ingredient can be suspended or dissolved in an oily phase. If desired, certain sweetening and/or flavoring and/or coloring agents may also be added.

The pharmaceutical compositions of this invention may also be administered in the form of suppositories for rectal administration. These can be prepared by mixing the conjugate of this invention with a suitable non-irritating excipient which is solid at room temperature but liquid at rectal temperature and therefore will melt in the rectum to release the active ingredient. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated as a suitable ointment containing the active components suspended or dissolved in a carrier. Carriers for topical administration of the conjugate of this invention include, but are not limited to, mineral oil, liquid petroleum, propylene glycol, polyoxyethylene polyoxypropylene polymer, emulsifying wax and water. Alternatively, the pharmaceutical composition can be formulated as a suitable lotion or cream containing the active conjugate suspended or dissolved in a carrier with suitable emulsifying agents. Suitable carriers include, but are not limited to, mineral oil, sorbitan monostearate, polysorbate 60, cetyl esters, cetearyl alcohol, 2-octyldodecanol, benzyl alcohol and water. The pharmaceutical compositions of this invention may also be topically applied to the lower intestinal tract by a rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, hydrofluorocarbons, and/or other conventional solubilizing or dispersing agents known in the art.

The term "treatment" or "treating", as used herein, means reducing, inhibiting, attenuating, ameliorating, preventing or stabilizing the progression or worsening of a disease, reducing the severity of a disease/disorder, or ameliorating symptoms associated with a disease/disorder.

As used herein, an amount of a conjugate effective for treating a disease or "therapeutically effective amount" refers to an amount of the conjugate which, when single or multiple dosages thereof being administered to a subject, effectively treats, or cures, ameliorates, reduces or improves the subject suffering from the disease.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

In some embodiments, the pharmaceutical composition of the present invention can further comprise one or more additional therapeutic or prophylactic agents, such as one or more additional agents for the treatment of a disease associated with the Aβ or Tau protein pathway, e.g., an acetylcholinesterase inhibitor (e.g., donepezil, huperzine A, tacrine, etc).

When the pharmaceutical compositions of this invention comprise a combination of the conjugate of the present invention and one or more additional therapeutic or prophylactic agents, both the conjugate and the additional therapeutic or prophylactic agents in the combinational therapy should be present at dosage levels of between about 1 to 100%, and more preferably between about 5 to 95% of the dosage normally administered in a monotherapy regimen. The additional therapeutic or prophylactic agents may be administered separately, as part of a multiple dose regimen, from the conjugate of this invention. Alternatively, those agents may be part of a single dosage form, mixed together with the conjugate of this invention in a single composition.

The conjugate of the present invention can be administered at a dosage of about 0.5 to about 1000 mg/kg body weight, or about 1 to about 100 mg/kg body weight every 4-120 hours, or administered according to requirements of a specific drug. The methods herein contemplate administration of an effective amount of conjugate of this invention or composition thereof to achieve the desired effect. Typically, the pharmaceutical compositions of this invention will be administered from about 1 to 6 times per day or alternatively, as a continuous infusion. Such administration can be used as a chronic or acute therapy. The amount of the active ingredient which may be combined with the carrier materials to produce a single dosage will vary, depending upon the subject to be treated and the particular mode of administration. A representative formulation may contain between from about 5% to about 95% of the active conjugate (w/w). Alternatively, such a formulation contains about 20% to about 80% of the active conjugate.

Lower or higher doses of the conjugate of the present invention than those recited above may be required. However, the specific dose level and therapeutic regimen for any particular patient will depend on a variety of factors including the activity of the specific conjugate employed; the age, body weight, general health, sex and diet of the individual being treated; the time administration; the rate of excretion; drug combination; the severity of the particular disease, condition or symptom; and individual disposal and the discretion of an attendant physician to the disease, condition or symptom.

Upon improvement of a patient's condition, a maintenance dose of a conjugate, composition or combination of this invention may be administered, if necessary. Subsequently, when the symptom is reduced to a desired level, the dosage, the frequency of administration or both can be reduced, to a level at which the improved condition is maintained. Patients may, however, require intermittent treatment upon any recurrence of disease symptoms.

The invention is further illustrated by the following Examples. These examples are provided for illustrative purposes only and are not intended to limit in any way the invention

EXAMPLES

Unless noted otherwise, the starting materials and reagents were all purchased from commercial suppliers and were used without further purification in the following Examples.

Example 1: Preparation of Conjugate A02

Conjugate A02 was prepared according to Scheme 1.

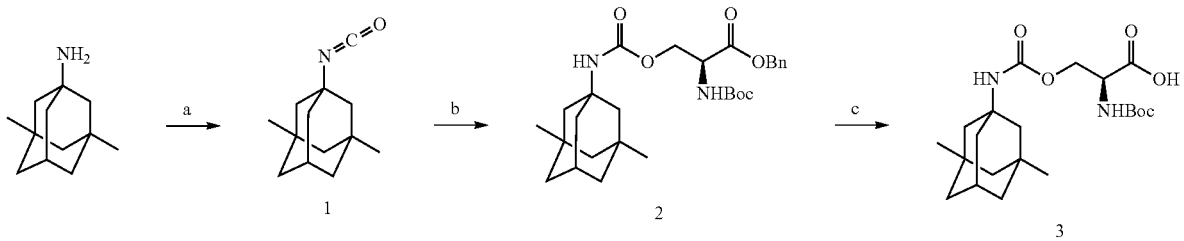

-continued

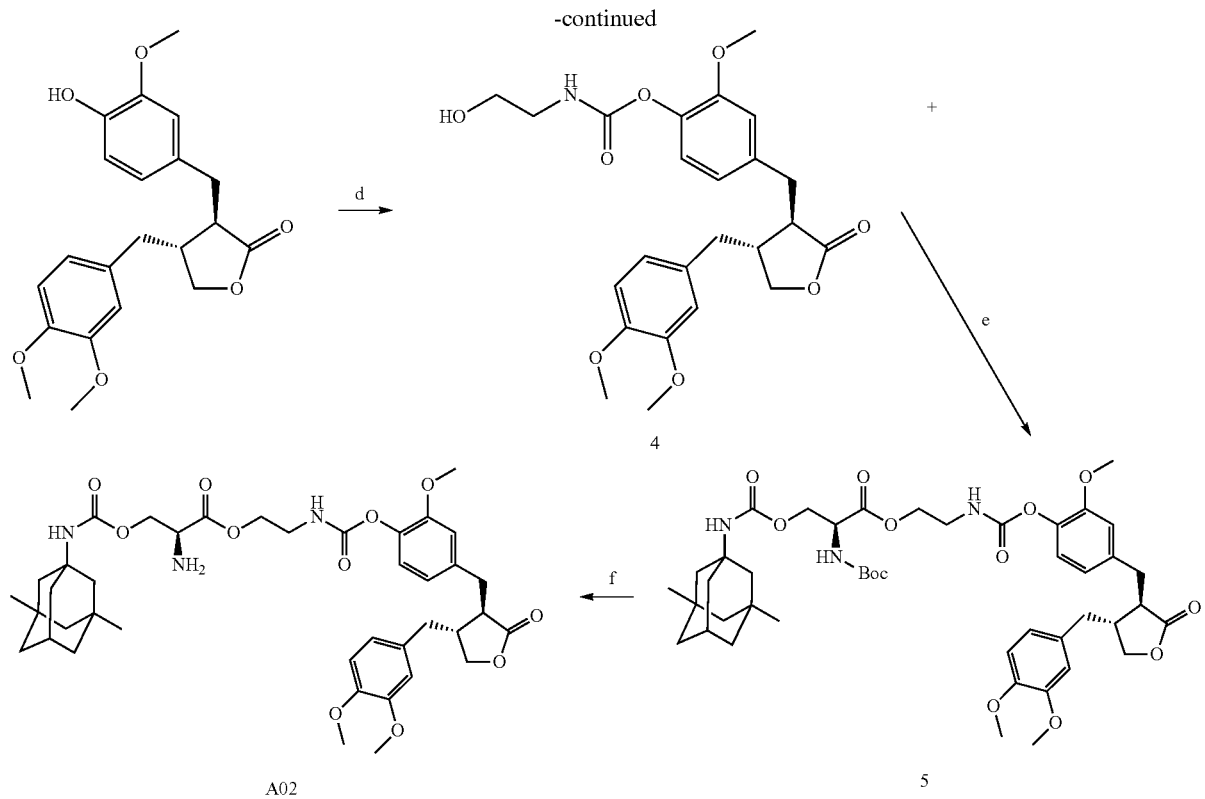

Reaction reagents and conditions: a) toluene, triphosgene, pyridine, room temperature; b) N-Boc-serine benzyl ester, triethylamine; c) palladium/carbon, hydrogen, methanol; d) p-nitrophenyl chloroformate, triethylamine, 2-aminoethanol; e) 1-ethyl-(3-dimethylaminopropyl)carbodiimide, 4-dimethylaminopyridine, triethylamine, dichloromethane; f) A solution of HCl in dioxane.

Step a). Preparation of Compound 1:

Triphosgene (1.6 equivalents) was dissolved in toluene under a $N_2$ atmosphere, and cooled to 0° C. Pyridine (6.0 equivalents) was slowly dropwise added to the reaction mixture, followed by addition of memantine hydrochloride (1.0 equivalent), and the reaction was performed at room temperature overnight. The reaction mixture was added with ice-water, and extracted twice with ethyl acetate; the organic phase was combined, dried over sodium sulfate, and concentrated to afford a liquid product, which was directly used in the next reaction without purification.

$^1$H NMR (400 MHz, DMSO-d$^6$) δ: 2.11 (dt, J=6.3, 3.1 Hz, 1H), 1.70 (d, J=1.4 Hz, 2H), 1.51 (q, J=12.1 Hz, 4H), 1.37-1.21 (m, 4H), 1.12 (dd, J=3.8, 1.8 Hz, 2H), 0.84 (s, 6H).

Step b). Preparation of Compound 2:

Compound 1 obtained in Step a) was dissolved in dry tetrahydrofuran, followed by addition of N-Boc-serine benzyl ester (0.8 equivalent) and triethylamine (1 equivalent). The reaction was performed at 50°C. for 24 hours, was and after TLC indicated the disappearance of the starting material, D-serine, the reaction solution was concentrated to obtain a product, which was purified by column chromatography to afford a pure product.

$^1$H NMR (400 MHz, DMSO-d$^6$) δ: 27.44-7.30 (mdt, J=6.3, 7.22 (d, =8.1 Hz, 1H), 6.88 (s, 1H), 5.14 (s, 2H), 4.34-4.10 (m, 2H), 2.05 (s, 1H), 1.66 (s, 2H), 1.55-1.20 (m, 18H), 1.07 (s, 2H), 0.80 (s, 6H).

Step c). Preparation of Compound 3:

Compound 2 obtained in Step b) was dissolved in methanol, followed by addition of 10% palladium/carbon; the reaction was heated to 50° C., and hydrogenated with hydrogen (40 Psi) for 3 hours. Palladium/carbon was removed by filtration, the filtrate was concentrated, and the concentrate was directly used in the next reaction without purification.

$^1$H NMR (400 MHz, DMSO-d$^6$) δ: 6.98-6.75 (m, 2H), 4.21-3.98 (m, 3H), 2.06 (m, 1H), 1.66 (m, 2H), 1.49 (s, 4H), 1.42-1.19 (m, 13H), 1.08 (s, 2H), 0.81 (s, 6H).

Step d). Preparation of Compound 4:

Arctigenin (1.0 equivalent) and p-nitrophenyl chloroformate (1.0 equivalent) were dissolved in dichloromethane, and triethylamine (2.0 equivalents) was added to the mixture. The reaction was performed at room temperature for 3 hours. 2-aminoethanol (1.1 equivalents) and triethylamine (2.0 equivalents) were then added. The reaction was performed at room temperature overnight, and the reaction solution was concentrated, and purified by column chromatography, to afford the product.

$^1$H NMR (400 MHz, CDCl$_3$) δ: 7.02 (d, J=8.0 Hz, 1H), 6.78 (m, 2H), 6.68 (dd, J=8.0, 1.6 Hz, 1H), 6.57 (dd, J=8.1, 1.7 Hz, 1H), 6.52 (d, J=1.8 Hz, 1H), 5.57 (s, 1H), 4.18 (dd, J=9.0, 7.2 Hz, 1H), 3.93-3.79 (m, 10H), 3.44 (m, 2H), 2.98 (d, J=5.9 Hz, 2H), 2.72-2.48 (m, 4H), 1.97 (s, 3H).

Step e). Preparation of Compound 5:

Compound 3 (1.0 equivalent) obtained in Step c), 1-ethyl-(3-dimethylaminopropyl)carbodiimide (1.5 equivalents), 4-dimethylaminopyridine (0.2 equivalent) and triethylamine (1.5 equivalents) were dissolved in dichloromethane. The reaction was stirred at room temperature for 15 minutes, followed by addition of compound 4 (1.0 equivalent) obtained in Step d), and the reaction was then stirred at room temperature overnight. The reaction was added with a suitable amount of water, the organic phase was separated, and the aqueous phase was extracted with dichloromethane once, the organic phase was combined, washed once with dilute hydrochloric acid, then washed with saturated brine, dried over sodium sulfate, concentrated, and purified by column chromatography to afford the product.

9H), 3.52 (t, J=5.0 Hz, 2H), 3.01-2.89 (m, 2H), 2.79-2.73 (m, 1H), 2.58 (m, 3H), 2.08 (m, 1H), 1.76 (d, J=1.9 Hz, 2H), 1.60-1.47 (m, 4H), 1.35-1.26 (m, 6H), 1.11 (s, 2H), 0.82 (s, 6H).

LC-MS (ESI) 752.4 [M+H]$^+$.

Example 2: Preparation of Conjugate A04

Conjugate A04 was prepared according to Scheme 2.

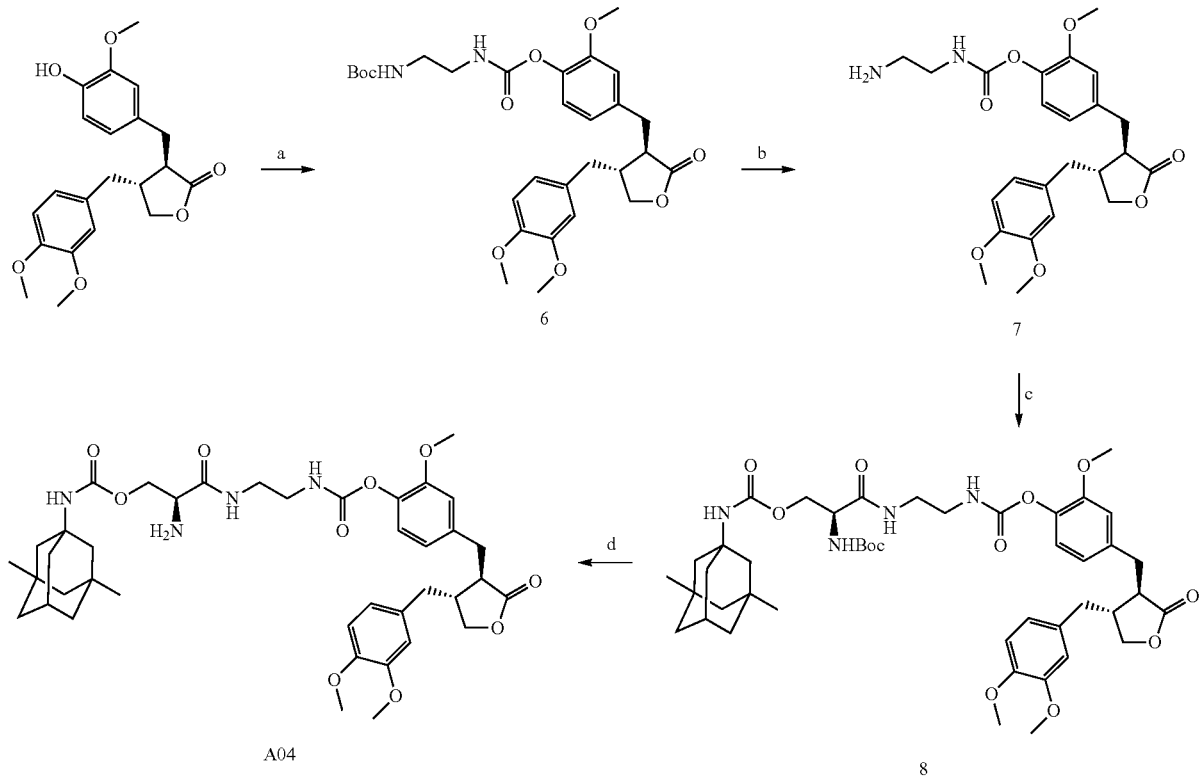

$^1$H NMR (400 MHz, CDCl$_3$) δ: 7.32-7.25 (m, 1H), 7.02 (d, J=8.0 Hz, 1H), 6.85-6.76 (m, 2H), 6.68 (d, J=8.0 Hz, 1H), 6.55 (dd, J=13.0, 5.0 Hz, 2H), 5.91 (s, 1H), 5.43 (d, J=7.8 Hz, 1H), 4.82 (s, 1H), 4.65-4.44 (m, 2H), 4.22 (dd, J=23.0, 11.0 Hz, 2H), 3.85 (dd, J=21.6, 13.6 Hz, 9H), 3.55 (d, J=5.3 Hz, 1H), 3.36-3.27 (m, 3H), 3.01-2.93 (m, 2H), 2.72-2.50 (m, 4H), 2.09 (s, 1H), 1.95 (dd, J=8.0, 5.1 Hz, 3H), 1.55-1.43 (m, 10H), 1.28 (dd, J=12.2, 4.9 Hz, 6H), 1.10 (s, 2H), 0.81 (s, 6H).

Step f). Preparation of Conjugate A02:

Compound 5 obtained in Step e) was added to a reaction flask, followed by addition of a suitable amount of a solution of HCl in dioxane, and the reaction was stirred at room temperature overnight. The reaction was concentrated, slurried by adding a suitable amount of ethyl ether, and filtered to afford a hydrochloride salt of a conjugate, which was treated with a saturated aqueous sodium bicarbonate solution to afford a free conjugate, which was extracted with ethyl acetate, dried over sodium sulfate, and concentrated to afford the target product.

$^1$H NMR (400 MHz, CD$_3$OD) δ: 6.98 (d, J=8.0 Hz, 1H), 6.87-6.84 (m, 2H), 6.75-6.64 (m, 3H), 4.61-4.29 (m, 5H), 4.23-4.14 (m, 1H), 3.97 (t, J=8.5 Hz, 1H), 3.84-3.74 (m,

Reaction reagents and conditions: a) triphosgene, toluene, pyridine, room temperature, N-tert-butyloxycarbonyl-1,2-ethylenediamine; b) a solution of HCl in dioxane; c) 1-ethyl-(3-dimethylaminopropyl)carbodiimide, 4-dimethylaminopyridine, triethylamine, dichloromethane; d) a solution of HCl in dioxane.

Step a). Preparation of Compound 6:

Compound 6 was prepared according to a method similar to that in Step a) and Step b) of Example 1 wherein compound 2 was prepared from memantine hydrochloride.

$^1$H NMR (400 MHz, CDCl$_3$) δ: 6.96 (d, J=8.0 Hz, 1H), 6.73 (m, 2H), 6.63 (dd, J=8.0, 1.6 Hz, 1H), 6.49 (m, 2H), 5.46 (s, 1H), 4.84 (s, 1H), 4.19-4.10 (m, 1H), 3.91-3.68 (m, 10H), 3.39-3.25 (m, 4H), 2.94 (d, J=5.8 Hz, 2H), 2.66-2.43 (m, 4H), 1.43 (s, 9H).

Step b). Preparation of Compound 7:

Compound 6 obtained in Step a) was added to a reaction flask, followed by addition of a suitable amount of a solution of HCl in dioxane, and the reaction was performed at room temperature overnight. The reaction solution was concentrated, treated with a saturated aqueous sodium bicarbonate solution to obtain a free product, extracted with ethyl acetate, dried over sodium sulfate, and concentrated to afford the target product.

¹H NMR (400 MHz, CDCl₃) δ 7.00 (d, J=7.9 Hz, 1H), 6.76 (m, 2H), 6.66 (d, J=7.8 Hz, 1H), 6.58-6.49 (m, 2H), 5.56 (s, 1H), 4.20-4.13 (m, 1H), 3.85 (m, 11H), 3.47 (s, 2H), 2.96 (d, J=5.8 Hz, 2H), 2.70-2.45 (m, 4H).

Step c). Preparation of Compound 8:

Compound 8 was prepared according to a method similar to that in Step e) of Example 1 wherein compound 5 was prepared.

¹H NMR (400 MHz, CDCl₃) δ: 6.94 (s, 1H), 6.68 (m, 3H), 6.51 (m, 2H), 5.36-5.17 (m, 2H), 4.32-3.98 (m, 7H), 3.92-3.69 (m, 10H), 2.92 (m, 2H), 2.71-2.46 (m, 4H), 2.12-1.95 (m, 6H), 1.41 (m, 13H), 0.77 (s, 6H).

Step d). Preparation of Conjugate A04:

Compound 8 obtained in Step c) was added to a reaction flask, followed by addition of a suitable amount of a solution of HCl in dioxane, and the reaction was performed at room temperature overnight. The reaction solution was concentrated, slurried by adding a suitable amount of ethyl ether, and filtered to afford a hydrochloride salt of conjugate A04, which was treated with a saturated aqueous sodium bicarbonate solution to afford free conjugate A04, which was extracted with ethyl acetate, dried over sodium sulfate, and concentrated to afford the target product.

¹H NMR (400 MHz, CD₃OD) δ: 6.98 (d, J=8.0 Hz, 1H), 6.85 (m, 2H), 6.73 (d, J=8.0 Hz, 1H), 6.71-6.63 (m, 2H), 4.38 (m, 2H), 4.21 (t, J=8.1 Hz, 1H), 4.11 (s, 1H), 3.97 (t, J=8.5 Hz, 1H), 3.86-3.66 (m, 10H), 3.50 (m, 1H), 3.33 (m, 4H), 2.99-2.87 (m, 2H), 2.76 (m, 1H), 2.65-2.51 (m, 3H), 2.10 (s, 1H), 1.76 (s, 2H), 1.55 (m, 4H), 1.32 (m, 6H), 1.13 (s, 2H), 0.83 (s, 6H).

LC-MS (ESI) 751 [M+H]⁺.

Example 3: Preparation of Conjugate A10

Conjugate A10 was prepared according to Scheme 3.

Scheme 3
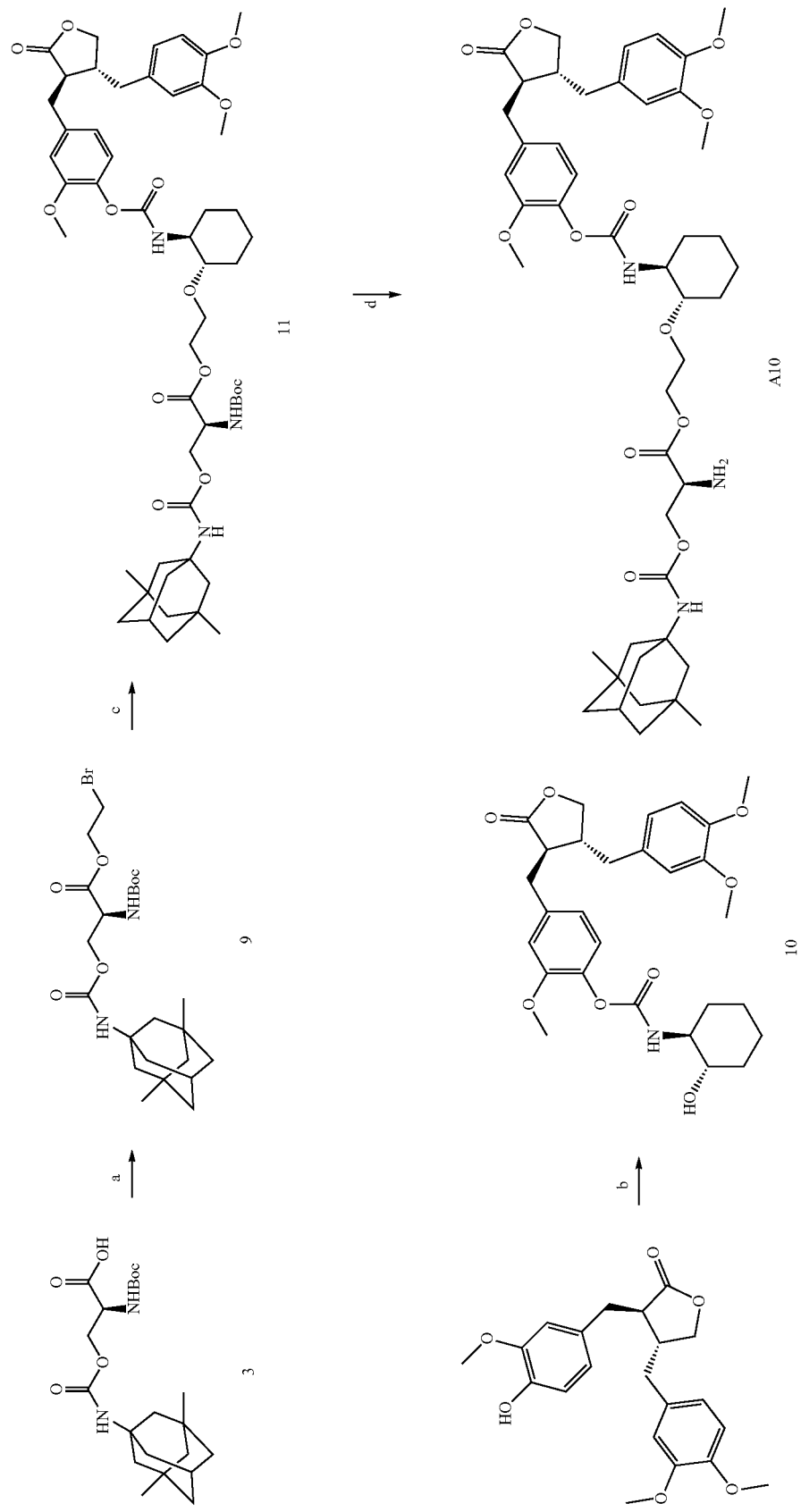

Reaction reagents and conditions: a) 1-ethyl-(3-dimethylaminopropyl)carbodiimide, 4-dimethylaminopyridine, triethylamine, dichloromethane; b) p-nitrophenyl chloroformate, triethylamine, (S,S)-2-aminocyclohexanol; c) potassium carbonate, methanol; d) a solution of HCl in dioxane.

Step a). Preparation of Compound 9:

Compound 3 (1.0 equivalent) obtained in Step c) of Example 1, 1-ethyl-(3-dimethylaminopropyl)carbodiimide (1.5 equivalents), 4-dimethylaminopyridine (0.2 equivalent) and triethylamine (1.5 equivalents) were dissolved in dichloromethane, the reaction solution was stirred at room temperature for 15 minutes, followed by addition of 2-bromoethanol (1.0 equivalent), and the resultant reaction solution was stirred at room temperature overnight. A suitable amount of water was added to the reaction solution, the dichloromethane layer was separated, and the aqueous phase was extracted once with dichloromethane; the organic phase was combined, washed once with dilute hydrochloric acid, then washed with saturated brine, dried over sodium sulfate, concentrated, and purified by column chromatography to afford the product.

LC-MS (ESI) 518 [M+H]$^+$.

Step b). Preparation of Compound 10:

Arctigenin (1.0 equivalent) and p-nitrophenyl chloroformate (1.0 equivalent) were dissolved in dichloromethane, triethylamine (2.0 equivalents) was added to the mixture, and the reaction was performed at room temperature for 3 hours, (S,S)-2-aminocyclohexanol (1.1 equivalents) and triethylamine (2.0 equivalents) were added, the reaction was performed at room temperature overnight, and the reaction solution was concentrated, and purified by column chromatography to afford the product.

LC-MS (ESI) 514 [M+H]$^+$.

Step c). Preparation of Compound 11:

Compound 9 (1 equivalent) obtained in Step a) and compound 10 (1 equivalent) obtained in Step b) were dissolved in methanol, potassium carbonate (2.0 equivalents) was added, and the reaction was refluxed overnight; after TLC indicated complete reaction of the starting material, the reaction solution was concentrated, followed by addition of suitable amounts of water and dichloromethane, stirred for 10 minutes, and the organic phase was washed with saturated brine, dried over sodium sulfate, concentrated, and purified by column chromatography to afford the product.

LC-MS (ESI) 951 [M+H]$^+$.

Step d). Preparation of Conjugate A10:

Compound 11 obtained in Step c) was added to a reaction flask, followed by addition of a suitable amount of a solution of HCl in dioxane, and the reaction was performed at room temperature overnight. The reaction solution was concentrated, slurried by adding a suitable amount of ethyl ether, and filtered to afford a hydrochloride salt of conjugate A10, which was treated with a saturated aqueous sodium bicarbonate solution to afford free conjugate A10, which was extracted with ethyl acetate, dried over sodium sulfate, and concentrated to afford the target product.

LC-MS (ESI) 851 [M+H]$^+$.

Example 4: Preparation of Conjugate A31

Conjugate A31 was prepared according to Scheme 4.

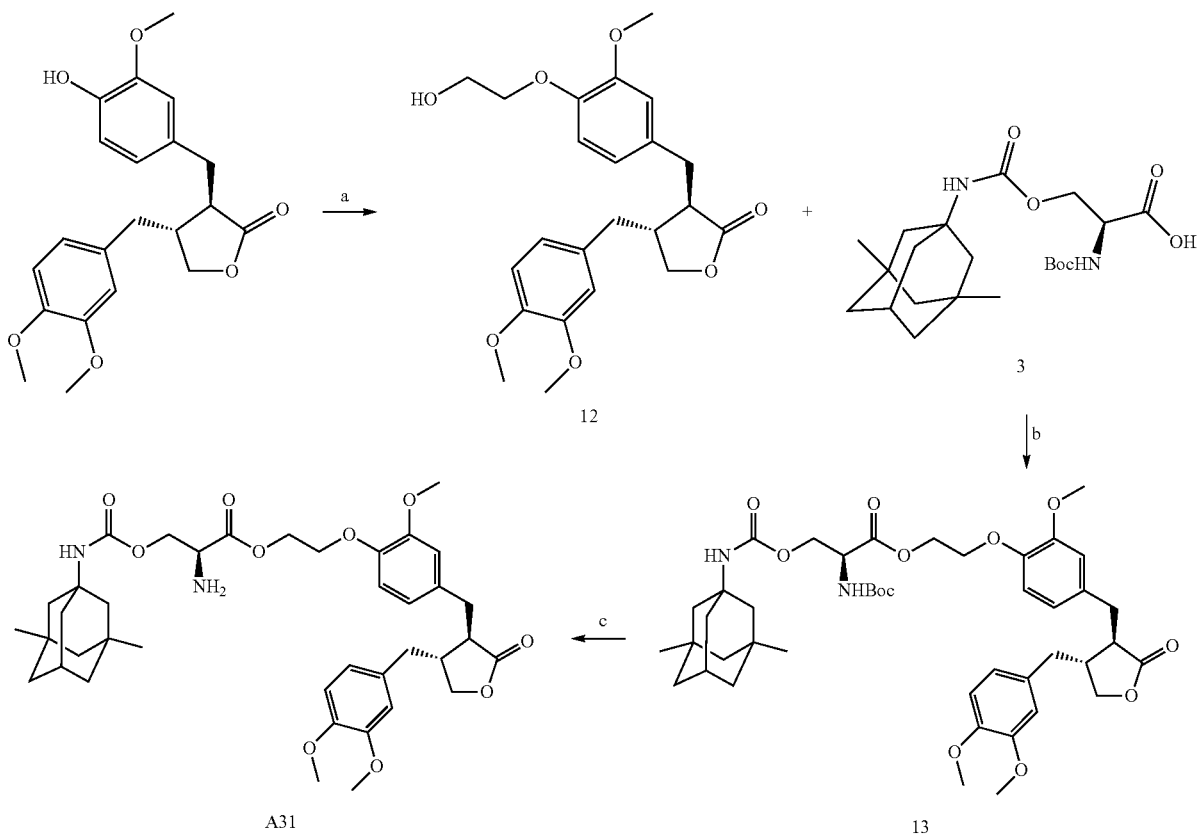

Reaction reagents and conditions: a) potassium carbonate, acetone, bromoethanol, reflux; b) 1-ethyl-(3-dimethylaminopropyl)carbodiimide, 4-dimethylaminopyridine, triethylamine, dichloromethane; c) a solution of HCl in dioxane.

Step a). Preparation of Compound 12:

Arctigenin (1 equivalent) was dissolved in a suitable amount of acetone, potassium carbonate (1.5 equivalents) was added, followed by addition of bromoethanol (1.5 equivalents) with stirring; the reaction mixture was refluxed until disappearance of the starting material, the solid was filtered off, and the filtrate was concentrated, and purified by column chromatography to afford the target product.

$^1$H NMR (400 MHz, DMSO) δ: 6.89-6.77 (m, 3H), 6.72-6.57 (m, 3H), 4.82 (t, J=5.5 Hz, 1H), 4.13-4.06 (m, 1H), 3.96-3.85 (m, 3H), 3.70 (m, 11H), 2.89-2.70 (m, 3H), 2.48 (m, 3H).

Step b). Preparation of Compound 13:

Compound 13 was prepared according to a method similar to that in Step e) of Example 1 wherein compound 5 was prepared.

$^1$H NMR (400 MHz, DMSO) δ: 8.68 (br, 2H), 6.91-6.52 (m, 7H), 4.50-4.06 (m, 6H), 3.95-3.84 (m, 2H), 3.73-3.67 (m, 9H), 2.88-2.71 (m, 3H), 2.49-2.42 (m, 2H), 2.04 (m, 1H), 1.66 (m, 2H), 1.54-1.38 (m, 13H), 1.32-1.16 (m, 6H), 1.09 (m, 2H), 0.79 (s, 6H). LC-MS (ESI) 809 [M+H]$^+$.

Step c). Preparation of Conjugate A31:

Compound 13 obtained in Step b) was added to a reaction flask, a suitable amount of a solution of HCl in dioxane was added, and the reaction was performed at room temperature overnight. The reaction solution was concentrated, slurried by adding a suitable amount of ethyl ether, and filtered to afford a hydrochloride salt of the conjugate, which was treated with a saturated aqueous sodium bicarbonate solution to afford the free conjugate, which was extracted with ethyl acetate, dried over sodium sulfate, and concentrated to afford the target product.

$^1$H NMR (400 MHz, DMSO) δ: 8.69 (br, 2H), 6.92-6.53 (m, 7H), 4.50-4.06 (m, 6H), 3.94-3.83 (m, 2H), 3.73-3.68 (m, 9H), 2.88-2.70 (m, 3H), 2.49-2.42 (m, 2H), 2.04 (m, 1H), 1.66 (m, 2H), 1.54-1.38 (m, 4H), 1.33-1.17 (m, 6H), 1.07 (m, 2H), 0.78 (s, 6H).

LC-MS (ESI) 709 [M+H]$^+$.

Example 5: Preparation of Conjugate A01

Conjugate A01 was prepared according a method similar to that of Example 1 wherein conjugate A02 was prepared.

$^1$H NMR (400 MHz, CDCl$_3$) δ: 7.00 (d, J=8.0 Hz, 1H), 6.86-6.74 (m, 2H), 6.69 (d, J=8.0 Hz, 1H), 6.60-6.45 (m, 2H), 5.12 (d, J=13.1 Hz, 1H), 4.56-4.24 (m, 4H), 4.16 (m, 1H), 3.91-3.58 (m, 12H), 3.17 (s, 1H), 3.07 (s, 2H), 2.98 (d, J=5.7 Hz, 2H), 2.73-2.43 (m, 8H), 2.11 (s, 1H), 1.54-1.46 (m, 3H), 1.37-1.27 (m, 4H), 0.83 (s, 6H). LRMS (ESI) 766 [M+H]$^+$.

Example 6: Preparation of Conjugate A03

Conjugate A03 was prepared according a method similar to that of Example 1 wherein conjugate A02 was prepared.

$^1$H NMR (400 MHz, CDCl$_3$) δ: 8.85 (s, 2H), 7.10-6.49 (m, 6H), 5.99 (m, 2H), 4.40 (m, 6H), 3.81 (m, 9H), 3.31 (m, 7H), 2.74-2.48 (m, 3H), 2.06-1.90 (m, 3H), 1.76-1.42 (m, 5H), 1.25 (m, 7H), 0.78 (s, 6H).

LRMS (ESI) 766 [M+H]$^+$.

Example 7: Preparation of Conjugate A15

Conjugate A15 was prepared according to a method similar to that of Example 2 wherein conjugate A04 was prepared.

$^1$H NMR (400 MHz, CDCl$_3$) δ: 6.99 (d, J=8.0 Hz, 1H), 6.77 (m, 2H), 6.66 (d, J=7.8 Hz, 1H), 6.58-6.48 (m, 2H), 4.41 (m, 2H), 4.16 (m, 1H), 3.92-3.75 (m, 12H), 3.22 (s, 1H), 2.96 (s, 2H), 2.70-2.13 (m, 8H), 1.75-1.53 (d, J=21.5 Hz, 7H), 1.34-1.14 (m, 4H), 0.84 (m, 9H).

LC-MS (ESI) 791 [M+H]$^+$.

Example 8: Preparation of Conjugate A17

Conjugate A17 was prepared according to a method similar to that of Example 2 wherein conjugate A04 was prepared.

$^1$H NMR (400 MHz, CDCl$_3$) δ: 8.42 (s, 1H), 6.96 (d, J=7.5 Hz, 1H), 6.73 (m, 2H), 6.64 (t, J=7.2 Hz, 1H), 6.60-6.44 (m, 2H), 4.71-4.09 (m, 4H), 3.89-3.70 (m, 12H), 3.36 (s, 1H), 2.91 (d, J=5.3 Hz, 2H), 2.75-2.45 (m, 4H), 2.13-1.42 (m, 13H), 1.27 (dd, J=29.8, 11.4 Hz, 6H), 1.09 (s, 2H), 0.80 (s, 6H).

LC-MS (ESI) 791 [M+H]$^+$.

Example 9: Preparation of Conjugates A05-A09, A11-A14, A16, A18-A30 and A32-A34

Conjugates A05-A09, A11-A14, A16, A18-A30 and A32-A34 were prepared according to methods similar to that of Example 1, and the characterization data thereof are as follows.

| Conjugate No. | LC-MS |
| --- | --- |
| A05 | 836 [M + H]$^+$ |
| A06 | 838 [M + H]$^+$ |
| A07 | 708 [M + H]$^+$ |
| A08 | 752 [M + H]$^+$ |
| A09 | 752 [M + H]$^+$ |
| A11 | 806 [M + H]$^+$ |
| A12 | 806 [M + H]$^+$ |
| A13 | 806 [M + H]$^+$ |
| A14 | 762 [M + H]$^+$ |
| A16 | 777 [M + H]$^+$ |
| A18 | 748 [M + H]$^+$ |
| A19 | 762 [M + H]$^+$ |
| A20 | 762 [M + H]$^+$ |
| A21 | 835 [M + H]$^+$ |
| A22 | 835 [M + H]$^+$ |
| A23 | 821 [M + H]$^+$ |
| A24 | 734 [M + H]$^+$ |
| A25 | 748 [M + H]$^+$ |
| A26 | 748 [M + H]$^+$ |
| A27 | 777 [M + H]$^+$ |
| A28 | 734 [M + H]$^+$ |
| A29 | 748 [M + H]$^+$ |
| A30 | 748 [M + H]$^+$ |
| A32 | 862 [M + H]$^+$ |
| A33 | 876 [M + H]$^+$ |
| A34 | 876 [M + H]$^+$ |

Example 10: Preparation of Conjugate A35

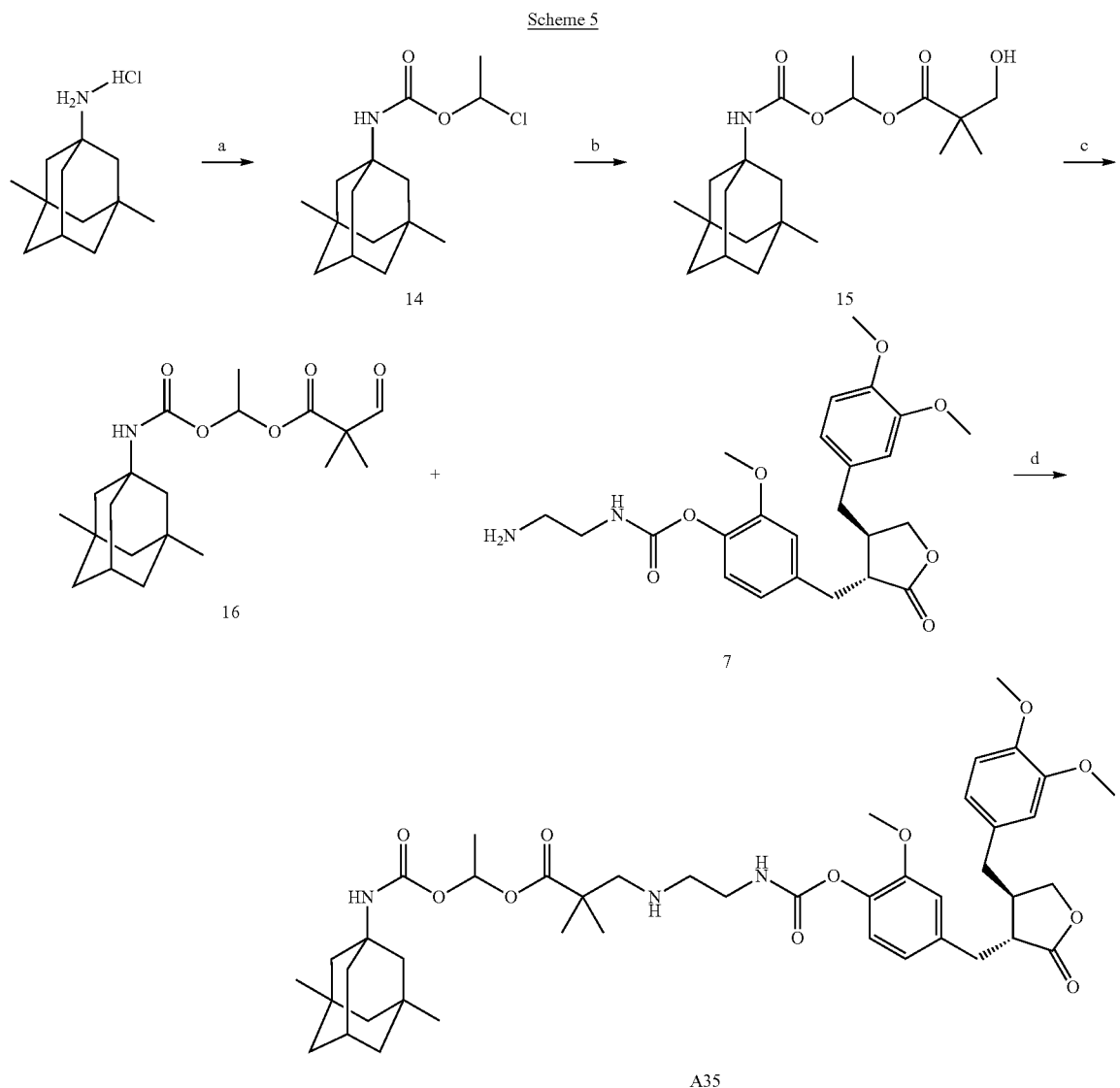

Reaction reagents and conditions: A) 1-chloroethyl chloroformate, 4-dimethylaminopyridine, dichloromethane, 0° C.; b) N-methylmorpholine, 2,2-dimethyl-3-hydroxypropionic acid, tetrahydrofuran, 50° C.; c) 2,2,6,6-tetramethylpiperidine-1-oxide, trichlorotriazine, dichloromethane; d) sodium triacetoxyborohyride, 1,2-dichloroethane.

Step a). Preparation of Compound 14:

A suspension of memantine hydrochloride (1 equivalent) in dichloromethane was cooled to 0° C., followed by addition of a catalytic amount of 4-dimethylaminopyridine and triethylamine (3 equivalents), a solution of 1-chloroethyl chloroformate (1.1 equivalents) in dichloromethane was slowly dropwise added, and the reaction solution was stirred at room temperature overnight. The reaction mixture was added with a suitable amount of water, the organic phase was separated, and the aqueous phase was extracted with dichloromethane, the organic phase was combined, washed with dilute hydrochloric acid, saturated sodium bicarbonate, and saturated brine, respectively, dried over sodium sulfate, concentrated, and the product was used directly in the next reaction without purification.

$^1$H NMR (400 MHz, CDCl$_3$) δ: 6.54-6.46 (m, 1H), 4.72 (m, 1H), 2.18 (m, 1H), 1.88-1.70 (m, 4H), 1.66-1.49 (m, 4H), 1.43-1.24 (m, 5H), 1.16 (d, J=7.3 Hz, 2H), 0.88 (s, 6H).

Step b). Preparation of Compound 15:

Compound 14 (1 equivalent) obtained in Step a) and N-methylmorpholine (1.2 equivalents) were dissolved in a suitable amount of tetrahydrofuran, 2,2-dimethyl-3-hydroxypropionic acid (1 equivalent) was added to the reaction solution, which was heated to 50° C., until TLC indicated the reaction was complete. The reaction solution was concentrated, the concentrate was added with a suitable amount of dilute hydrochloric acid, the organic phase was separated, washed with saturated aqueous sodium bicarbonate solution and saturated brine, dried over sodium sulfate, and concentrated to afford the product.

$^1$H NMR (400 MHz, CDCl$_3$) δ: 6.72-6.63 (m, 1H), 4.69 (m, 1H), 4.07 (s, 1H), 3.66 (d, J=11.4 Hz, 1H), 3.43 (d, J=11.4 Hz, 1H), 2.15 (m, 1H), 1.86-1.51 (m, 7H), 1.46 (t, J=5.7 Hz, 2H), 1.40-1.21 (m, 8H), 1.19-1.10 (m, 4H), 0.86 (s, 6H).

Step c). Preparation of Compound 16:

Compound 15 (1 equivalent) obtained in Step b) and trichlorotriazine (1.5 equivalents) were dissolved in a suitable amount of dichloromethane, followed by addition of a catalytic amount of 2,2,6,6-tetramethylpiperidine-1-oxide, and the reaction mixture was stirred at room temperature until complete reaction of the starting material. A suitable amount of saturated sodium thiosulfate was added, the organic phase was washed with saturated sodium bicarbonate and saturated brine, respectively, dried over sodium sulfate, concentrated, and purified by column chromatography to afford target compound 16.

LC-MS: 366 [M+H]$^+$.

Step d). Preparation of Conjugate A35:

Compound 7 (1 equivalent) obtained in Step b) of Example 2 and compound 16 (1 equivalent) obtained in Step c) of the present Example were dissolved in a suitable amount of 1,2-dichloroethane, a suitable amount of sodium triacetoxyborohyride was added, and the reaction was performed at room temperature until TLC indicated complete reaction of the starting material. A suitable amount of saturated aqueous ammonium chloride solution was added, the organic phase was separated, the aqueous phase was extracted once with dichloromethane, the organic phase was combined, washed once with saturated brine, dried over sodium sulfate, concentrated, and separated by column chromatography to afford target compound, conjugate A35.

$^1$H NMR (400 MHz, CDCl$_3$) δ: 7.03 (d, J=8.0 Hz, 1H), 6.83-6.64 (m, 4H), 6.60-6.51 (m, 2H), 6.04 (m, 1H), 4.84 (m, 1H), 4.17 (dd, J=9.0, 7.2 Hz, 1H), 4.06 (s, 1H), 3.93-3.77 (m, 10H), 3.51 (m, 2H), 3.04-2.49 (m, 9H), 2.10 (s, 1H), 1.75 (s, 2H), 1.52 (m, 6H), 1.38-1.10 (m, 12H), 0.83 (m, 6H).

Example 11: Preparation of Conjugate A36

Scheme 6

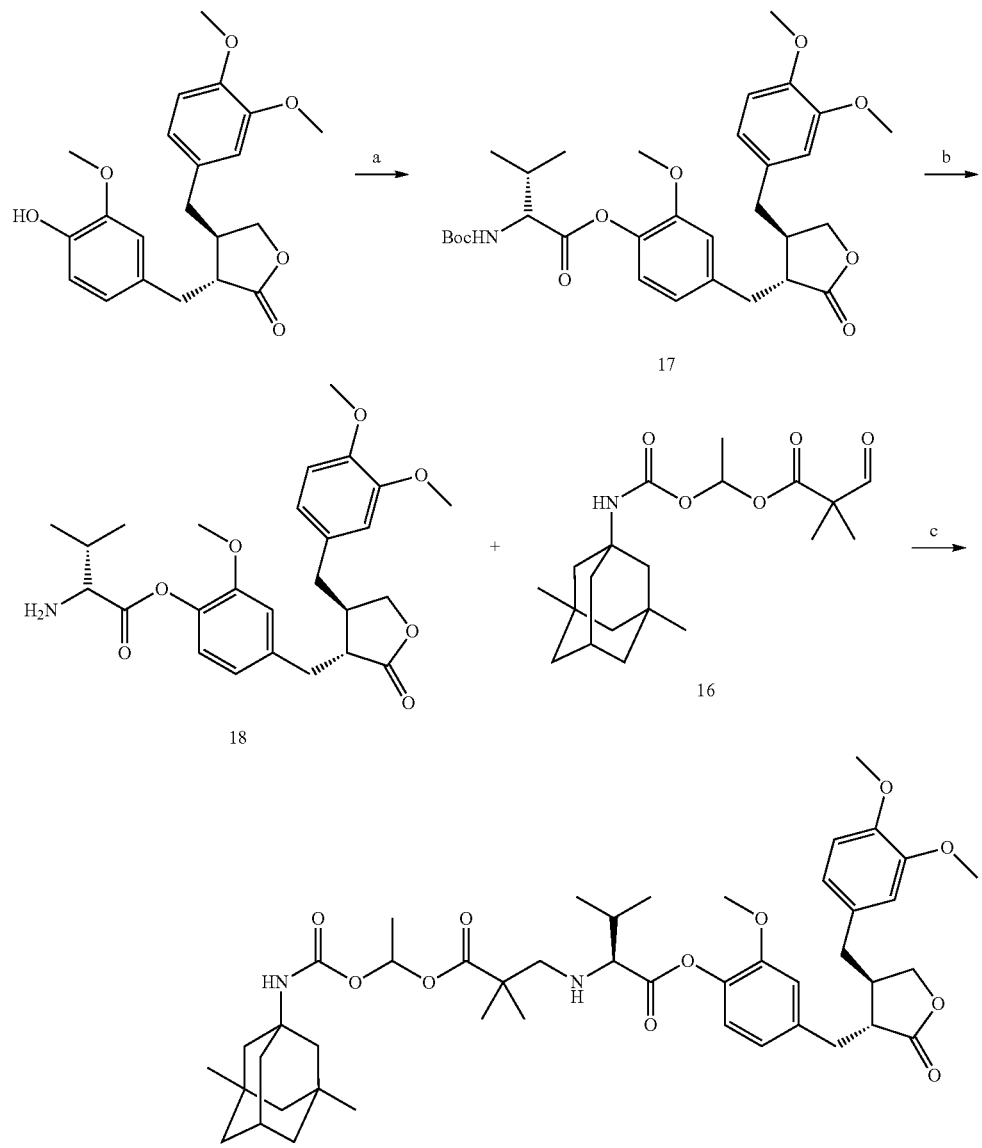

Reaction reagents and conditions: a) N-Boc-D-valine, 1-ethyl-(3-dimethylaminopropyl)carbodiimide, 4-dimethylaminopyridine, dichloromethane; b) a solution of HCl in dioxane; c) sodium triacetoxyborohyride, 1,2-dichloroethane.

Step a). Preparation of Compound 17:

N-Boc-D-valine (1 equivalent) was dissolved in a suitable amount of dichloromethane, 1-ethyl-(3-dimethylaminopropyl)carbodiimide (1.2 equivalents) and 4-dimethylaminopyridine (5 equivalents) were added; after the reaction was stirred at room temperature for 15 minutes, arctigenin (1 equivalent) was added, and the reaction was then stirred at room temperature overnight. A suitable amount of water was added to the reaction solution, the organic phase was separated, washed with dilute hydrochloric acid, saturated sodium bicarbonate and saturated brine, respectively, dried over sodium sulfate, concentrated, and purified by column chromatography to afford compound 17.

$^1$H NMR (400 MHz, CDCl$_3$) δ: 6.97 (d, J=8.0 Hz, 1H), 6.79 (m, 2H), 6.69 (dd, J=8.0, 1.6 Hz, 1H), 6.54 (m, 2H), 5.10 (d, J=9.0 Hz, 1H), 4.53 (dd, J=9.2, 4.2 Hz, 1H), 4.21-4.15 (m, 1H), 3.97-3.70 (m, 10H), 3.00 (d, J=5.8 Hz, 2H), 2.72-2.32 (m, 5H), 1.49 (s, 9H), 1.12 (d, J=6.9 Hz, 3H), 1.05 (d, J=6.9 Hz, 3H).

Step b). Preparation of Compound 18:

Compound 17 (1 equivalent) obtained in Step a) was added to a reaction flask, to which a suitable amount of a solution of HCl in dioxane was added, the reaction solution was stirred at room temperature until disappearance of the starting material, and was concentrated to afford compound 18.

$^1$H NMR (400 MHz, DMSO) δ: 8.73 (m, 3H), 7.08 (dd, J=8.0, 2.6 Hz, 1H), 7.03 (s, 1H), 6.84 (m, 2H), 6.66 (d, J=1.7 Hz, 1H), 6.63-6.58 (m, 1H), 4.15 (dd, J=15.3, 7.2 Hz, 2H), 3.93 (dd, J=17.1, 9.1 Hz, 1H), 3.79-3.67 (m, 10H), 2.96 (m, 1H), 2.82 (m, 2H), 2.36 (m, 1H), 1.11 (m, 6H).

Step c). Preparation of Conjugate A36:

Conjugate A36 was prepared according to a method similar to that of Step d) of Example 10 wherein conjugate A35 was prepared.

$^1$H NMR (400 MHz, CDCl$_3$) δ: 6.93 (m, 1H), 6.80 (m, 3H), 6.69 (m, 1H), 6.59-6.51 (m, 2H), 4.66 (d, J=28.6 Hz, 1H), 4.19 (m, 1H), 3.98-3.74 (m, 11H), 3.15 (dd, J=21.8, 6.3 Hz, 1H), 2.98 (m, 3H), 2.74-2.47 (m, 5H), 2.12 (s, 2H), 1.74 (m, 3H), 1.53 (m, 8H), 1.26-1.18 (m, 6H), 1.15-1.02 (m, 8H), 0.84 (m, 6H).

LC-MS (ESI) 821 [M+H]+.

Example 12: Preparation of Conjugate A37

Conjugate A37 was prepared according to a method similar to that of Example 11, wherein conjugate A36 was prepared.

$^1$H NMR (400 MHz, CDCl$_3$) δ: 6.99-6.92 (m, 1H), 6.85-6.76 (m, 3H), 6.71-6.50 (m, 3H), 4.68 (d, J=17.8 Hz, 1H), 4.21-4.13 (m, 1H), 3.89 (m, 11H), 3.03-2.46 (m, 9H), 2.13 (s, 1H), 1.80-1.12 (m, 24H), 0.84 (m, 6H).

LC-MS (ESI) 793 [M+H]$^+$.

Example 13: Preparation of Conjugate A38

Conjugate A38 was prepared according to a method similar to that of Example 11, wherein conjugate A36 was prepared.

$^1$H NMR (400 MHz, CDCl$_3$) δ: 8.05 (d, J=8.1 Hz, 2H), 7.42 (d, J=8.1 Hz, 2H), 6.96 (d, J=8.0 Hz, 1H), 6.78-6.58 (m, 4H), 6.43 (s, 1H), 4.59 (s, 1H), 4.09 (dd, J=9.2, 6.5 Hz, 1H), 3.91-3.64 (m, 12H), 2.93 (d, J=4.6 Hz, 2H), 2.75-2.52 (m, 6H), 2.07-1.99 (m, 1H), 1.73-1.23 (m, 16H), 1.14 (d, J=6.1 Hz, 6H), 0.79-0.70 (m, 6H).

LC-MS (ESI) 855 [M+H]$^+$.

Example 14: Preparation of Conjugates A39-A52

Conjugates A39-A52 were prepared according to methods similar to those of Example 10 and Example 11.

| Conjugate No. | LC-MS |
|---|---|
| A39 | 848 [M + H]$^+$ |
| A40 | 808 [M + H]$^+$ |
| A41 | 870 [M + H]$^+$ |
| A42 | 896 [M + H]$^+$ |
| A43 | 900 [M + H]$^+$ |
| A44 | 862 [M + H]$^+$ |
| A45 | 765 [M + H]$^+$ |
| A46 | 753 [M + H]$^+$ |
| A47 | 808 [M + H]$^+$ |
| A48 | 834 [M + H]$^+$ |
| A49 | 881 [M + H]$^+$ |
| A50 | 874 [M + H]$^+$ |
| A51 | 888 [M + H]$^+$ |
| A52 | 578 [M + H]$^+$ |

Example 15: Preparation of Conjugate A53

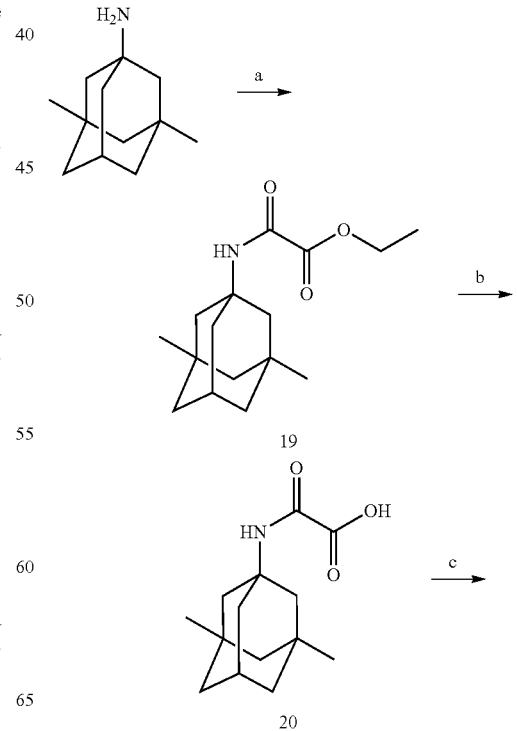

Scheme 7

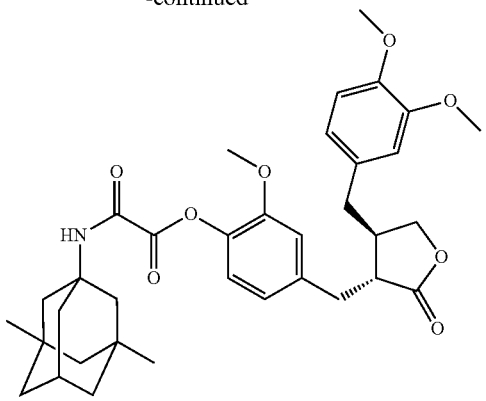

A53

Reaction reagents and conditions: A) monoethyl oxalate, 1-ethyl-(3-dimethylaminopropyl)carbodiimide, 4-dimethylaminopyridine, dichloromethane; b) an aqueous solution of sodium hydroxide, ethanol; c) arctigenin, 1-ethyl-(3-dimethylaminopropyl)carbodiimide, 4-dimethylaminopyridine, dichloromethane.

Step a). Preparation of Compound 19

Monoethyl oxalate (1 equivalent) was dissolved in a suitable amount of dichloromethane, 1-ethyl-(3-dimethylaminopropyl)carbodiimide (1.2 equivalents) and 4-dimethylaminopyridine (5 equivalents) were then added; after the reaction was stirred at room temperature for 15 minutes, memantine (1 equivalent) was added, and the reaction was continued at room temperature overnight. A suitable amount of water was added to the reaction solution, the organic phase was separated, washed with dilute hydrochloric acid, saturated sodium bicarbonate and saturated brine, respectively, dried over sodium sulfate, concentrated, and purified by column chromatography to afford compound 19. LC-MS 280 [M+H]$^+$.

Step b). Preparation of Compound 20

Compound 19 was dissolved in a suitable amount of ethanol, a suitable amount of an aqueous solution of sodium hydroxide was added, and the reaction was stirred at room temperature overnight. The reaction solution was neutralized with dilute hydrochloric acid to acidic, the solid was filtered to afford target product 20, which was directly used in the next reaction without purification. $^1$H NMR (400 MHz, CD$_3$OD) δ: 2.14 (dt, J=6.4, 3.2 Hz, 1H), 1.72 (d, J=1.6 Hz, 2H), 1.52 (q, J=12.4 Hz, 4H), 1.38-1.22 (m, 4H), 1.12 (dd, J=3.6, 2.0 Hz, 2H), 0.87 (s, 6H).

Step c). Preparation of Conjugate A53

Compound 20 (1 equivalent) was dissolved in a suitable amount of dichloromethane, 1-ethyl-(3-dimethylaminopropyl)carbodiimide (1.2 equivalents) and 4-dimethylaminopyridine (5 equivalents) were added; after the reaction was stirred at room temperature for 15 minutes, arctigenin (1 equivalent) was added, and the reaction was continued at room temperature overnight. A suitable amount of water was added to the reaction solution, the organic phase was separated, washed with dilute hydrochloric acid, saturated sodium bicarbonate and saturated brine, respectively, dried over sodium sulfate, concentrated, and purified by column chromatography to afford conjugate A53.

$^1$H NMR (400 MHz, CD$_3$OD) δ: 6.89-6.77 (m, 3H), 6.72-6.57 (m, 3H), 4.82 (t, J=5.5 Hz, 1H), 4.13-4.06 (m, 1H), 3.84 (s, 3H), 3.81 (s, 6H), 2.89-2.70 (m, 4H), 2.57-2.47 (m, 2H), 2.11 (dt, J=6.4, 3.2 Hz, 1H), 1.71 (d, J=1.6 Hz, 2H), 1.50 (q, J=12.4 Hz, 4H), 1.36-1.21 (m, 4H), 1.12 (dd, J=3.6, 2.0 Hz, 2H), 0.83 (s, 6H).

Example 16: Preparation of Conjugate A54

Conjugate A54 was prepared according to a method similar to that of Example 15.

$^1$H NMR (400 MHz, CD$_3$OD) δ: 6.89-6.78 (m, 3H), 6.73-6.58 (m, 3H), 4.83 (t, J=5.5 Hz, 1H), 4.15-4.07 (m, 1H), 3.84 (s, 3H), 3.82 (s, 6H), 3.52 (s, 2H), 2.90-2.71 (m, 4H), 2.58-2.47 (m, 2H), 2.13 (dt, J=6.4, 3.2 Hz, 1H), 1.72 (d, J=1.6 Hz, 2H), 1.51 (q, J=12.4 Hz, 4H), 1.36-1.22 (m, 4H), 1.12 (dd, J=3.6, 2.0 Hz, 2H), 0.84 (s, 6H).

Example 17: Preparation of Conjugate A55

Synthetic Scheme 8

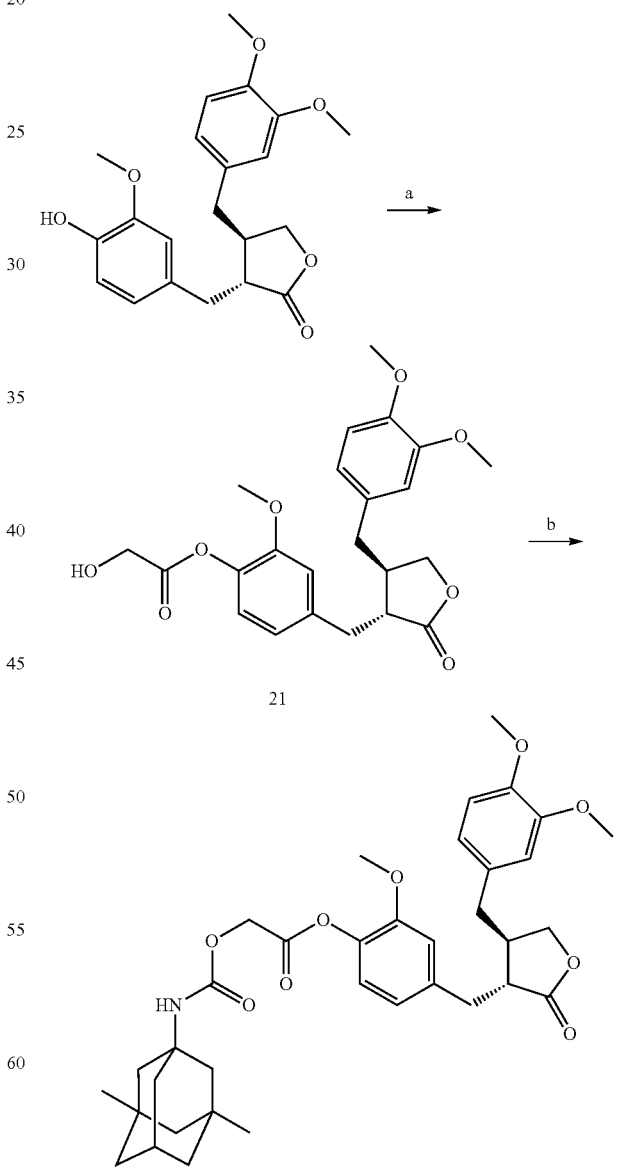

A55

Reaction reagents and conditions: a) hydroxyacetic acid, 1-ethyl-(3-dimethylaminopropyl)carbodiimide, triethylamine, dichloromethane; b) triethylamine, tetrahydrofuran.

Step a). Preparation of Compound 21

Hydroxyacetic acid (1 equivalent) was dissolved in a suitable amount of dichloromethane, 1-ethyl-(3-dimethylaminopropyl)carbodiimide (1.2 equivalents) and triethylamine (1.2 equivalents) were added; after the reaction was stirred at room temperature for 5 minutes, arctigenin (1.1 equivalents) was added, and the reaction was continued at room temperature overnight. A suitable amount of water was added to the reaction solution, the organic phase was separated, washed with dilute hydrochloric acid, saturated sodium bicarbonate and saturated brine, respectively, dried over sodium sulfate, concentrated, and purified by column chromatography to afford compound 21.

LC-MS 430 [M−H]−.

Step b). Preparation of Conjugate A55

Compound 1 (1 equivalent) obtained in Step a) of Example 1 was dissolved in dry tetrahydrofuran, and compound 21 (0.8 equivalents) and triethylamine (1 equivalent) were added. The reaction was performed at 50° C. for 24 hours, and after TLC indicated disappearance of compound 21, the reaction solution was concentrated to obtain a product, which was purified by column chromatography to afford conjugate A55.

$^1$H NMR (400 MHz, CD$_3$OD) δ: 6.87-6.76 (m, 3H), 6.72-6.57 (m, 3H), 5.02 (s, 2H), 4.81 (t, J=5.5 Hz, 1H), 4.14-4.06 (m, 1H), 3.83 (s, 3H), 3.81 (s, 6H), 2.88-2.70 (m, 4H), 2.54-2.46 (m, 2H), 2.11 (dt, J=6.4, 3.2 Hz, 1H), 1.71 (d, J=1.6 Hz, 2H), 1.50 (q, J=12.4 Hz, 4H), 1.34-1.21 (m, 4H), 1.10 (dd, J=3.6, 2.0 Hz, 2H), 0.82 (s, 6H).

Biological Assays:

Test Example 1

The effect of Conjugate A04 on Rescuing the Memory Impairment in *Drosophila* AD Model A *drosophila* Alzheimer's disease model wherein humanized A342 was overexpressed (the model *drosophila* has significant learning and memory defects), was employed in the present invention to evaluate the effect of conjugate A04 in rescuing the learning and memory ability of the model *drosophila*.

1. Experimental Principle

Pavlovian olfactory memory platform was improved from the literatures (see Tully, T. et al., Classical conditioning and retention in normal and mutant *Drosophila melanogaster*. (1985) J. Comp. Physiol. A 157: 263-277; Tully, T. et al., Genetic dissection of consolidated memory in *Drosophila*. (1994) Cell 79: 35-47; Yin, J. C. et al., Induction of a dominant negative CREB transgene specifically blocks long-term memory in *Drosophila*. (1994) Cell 79: 49-58). The learning and memory test was performed in a behavior room having a constant temperature and humidity (25° C. and 70% relative humidity). The test comprises two stages:

training stage: about a hundred drosophilas were placed into a training tube covered with copper net inside, and the drosophilas sequentially smelt two odors (octanol (OCT) and methylcyclohexanol (MCH)). Each odor lasted for 1 minute, and after each of the odors, 45 seconds of fresh air were passed through. The drosophilas were subjected to 1 minute of electric shock only when it smelt the first odor. Such a set of procedures constituted a training cycle. In order to avoid the natural preference of the drosophilas for odors, one tube of the drosophilas smelt OCT first and then received an electric shock at each data point, while the other tube of the drosophilas smelt MCH first and then received an electric shock, and the mean value of the test results of the 2 tubes of drosophilas was a data point.

test stage: the drosophilas were immediately transferred to the selection point of a T-maze after the training, and then they were made to choose between the containers of the two odors within two minutes. After 2 minutes, the numbers of drosophilas in different containers were respectively counted, and the performance index (PI) was calculated. If the drosophilas in the two containers are in a ratio of 50:50, then PI=0, indicating that the drosophilas cannot remember the relationship between the electric shock and the odor; while PI=100 means that 100% of the drosophilas remembered the relationship between the odor and the electric shock, and would avoid electric shock according to the odor information.

2. Experimental Materials and Method

1) *Drosophila* Strain

All the drosophilas used in this experiment were backcrossed for at least 5 generations so that they were all in the genetic background of w1118 (isoCJ1) to avoid the influence of different genetic backgrounds on the results. Therefore, w1118 (isoCJ1) strain drosophilas (referred to as "2U") were the original control group of all experiments. In order to avoid potential adverse effects on the *drosophila* strain caused by long-term, cross-generation expression of A342 protein, drosophilas which contains a regulatable humanized A342 gene (referred to as "H29.3") was used, and only when it hybridizes with elav-GAL4c155 (referred to as "P35"), which initiates A342 gene expression, does its progeny generation expresses A342 protein in the nervous system. The progeny *drosophila* obtained by hybridization between H29.3 and the genetic background *drosophila*, 2U, did not express A342 protein, and was used as a genetic control group.

The learning test was conducted on the above-mentioned progeny generation. The drosophilas used in this test example were obtained according to FIG. 1.

2) *Drosophila* Feeding, Administration and Testing

The parent drosophilas were kept in a standard environment of 24° C., 40-60% relative humidity and 12 hours light per day. On the day after eclosion (DAE 2) of progeny drosophilas, control male drosophilas (+/Y; UAS-Aβ4/+) and the male drosophilas in the test group (elav/Y; UAS-Aβ42/+) were selected under a microscope, 100 per tube. The selected drosophilas were transferred to a condition of 29° C., 40±15% relative humidity for subsequent feeding and drug treatment.

The conjugate stock solution and the control compound memantine (Mem) (10 mM) were both stored in a −20° C. freezer. On the day before the start of the administration, the stock solution was diluted to 100 μM in a 4% sucrose working solution, and stored in a −20° C. freezer. The sucrose working solution has no effect on the learning and memory ability of the drosophilas. From day 2 to day 8 (7 days in total), each group of the drosophilas was administered for 4 hours per day, and rested for 20 hours in the presence of fresh food. Each tube of the drosophilas was administered with 50 μl of the drug or a control compound per day through a device for administering to drosophilas.

Then the rescue effect of the compound on the memory impairment of drosophilas was detected by the Pavlovian olfactory memory method. 7 data points were obtained for each drug, and each data point was the mean value of the olfactory memory of the 2 tubes of drosophilas.

3. Experimental Results

Figure 2:
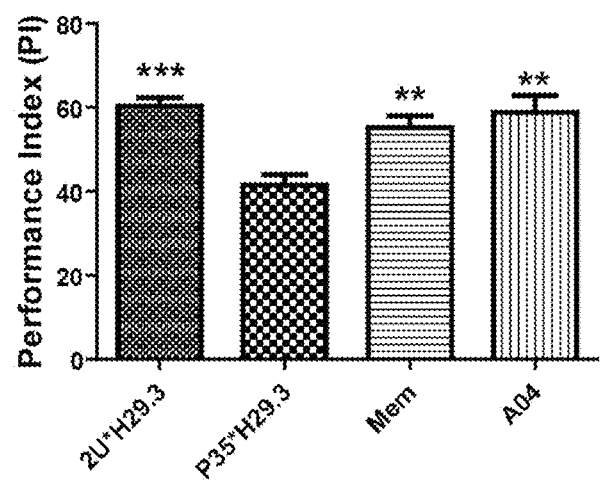
FIG. 2 shows the effects of memantine (Mem) and conjugate A04 on rescuing the memory impairment in AD drosophilas.

2U*H29.3 is the genetic control group (healthy drosophilas), P35*H29.3 is the AD control group (only solvent was administered, i.e., negative control). Mem and conjugate A04 are the data obtained after feeding a corresponding drug in the AD experiment. The results of each drug contain 7 data points, which belong to three independent experiments. Among them, the PI of the AD negative control group is 41 (the requirement is less than 45), the difference in PI between the genetic control group and the AD negative group is 19 (the requirement is more than 15), the PI of the positive drug Mem is 55, and the rescue effect is more than 50% (the rescue effect of the negative control group is 0%, and that of the genetic control group is 100%), all the above meet the standard for the experiment to be valid. The experimental data are shown in FIG. 2. The data show that conjugate A04 has a better rescue effect on the memory impairment of AD drosophilas than Mem (using T-test Statistical method, corresponding to the AD model *drosophila* group; *, $p<0.05$; , $p<0.01$; *, $p<0.001$).

Test Example 2

The Effect of Conjugate A04 on Reversing Memory Impairment of APP/PS1 Transgenic AD Model Mice.

In the present invention, conjugate A04 was administered by gastric gavage to APP/PS1 transgenic AD model mice, and then the effect of conjugate A04 on the memory impairment of transgenic AD model mice was detected through the classic Morris water maze test.

1. Experimental Principle

In this experiment, APP/PS1 double transgenic AD model mice, which developed Aβ deposition when they were about 6 months old, and had impairment on the space memory when they were about 7 months old, were employed. Therefore, in this experiment, the impairment on the space memory of the mice was further detected via the water maze test, and at the same time, whether conjugate A04 has a therapeutic or improving effect on the memory impairment was evaluated.

2. Experimental Materials and Method

1) Identification of APP/PS1 double transgenic AD model mice: the mice's tail was snipped off, then the gene sequence of APP/PS1 in mice was identified by PCR. The wild type C57 (B6C3) mice were used as the negative control mice. The mice were housed under standard conditions (12/12 hours bright and dark cycle, enough water and food, constant temperature at 22° C. and 60% humidity).

2) Administration to the transgenic AD model mice: 30 transgenic AD model mice were randomly divided into 3 groups when the mice were 6 months old (Control-AD: transgenic solvent group; A04: a group wherein 50 mg/kg conjugate A04 was administered to the transgenic mice; Mem: a group wherein 50 mg/kg memantine hydrochloride was administered to the transgenic mice), and 10 non-transgenic mice were employed as the negative control group (Control-WT). Conjugate A04 and memantine hydrochloride were dissolved by 0.9% NaCl+0.5% Tween 80, and were administered by gastric gavage for 60 days before conducting the Morris water maze test.

3) Morris water maze test: a mixture of water and fresh milk at a temperature of 19-20° C. was injected into a white round pool with a diameter of 120 centimeters daily in the test. A round platform with a diameter of 15 centimeters was placed at the center of a certain quadrant of a round four quadrants, and the platform was below the surface of the water by 2 centimeters. Markers in different shapes were pasted on the superior wall of the four quadrants of the pool, and they can provide clues for the mice to locate the position of the platform below water via the markers. At day zero of the test (i.e., the adaptation period), if the mice failed to find the platform within 60 seconds, the mice would need to be manually placed on the platform for 5 seconds to help the mice recognize the existence and position of the platform. During the first to eighth days of the test, each mouse was made to swim 4 times a day to let it search the platform. The interval time was the same (1 hour to 2 hours). If a mouse failed to find the platform within 60 seconds, then it was recognized that the time of searching the platform of the mouse was 60 seconds. The motion track and speed of the mice were automatically recorded by Anymaze and the matched camera. The average time of searching the platform in the four tests per day was recorded as the time for searching the platform on that day (latent period). All the animal experimental operations were under strict adherence to the Laboratory Animal Management Regulations.

3. Experimental Results

Figure 3:
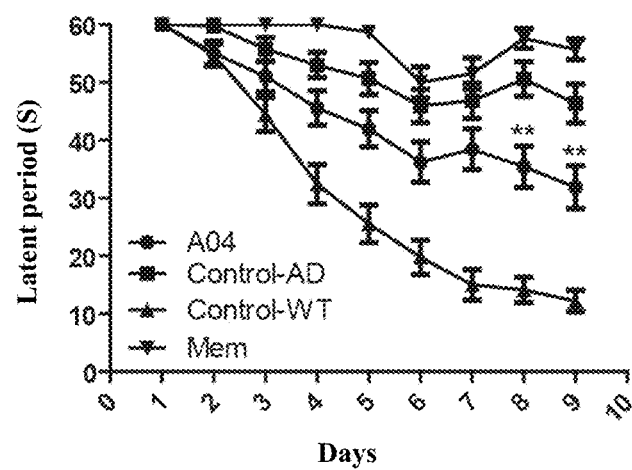
FIG. 3 shows the effect of conjugate A04 on reversing memory impairment of transgenic AD model mice.

In FIG. 3, A04 represents the administration group of transgenic AD model mice (the dose of conjugate A04 was 50 mg/kg/day); Control-Ad represents the solvent group of transgenic AD model mice (0.9% NaCl+0.5% Tween 80); Control-Wt represents the solvent group of non-transgenic mice (0.9% NaCl+0.5% Tween 80), Mem represents the group administered memantine hydrochloride of transgenic AD model mice (the dose of memantine hydrochloride was 50 mg/kg/day). The test results of the latent period in the Morris water maze test show that: the latent period of transgenic AD model mice was significantly longer than that of non-transgenic mice; the latent period of the transgenic AD model mice administered with conjugate A04 (50 mg/kg/day) for 60 days was significantly shorter than that of the transgenic mice treated with the solvent. The above test results indicate that the transgenic AD model mice have memory impairment, while conjugate A04 can significantly improve the memory impairment of the transgenic mice. The latent period of the memantine hydrochloride administered group has no significant change compared with that of the transgenic AD model mice, indicating memantine hydrochloride does not have the effect of reversing the memory impairment of the transgenic AD mice.

This test shows that conjugate A04 has the effect of reversing memory impairment of transgenic AD model mice, while memantine hydrochloride cannot reverse memory impairment of transgenic AD model mice.

Test Example 3

This test investigated the pharmacokinetics of arctigenin (ATG) and conjugate A04 in rats. The rats were administered by gastric gavage with ATG and A04, the whole blood sample was collected at various time points, the plasma was separated, and the concentration of ATG in plasma was determined by LC-MS.

1. Experimental Protocol 6 healthy SD rats, male, 200-220 g, and the dosing regimen is shown in the table below:

| group | Number of animals | compound | Administration route | Dosage (mg/kg) | dose volume (ml/kg) |
|---|---|---|---|---|---|
| 1 | 3 | A04 | gastric gavage | 20 | 10 |
| 2 | 3 | ATG | gastric gavage | 20 | 10 |

Before the test, the rats were fasted for 12 hours, with free access to water, and were fed 2 hours after administration.

Blood sampling time points: 0.5, 1.0, 2.0, 4.0, 6.0, 8.0 and 12 h after administration by gastric gavage.

0.5 mL venous blood was taken from the posterior venous plexus of the rat's eyeball at the above set time points, put in a heparinized tube, centrifuged for 5 min at 11000 rpm to separate the plasma, and froze in a refrigerator at −20° C.

200 μL acetonitrile was added into 100 μL plasma samples, vortex mixed for 1 min, and centrifuged for 5 min at 11000 rpm; all the supernatant was taken out and put in a 10 mL test tube, dried in an airflow at 40° C., dissolved in 100 μL acetonitrile-water (1:9, v/v), and 10 μL was taken for UPLC/Q-TOF MS analysis.

2. Results

After the rats were administered by gastric gavage with 20 mg/kg ATG, no ATG was detected in the plasma (the plasma concentration was lower than the lower detection limit of 1.0 ng/ml).

After the rats were administered by gastric gavage with 20 mg/kg conjugate A04, the ATG plasma concentration (ng/mL) in rats is as shown in Table 1.

TABLE 1

| animal No. | time (h) | | | | | | |
|---|---|---|---|---|---|---|---|
| | 0.5 | 1.0 | 2.0 | 4.0 | 6.0 | 8.0 | 12.0 |
| 1 | 1.58 | 3.58 | 7.89 | 12.58 | 28.74 | 15.87 | 6.97 |
| 2 | 2.57 | 1.35 | 12.54 | 18.65 | 36.24 | 10.14 | 5.34 |
| 3 | 3.57 | 2.87 | 8.97 | 15.89 | 25.47 | 13.21 | 4.67 |

Although the present invention has been further described through the above specific examples, it should be understood that it is not limited thereby. The present invention encompasses general aspects of the above disclosures, and a person skilled in the art is able to make various modifications or change various details of the present invention without departing from the spirit and scope of the present invention. Thus, the present description is presented for purposes of illustration only and not by way of limitation.

What is claimed is:

1. A conjugate comprising a compound of formula (I), or a pharmaceutically acceptable salt, stereoisomer, polymorph, or solvate thereof:

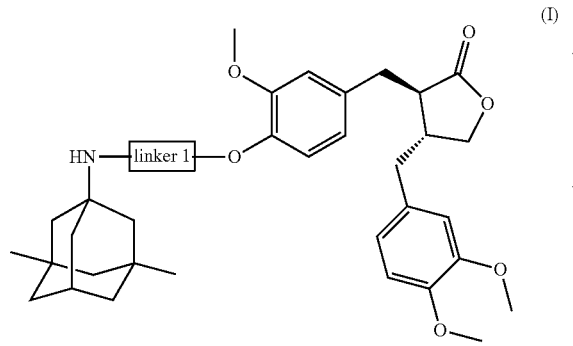
(I)

wherein:
Linker 1 is selected from the group consisting of —C(O)—, —C(O)L$_1$C(O)—, —C(O)OL$_1$C(O)—, —C(O)OL$_1$OC(O)—, —C(O)OQ$_1$L$_2$Q$_2$-, —C(O)Q$_1$L$_2$Q$_2$N(R$_1$)C(O)—, —C(O)Q$_1$L$_2$Q$_2$OC(O)—, —C(O)Q$_1$L$_2$Q$_2$C(O)—, —C(O)OQ$_1$L$_2$Q$_2$OC(O)—, —C(O)OQ$_1$L$_2$Q$_2$N(R$_1$)C(O)—, —C(O)OQ$_1$L$_2$Q$_2$N(R$_1$)C(O)— and —C(O)OQ$_1$L$_2$Q$_2$C(O)—;

L$_1$ is a direct bond, or is selected from the group consisting of —O—, —S—, —NR$_2$—, substituted or unsubstituted C1-C6 straight or branched alkylene, substituted or unsubstituted C2-C6 straight or branched alkenylene, substituted or unsubstituted C2-C6 straight or branched alkynylene, substituted or unsubstituted C3-C10 cyclrejectionlkylene, substituted or unsubstituted C3-C10 non-aromatic heterocyclylene, substituted or unsubstituted C6-C14 arylene, substituted or unsubstituted C6-C14 heterrectionrylene, and substituted or unsubstituted C6-C20 aralkylene;

L$_2$ is a direct bond, or is selected from the group consisting of —NR$_2$—, —O—, —C(O)—, —N(R$_3$)C(O)—, —C(O)N(R$_3$)—, —C(O)O—, —OC(O)—, —N(R$_3$)Q$_3$O—, —N(R$_3$)C(O)Q$_3$O—, —N(R$_3$)C(O)Q$_3$C(O)—, —N(R$_3$)C(O)Q$_3$N(R$_3$)—, —N(R$_3$)C(O)Q$_3$C(O)N(R$_3$)—, —N(R$_3$)C(O)Q$_3$N(R$_3$)C(O)—, —N(R$_3$)C(O)Q$_3$C(O)O—, —N(R$_3$)C(O)Q$_3$OC(O)—, —C(O)N(R$_3$)Q$_3$C(O)N(R$_3$)—, —C(O)N(R$_3$)Q$_3$C(O)O—, —C(O)N(R$_3$)Q$_3$N(R$_3$)C(O)—, —C(O)N(R$_3$)Q$_3$OC(O)—, —N(R$_3$)Q$_3$C(O)N(R$_3$)—, —N(R$_3$)Q$_3$C(O)O—, —N(R$_3$)Q$_3$N(R$_3$)C(O)—, —N(R$_3$)Q$_3$OC(O)—, —OQ$_3$N(R$_3$)—, —OQ$_3$C(O)N(R$_3$)—, —OQ$_3$C(O)O—, —OQ$_3$N(R$_3$)C(O)—, —OQ$_3$OC(O)—, —OC(O)Q$_3$-, —OC(O)Q$_3$C(O)N(R$_3$)—, —OC(O)Q$_3$C(O)O—, —OC(O)Q$_3$N(R$_3$)—, —OC(O)Q$_3$N(R$_3$)C(O)—, —OC(O)Q$_3$N(R$_3$)L$_1$O—, —OC(O)Q$_3$OC(O)—, —C(O)OQ$_3$-, —C(O)OQ$_3$O—, —C(O)OQ$_3$C(O)N(R$_3$)—, —C(O)OQ$_3$C(O)O—, —C(O)OQ$_3$N(R$_3$)C(O)— or —C(O)OQ$_3$OC(O)—;

Q$_1$, Q$_2$ and Q$_3$ are each independently selected from the group consisting of substituted or unsubstituted C1-C6 straight or branched alkylene, substituted or unsubstituted C3-C10 cyclrejectionlkylene, substituted or unsubstituted C2-C6 straight or branched alkenylene, substituted or unsubstituted C2-C6 straight or branched alkynylene, substituted or unsubstituted C3-C10 non-aromatic heterocyclylene, substituted or unsubstituted C6-C14 arylene, substituted or unsubstituted C6-C14 heterrejectionrylene, and substituted or unsubstituted C6-C20 aralkylene; and R$_1$, R$_2$ and R$_3$ are each independently selected from the group consisting of H and C1-C6 alkyl.

2. The conjugate according to claim 1, which is a compound of formula (II), or a pharmaceutically acceptable salt, stereoisomer, polymorph, or solvate thereof:

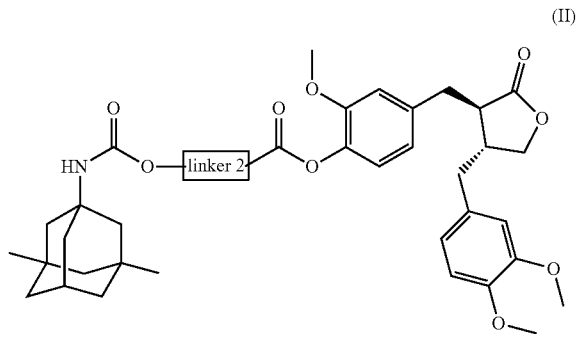
(II)

wherein:
Linker 2 is selected from the group consisting of -L$_1$-, -L$_1$O—, -Q$_1$L$_1$Q$_2$N(R$_1$)—, -Q$_1$L$_2$Q$_2$N(R$_1$)—, -Q$_1$L$_2$Q$_2$O— or -Q$_1$L$_2$Q$_2$-;

L$_1$ is selected from the group consisting of substituted or unsubstituted C1-C6 straight or branched alkylene, substituted or unsubstituted C2-C6 straight or branched alkenylene, substituted or unsubstituted C2-C6 straight or branched alkynylene, substituted or unsubstituted C3-C10 cyclrejectionlkylene, substituted or unsubstituted C3-C10 non-aromatic heterocyclylene, substituted or unsubstituted C6-C14 arylene, substituted or unsubstituted C6-C14 heterrejectionrylene, and substituted or unsubstituted C6-C20 aralkylene; and L$_2$, Q$_1$, Q$_2$, Q$_3$, R$_1$, R$_2$ and R$_3$ are as defined in claim 1.

3. The conjugate according to claim 2, which is a compound of formula (III), or a pharmaceutically acceptable salt, stereoisomer, polymorph, or solvate thereof:

(III)

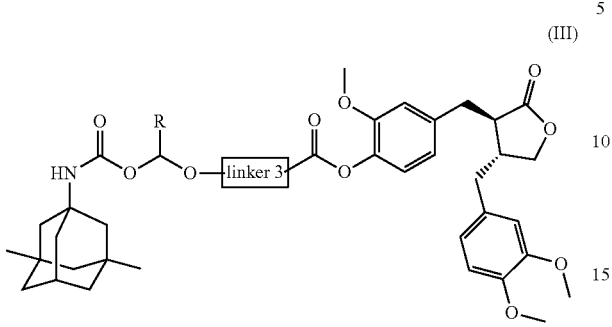

Linker 3 is a direct bond, or is selected from the group consisting of —C(O)$Q_3$N($R_3$)$Q_2$-, —C(O)$Q_3$N($R_3$)$Q_2$N($R_1$)—, —C(O)$Q_2$O—, —C(O)$Q_2$N($R_1$)—, —C(O)$Q_3$N($R_3$)$L_1$O$Q_2$N($R_1$)— and —C(O)$Q_3$$Q_2$N($R_1$)—;

$L_1$, $Q_2$, $Q_3$, $R_1$ and $R_3$ are as defined in claim 2; and

R is selected from the group consisting of H or C1-C6 alkyl.

4. The conjugate according to claim 1, which is selected from the group consisting of conjugates A01 to A55 and pharmaceutically acceptable salts, stereoisomers, polymorphs, and solvates thereof:

| No. | Conjugate Structure |
|---|---|
| A01 | 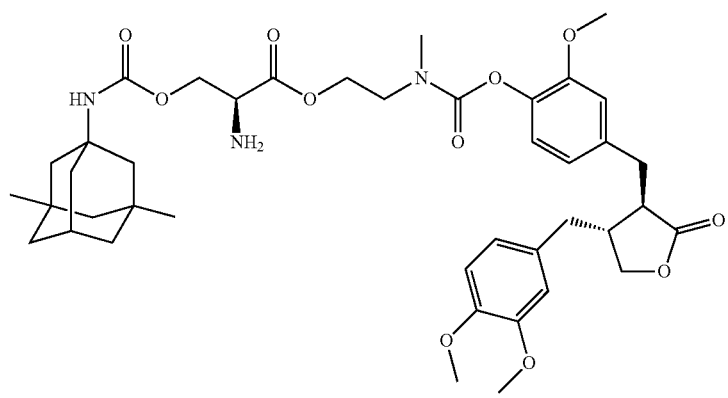 [SMILES: COc1ccc(C[C@H]2COC(=O)[C@@H]2Cc2ccc(OC(=O)N(C)CCOC(=O)[C@@H](N)COC(=O)NC34CC5CC(C)(CC(C)(C5)C3)C4)c(OC)c2)cc1OC] |
| A02 | 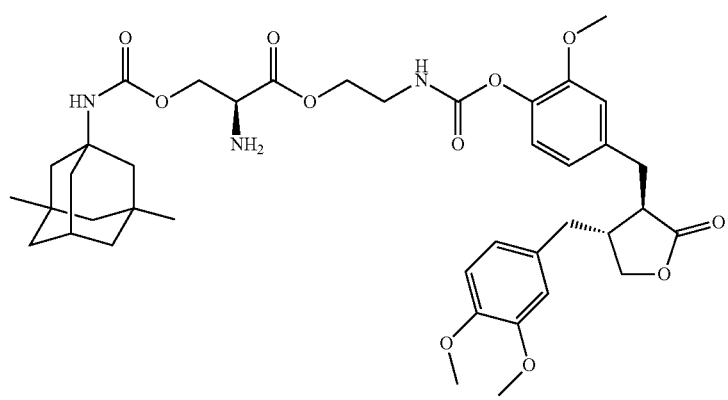 [SMILES: COc1ccc(C[C@H]2COC(=O)[C@@H]2Cc2ccc(OC(=O)NCCOC(=O)[C@@H](N)COC(=O)NC34CC5CC(C)(CC(C)(C5)C3)C4)c(OC)c2)cc1OC] |

| No. | Conjugate Structure |
|---|---|
| A03 | 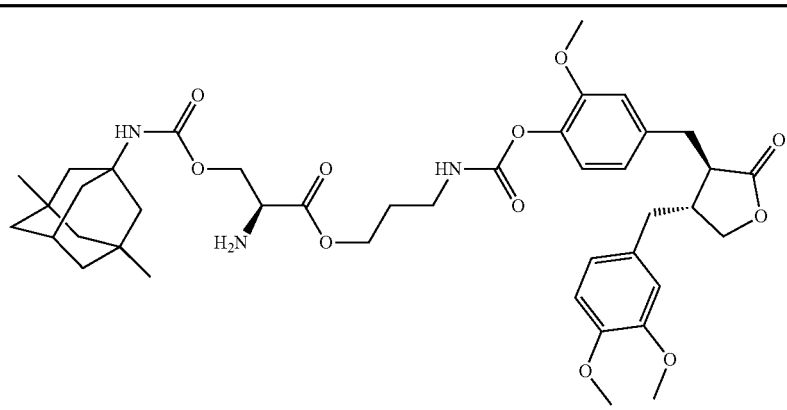 |
| A04 | 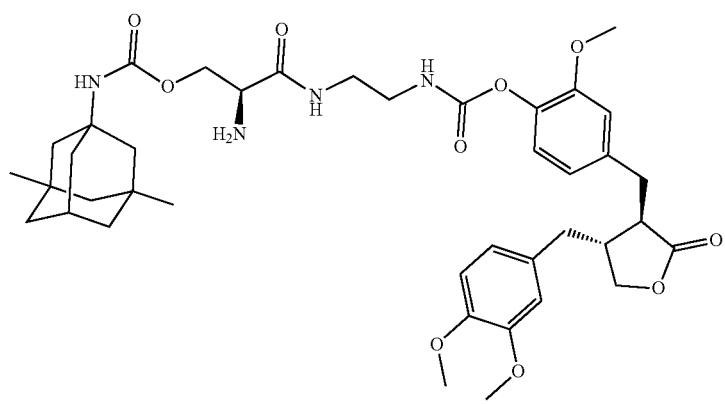 [SMILES: COc1ccc(C[C@H]2COC(=O)[C@@H]2Cc2ccc(OC(=O)NCCNC(=O)[C@@H](N)COC(=O)NC34CC5CC(C)(CC(C)(C5)C3)C4)c(OC)c2)cc1OC] |
| A05 | 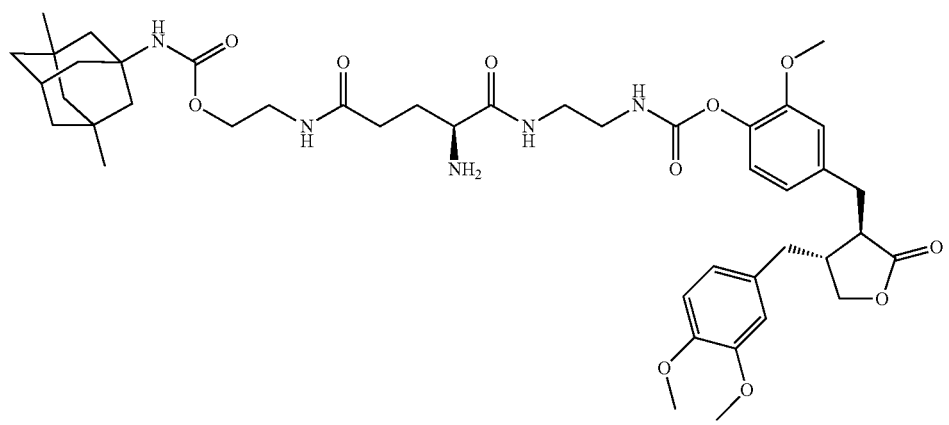 [SMILES: COc1ccc(C[C@H]2COC(=O)[C@@H]2Cc2ccc(OC(=O)NCCNC(=O)[C@@H](N)CCC(=O)NCCOC(=O)NC34CC5CC(C)(CC(C)(C5)C3)C4)c(OC)c2)cc1OC] |

| No. | Conjugate Structure |
|---|---|
| A06 | 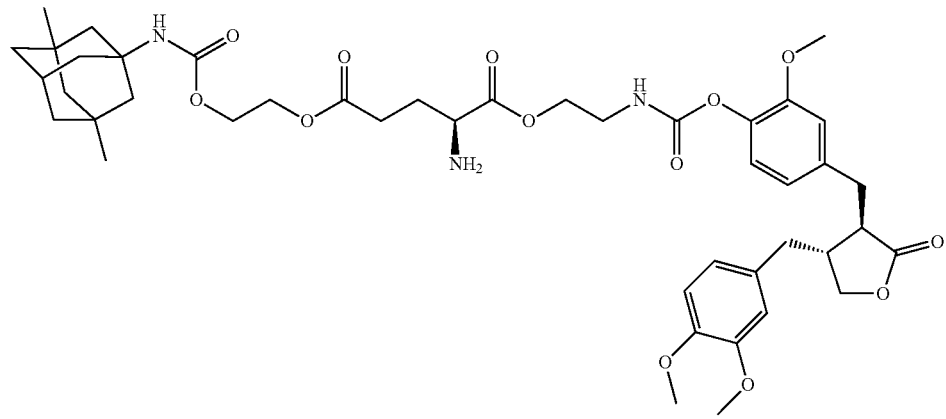 [SMILES: COc1ccc(C[C@H]2COC(=O)[C@@H]2Cc2ccc(OC(=O)NCCOC(=O)[C@@H](N)CCC(=O)OCCOC(=O)NC34CC5CC(C)(CC(C)(C5)C3)C4)c(OC)c2)cc1OC] |
| A07 | 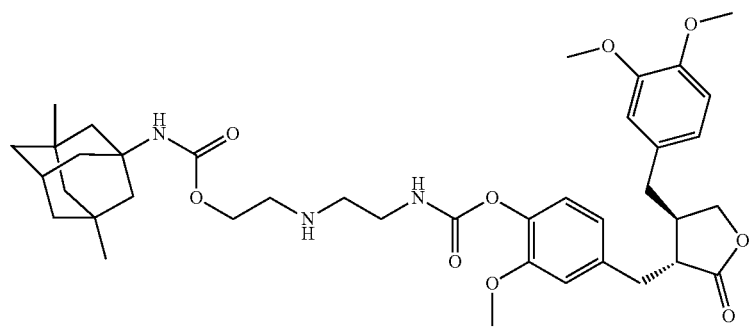 [SMILES: COc1ccc(C[C@H]2COC(=O)[C@@H]2Cc2ccc(OC(=O)NCCNCCOC(=O)NC34CC5CC(C)(CC(C)(C5)C3)C4)c(OC)c2)cc1OC] |
| A08 | 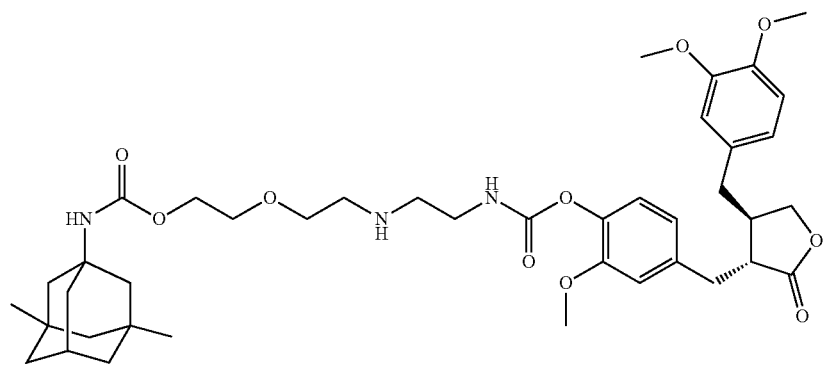 [SMILES: COc1ccc(C[C@H]2COC(=O)[C@@H]2Cc2ccc(OC(=O)NCCNCCOCCOC(=O)NC34CC5CC(C)(CC(C)(C5)C3)C4)c(OC)c2)cc1OC] |
| A09 | 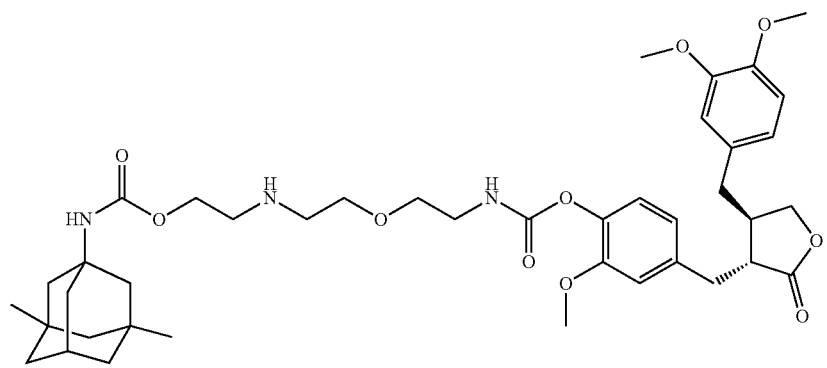 [SMILES: COc1ccc(C[C@H]2COC(=O)[C@@H]2Cc2ccc(OC(=O)NCCOCCNCCOC(=O)NC34CC5CC(C)(CC(C)(C5)C3)C4)c(OC)c2)cc1OC] |

| No. | Conjugate Structure |
|---|---|
| A10 | 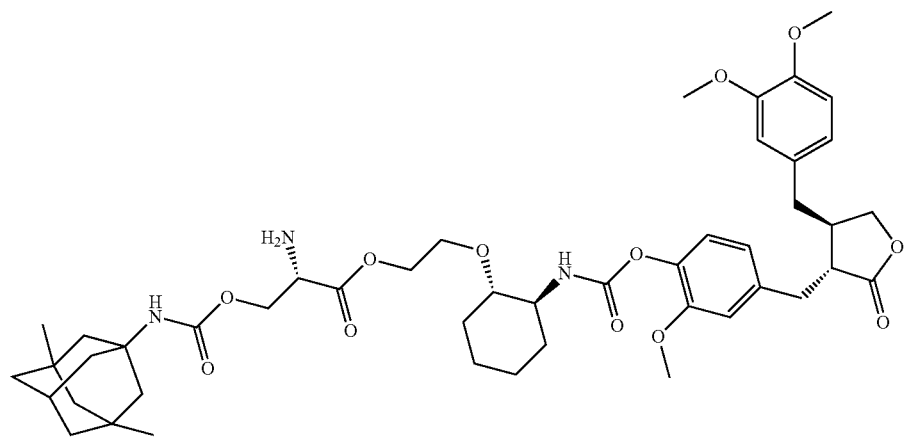 [SMILES: COc1ccc(C[C@H]2COC(=O)[C@@H]2Cc2ccc(OC(=O)N[C@H]3CCCC[C@@H]3OCCOC(=O)[C@@H](N)COC(=O)NC34CC5CC(C)(CC(C)(C5)C3)C4)c(OC)c2)cc1OC] |
| A11 | 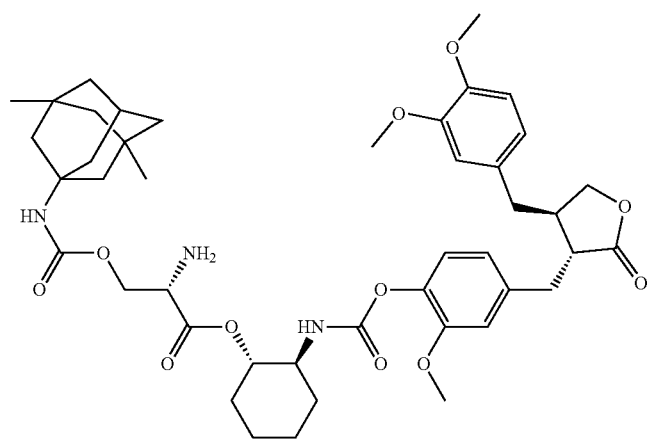 [SMILES: COc1ccc(C[C@H]2COC(=O)[C@@H]2Cc2ccc(OC(=O)N[C@H]3CCCC[C@@H]3OC(=O)[C@@H](N)COC(=O)NC34CC5CC(C)(CC(C)(C5)C3)C4)c(OC)c2)cc1OC] |
| A12 | 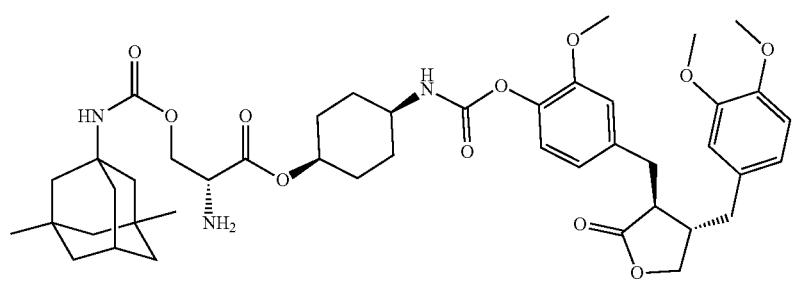 [SMILES: COc1ccc(C[C@@H]2COC(=O)[C@H]2Cc2ccc(OC(=O)N[C@H]3CC[C@@H](OC(=O)[C@H](N)COC(=O)NC45CC6CC(C)(CC(C)(C6)C4)C5)CC3)c(OC)c2)cc1OC] |
| A13 | 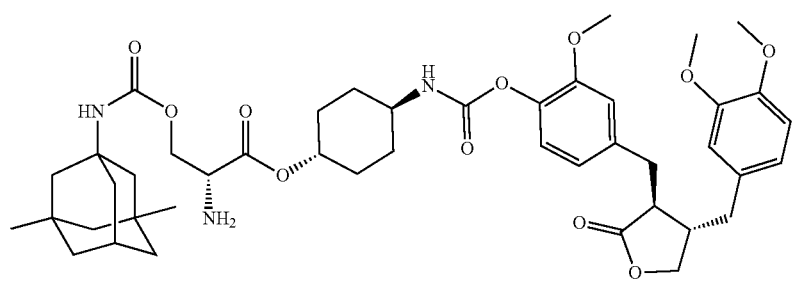 [SMILES: COc1ccc(C[C@@H]2COC(=O)[C@H]2Cc2ccc(OC(=O)N[C@H]3CC[C@H](OC(=O)[C@H](N)COC(=O)NC45CC6CC(C)(CC(C)(C6)C4)C5)CC3)c(OC)c2)cc1OC] |

| No. | Conjugate Structure |
|---|---|
| A14 | 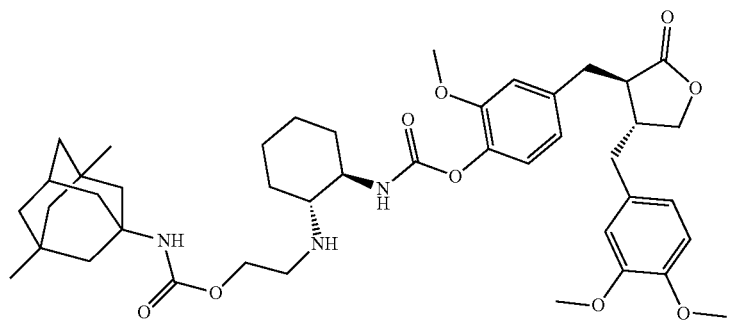 |
| A15 | 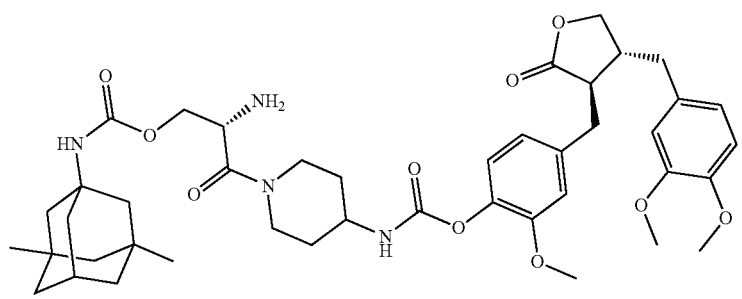 [SMILES: COc1ccc(C[C@H]2COC(=O)[C@@H]2Cc2ccc(OC(=O)NC3CCN(C(=O)[C@@H](N)COC(=O)NC45CC6CC(C)(CC(C)(C6)C4)C5)CC3)c(OC)c2)cc1OC] |
| A16 | 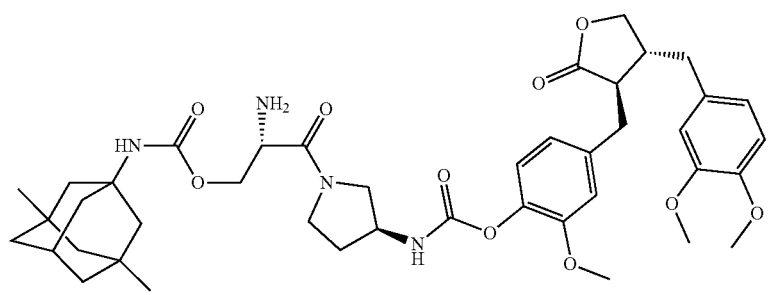 [SMILES: COc1ccc(C[C@H]2COC(=O)[C@@H]2Cc2ccc(OC(=O)N[C@H]3CCN(C(=O)[C@@H](N)COC(=O)NC45CC6CC(C)(CC(C)(C6)C4)C5)C3)c(OC)c2)cc1OC] |
| A17 | 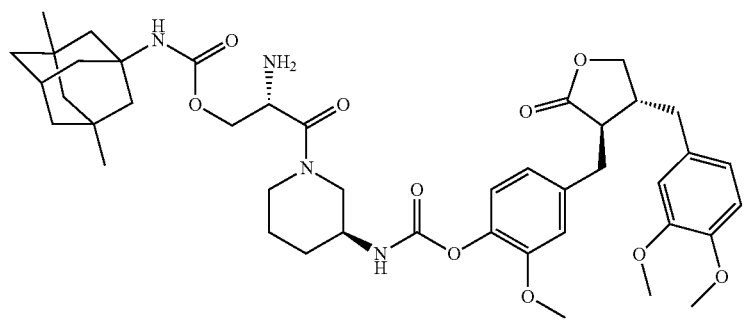 [SMILES: COc1ccc(C[C@H]2COC(=O)[C@@H]2Cc2ccc(OC(=O)N[C@H]3CCCN(C(=O)[C@@H](N)COC(=O)NC45CC6CC(C)(CC(C)(C6)C4)C5)C3)c(OC)c2)cc1OC] |
| A18 | 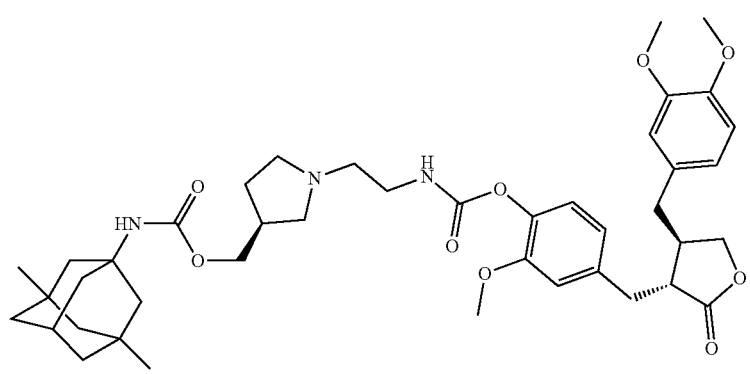 [SMILES: COc1ccc(C[C@H]2COC(=O)[C@@H]2Cc2ccc(OC(=O)NCCN3CC[C@H](COC(=O)NC45CC6CC(C)(CC(C)(C6)C4)C5)C3)c(OC)c2)cc1OC] |

-continued
| No. | Conjugate Structure |
|---|---|
| A19 | 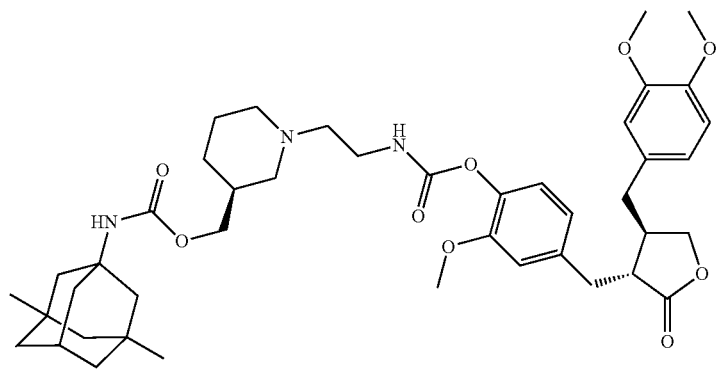 [SMILES: COc1ccc(C[C@H]2COC(=O)[C@@H]2Cc2ccc(OC(=O)NCCN3CCC[C@H](COC(=O)NC45CC6CC(C)(CC(C)(C6)C4)C5)C3)c(OC)c2)cc1OC] |
| A20 | 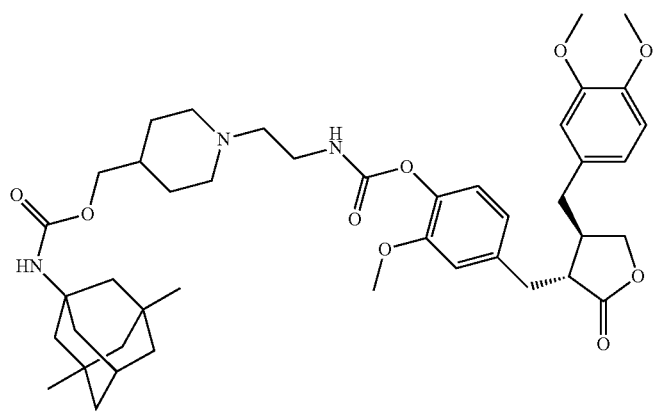 [SMILES: COc1ccc(C[C@H]2COC(=O)[C@@H]2Cc2ccc(OC(=O)NCCN3CCC(COC(=O)NC45CC6CC(C)(CC(C)(C6)C4)C5)CC3)c(OC)c2)cc1OC] |
| A21 | 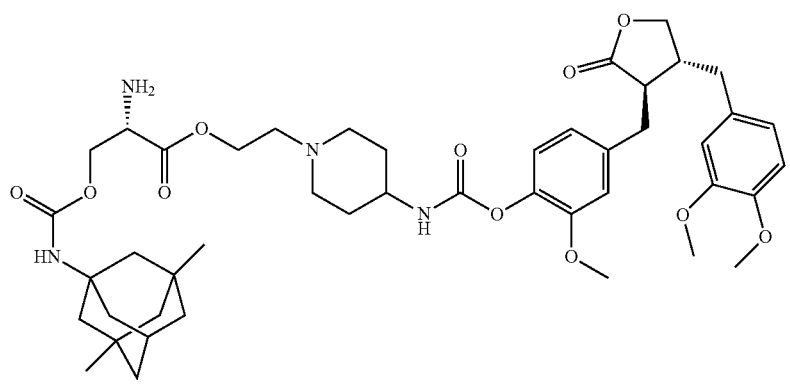 [SMILES: COc1ccc(C[C@H]2COC(=O)[C@@H]2Cc2ccc(OC(=O)NC3CCN(CCOC(=O)[C@@H](N)COC(=O)NC45CC6CC(C)(CC(C)(C6)C4)C5)CC3)c(OC)c2)cc1OC] |
| A22 | 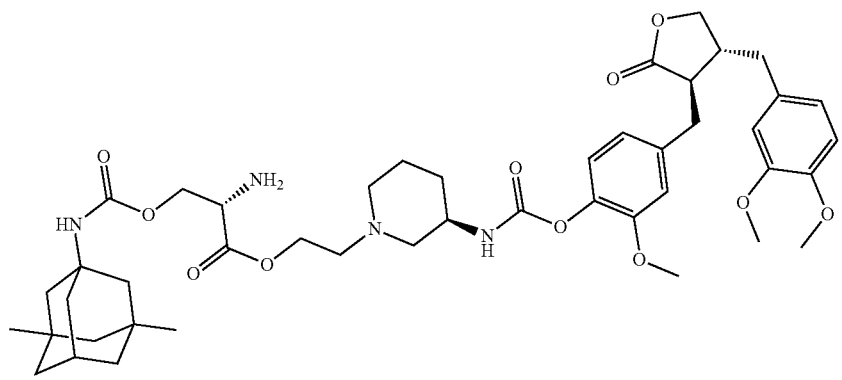 [SMILES: COc1ccc(C[C@H]2COC(=O)[C@@H]2Cc2ccc(OC(=O)N[C@@H]3CCCN(CCOC(=O)[C@@H](N)COC(=O)NC45CC6CC(C)(CC(C)(C6)C4)C5)C3)c(OC)c2)cc1OC] |

| No. | Conjugate Structure |
|---|---|
| A23 | 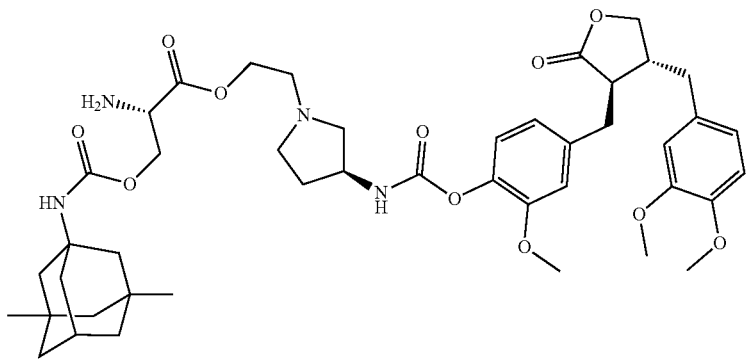 [SMILES: COc1ccc(C[C@H]2COC(=O)[C@@H]2Cc2ccc(OC(=O)N[C@H]3CCN(CCOC(=O)[C@@H](N)COC(=O)NC45CC6CC(C)(CC(C)(C6)C4)C5)C3)c(OC)c2)cc1OC] |
| A24 | 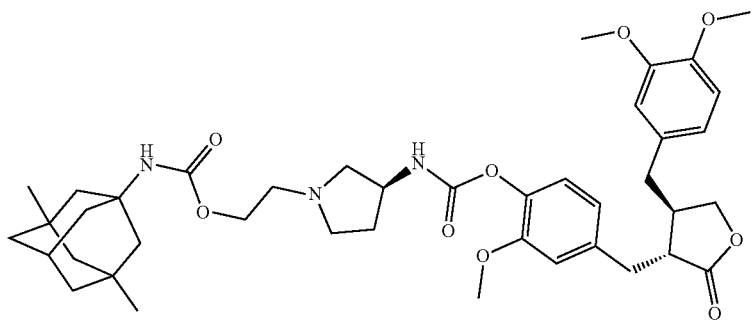 [SMILES: COc1ccc(C[C@H]2COC(=O)[C@@H]2Cc2ccc(OC(=O)N[C@H]3CCN(CCOC(=O)NC45CC6CC(C)(CC(C)(C6)C4)C5)C3)c(OC)c2)cc1OC] |
| A25 | 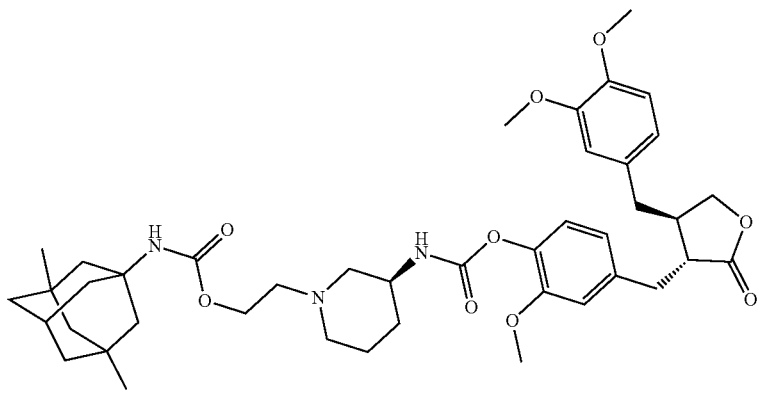 [SMILES: COc1ccc(C[C@H]2COC(=O)[C@@H]2Cc2ccc(OC(=O)N[C@H]3CCCN(CCOC(=O)NC45CC6CC(C)(CC(C)(C6)C4)C5)C3)c(OC)c2)cc1OC] |
| A26 | 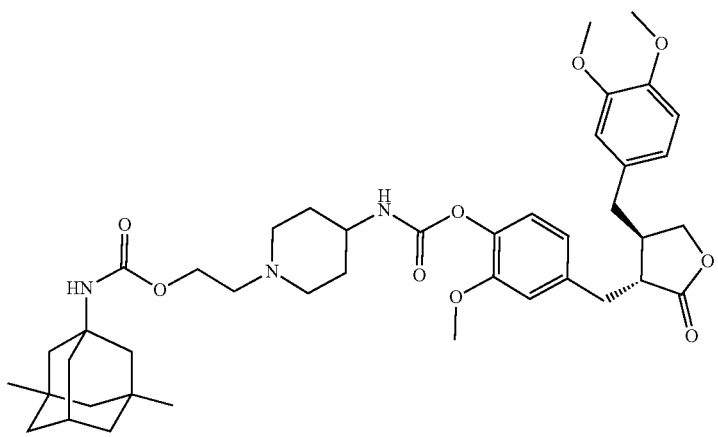 [SMILES: COc1ccc(C[C@H]2COC(=O)[C@@H]2Cc2ccc(OC(=O)NC3CCN(CCOC(=O)NC45CC6CC(C)(CC(C)(C6)C4)C5)CC3)c(OC)c2)cc1OC] |

| No. | Conjugate Structure |
|---|---|
| A27 | 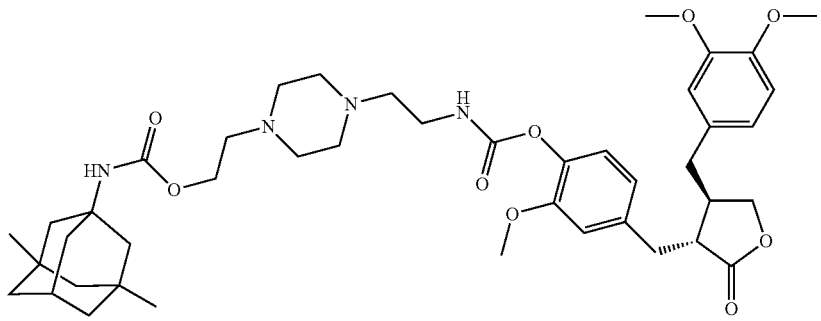 [SMILES: COc1ccc(C[C@H]2COC(=O)[C@@H]2Cc2ccc(OC(=O)NCCN3CCN(CCOC(=O)NC45CC6CC(C)(CC(C)(C6)C4)C5)CC3)c(OC)c2)cc1OC] |
| A28 | 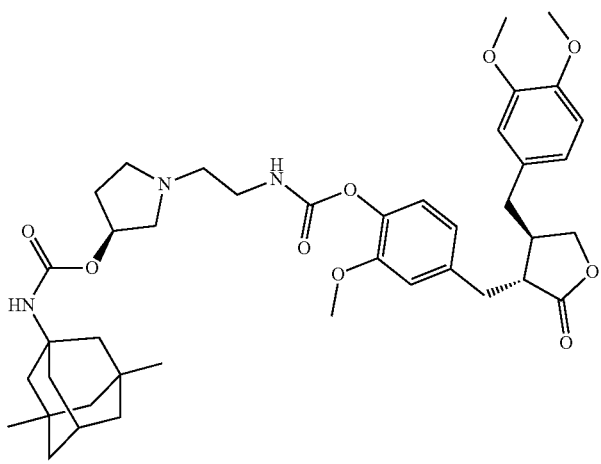 [SMILES: COc1ccc(C[C@H]2COC(=O)[C@@H]2Cc2ccc(OC(=O)NCCN3CC[C@H](OC(=O)NC45CC6CC(C)(CC(C)(C6)C4)C5)C3)c(OC)c2)cc1OC] |
| A29 | 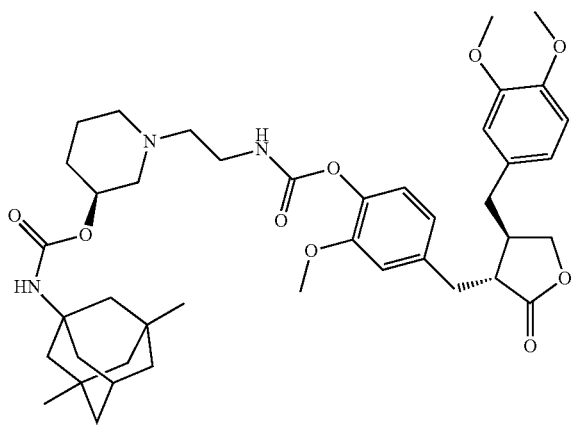 [SMILES: COc1ccc(C[C@H]2COC(=O)[C@@H]2Cc2ccc(OC(=O)NCCN3CCC[C@H](OC(=O)NC45CC6CC(C)(CC(C)(C6)C4)C5)C3)c(OC)c2)cc1OC] |
| A30 | 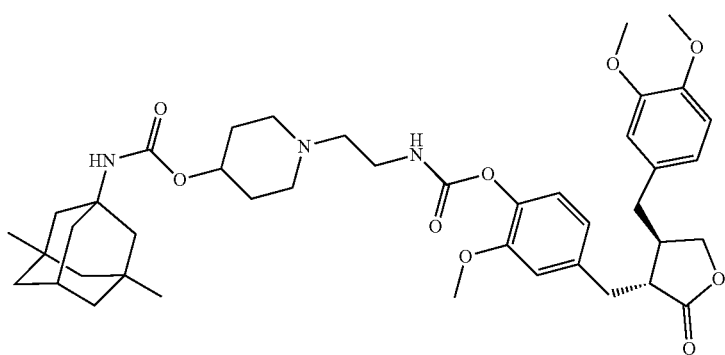 [SMILES: COc1ccc(C[C@H]2COC(=O)[C@@H]2Cc2ccc(OC(=O)NCCN3CCC(OC(=O)NC45CC6CC(C)(CC(C)(C6)C4)C5)CC3)c(OC)c2)cc1OC] |

| No. | Conjugate Structure |
|---|---|
| A31 | 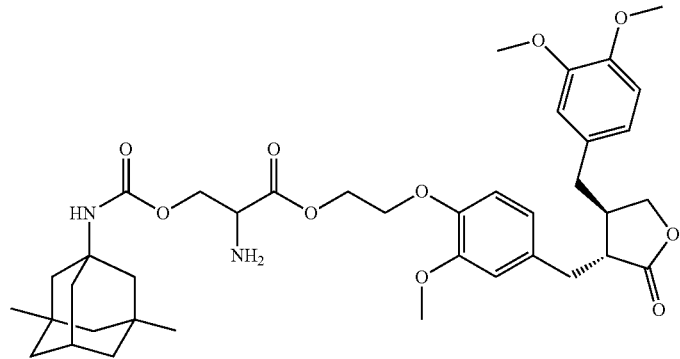 [SMILES: COc1ccc(C[C@H]2COC(=O)[C@@H]2Cc2ccc(OCCOC(=O)C(N)COC(=O)NC34CC5CC(C)(CC(C)(C5)C3)C4)c(OC)c2)cc1OC] |
| A32 | 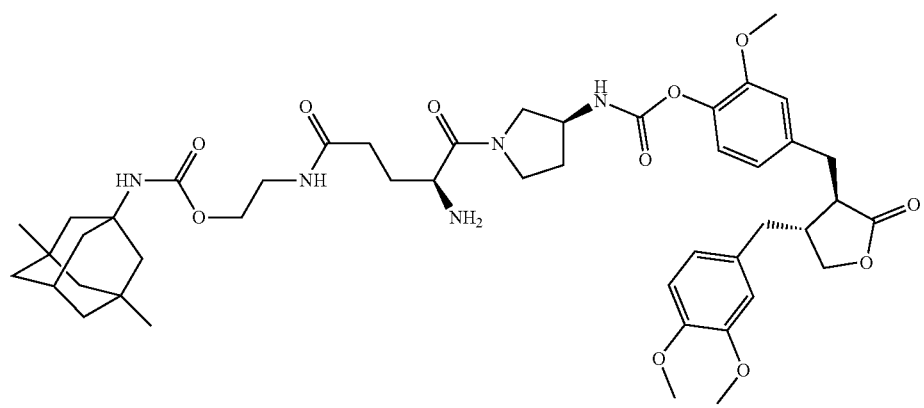 [SMILES: COc1ccc(C[C@H]2COC(=O)[C@@H]2Cc2ccc(OC(=O)N[C@H]3CCN(C(=O)[C@@H](N)CCC(=O)NCCOC(=O)NC45CC6CC(C)(CC(C)(C6)C4)C5)C3)c(OC)c2)cc1OC] |
| A33 | 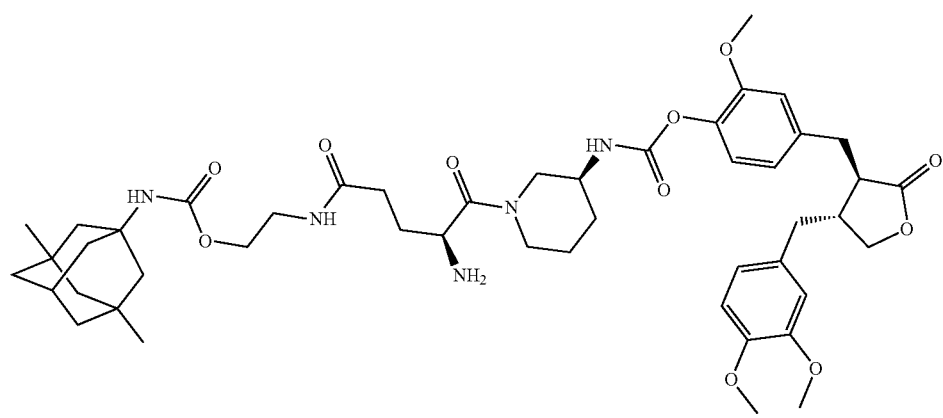 [SMILES: COc1ccc(C[C@H]2COC(=O)[C@@H]2Cc2ccc(OC(=O)N[C@H]3CCCN(C(=O)[C@@H](N)CCC(=O)NCCOC(=O)NC45CC6CC(C)(CC(C)(C6)C4)C5)C3)c(OC)c2)cc1OC] |
| A34 | 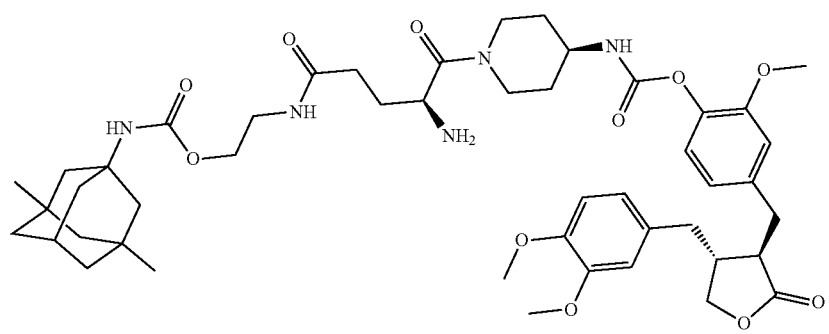 |

| No. | Conjugate Structure |
|---|---|
| A35 | 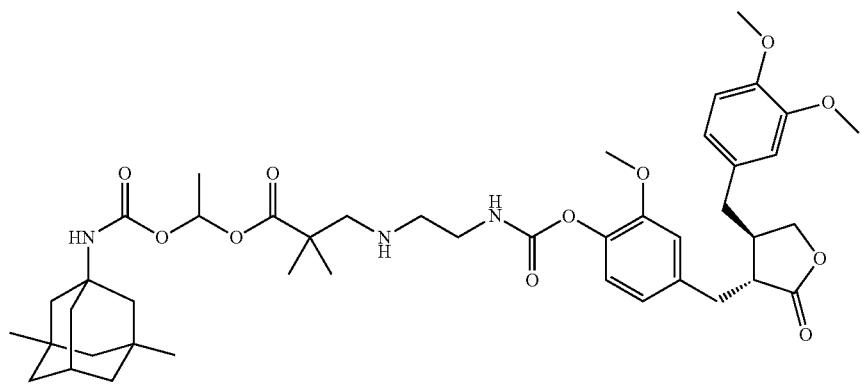 |
| A36 | 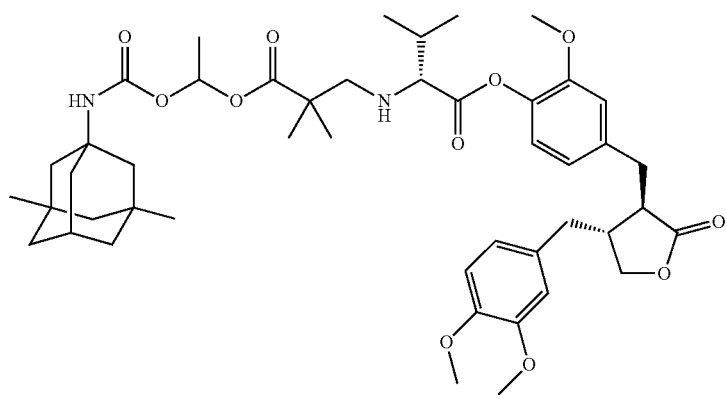 [SMILES: COc1ccc(C[C@H]2COC(=O)[C@@H]2Cc2ccc(OC(=O)[C@H](NCC(C)(C)C(=O)OC(C)OC(=O)NC34CC5CC(C)(CC(C)(C5)C3)C4)C(C)C)c(OC)c2)cc1OC] |
| A37 | 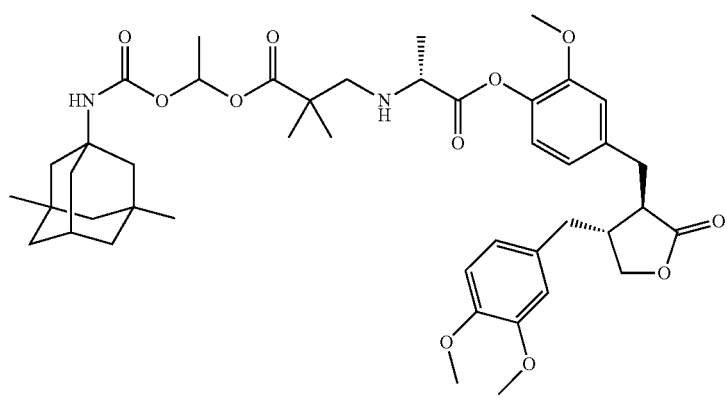 [SMILES: COc1ccc(C[C@H]2COC(=O)[C@@H]2Cc2ccc(OC(=O)[C@@H](C)NCC(C)(C)C(=O)OC(C)OC(=O)NC34CC5CC(C)(CC(C)(C5)C3)C4)c(OC)c2)cc1OC] |
| A38 | 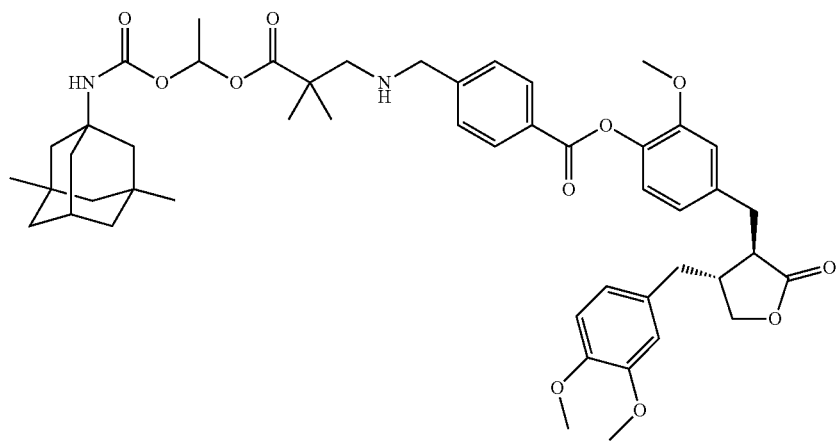 [SMILES: COc1ccc(C[C@H]2COC(=O)[C@@H]2Cc2ccc(OC(=O)c3ccc(CNCC(C)(C)C(=O)OC(C)OC(=O)NC45CC6CC(C)(CC(C)(C6)C4)C5)cc3)c(OC)c2)cc1OC] |

| No. | Conjugate Structure |
|---|---|
| A39 | 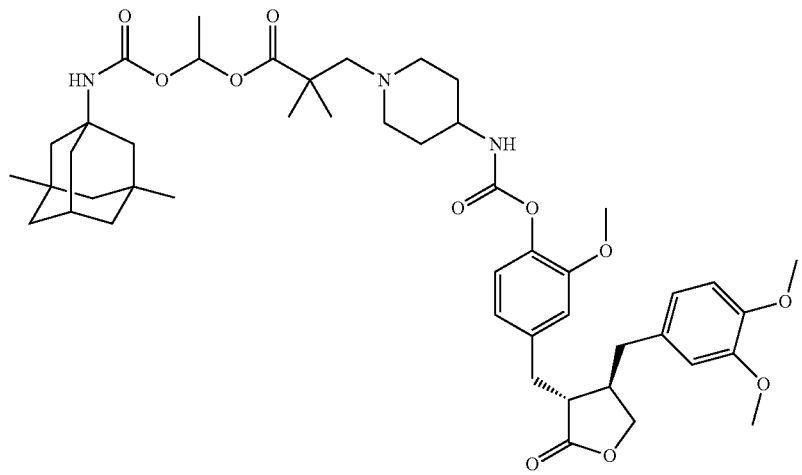 |
| A40 | 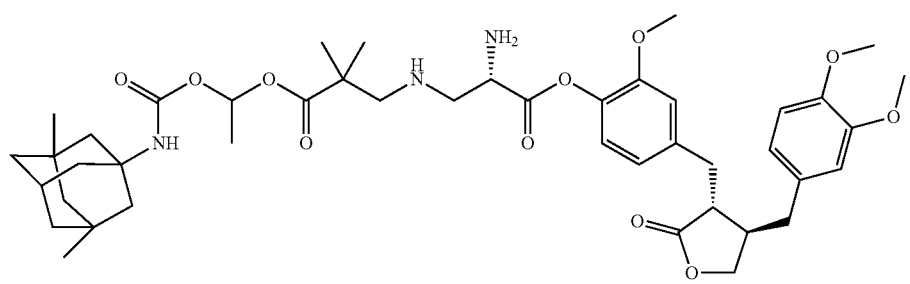 [SMILES: COc1ccc(C[C@H]2COC(=O)[C@@H]2Cc2ccc(OC(=O)[C@@H](N)CNCC(C)(C)C(=O)OC(C)OC(=O)NC34CC5CC(C)(CC(C)(C5)C3)C4)c(OC)c2)cc1OC] |
| A41 | 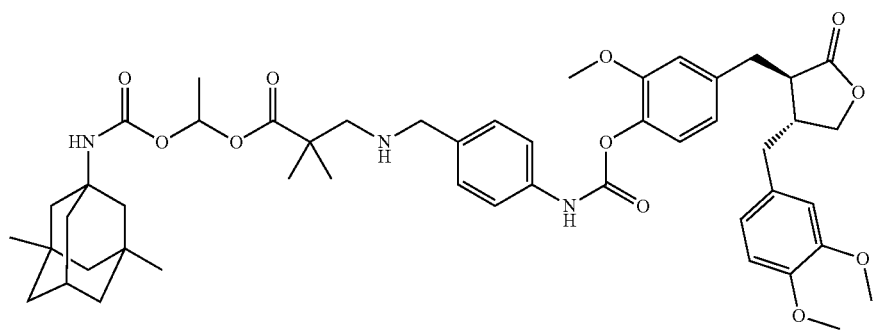 |
| A42 | 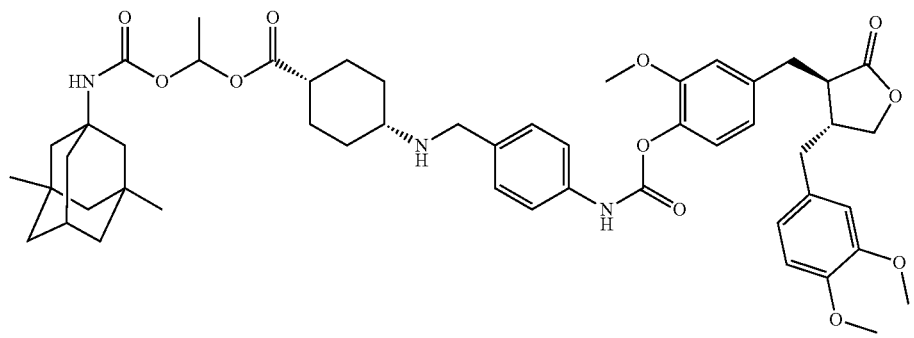 |

| No. | Conjugate Structure |
|---|---|
| A43 | 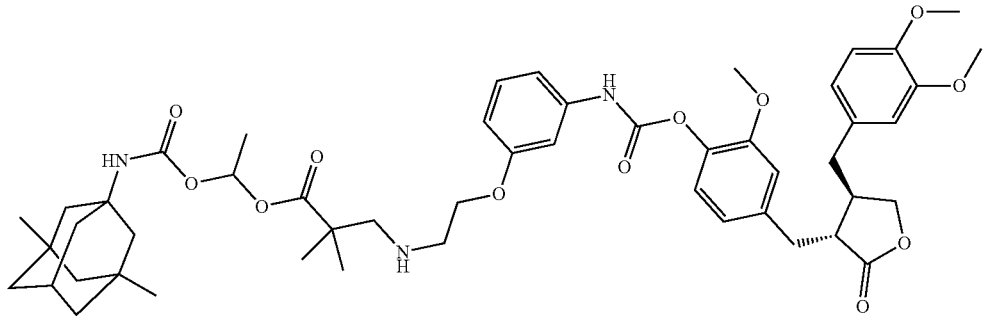 [SMILES: COc1ccc(C[C@H]2COC(=O)[C@@H]2Cc2ccc(OC(=O)Nc3cccc(OCCNCC(C)(C)C(=O)OC(C)OC(=O)NC45CC6CC(C)(CC(C)(C6)C4)C5)c3)c(OC)c2)cc1OC] |
| A44 | 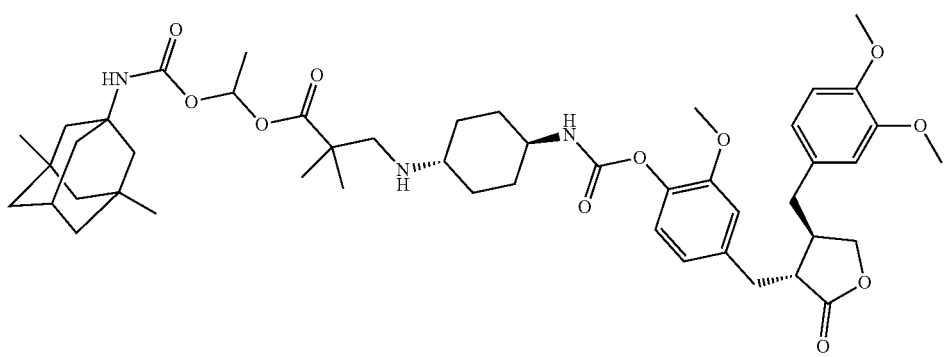 [SMILES: COc1ccc(C[C@H]2COC(=O)[C@@H]2Cc2ccc(OC(=O)N[C@H]3CC[C@H](NCC(C)(C)C(=O)OC(C)OC(=O)NC45CC6CC(C)(CC(C)(C6)C4)C5)CC3)c(OC)c2)cc1OC] |
| A45 | 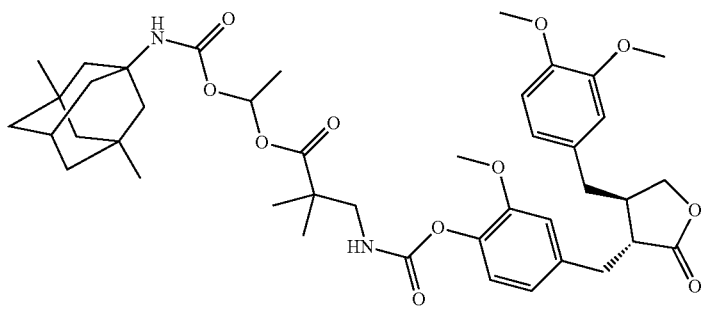 [SMILES: COc1ccc(C[C@H]2COC(=O)[C@@H]2Cc2ccc(OC(=O)NCC(C)(C)C(=O)OC(C)OC(=O)NC34CC5CC(C)(CC(C)(C5)C3)C4)c(OC)c2)cc1OC] |
| A46 | 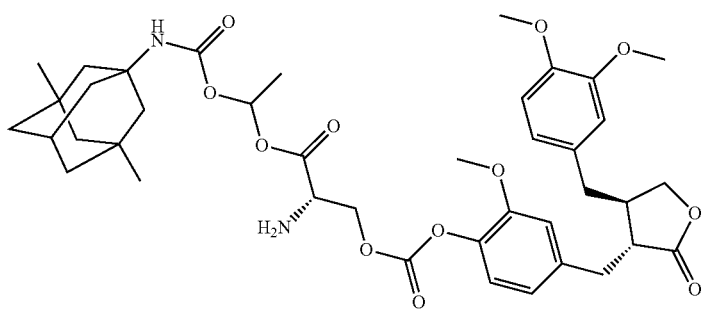 [SMILES: COc1ccc(C[C@H]2COC(=O)[C@@H]2Cc2ccc(OC(=O)OC[C@H](N)C(=O)OC(C)OC(=O)NC34CC5CC(C)(CC(C)(C5)C3)C4)c(OC)c2)cc1OC] |

| No. | Conjugate Structure |
|---|---|
| A47 | 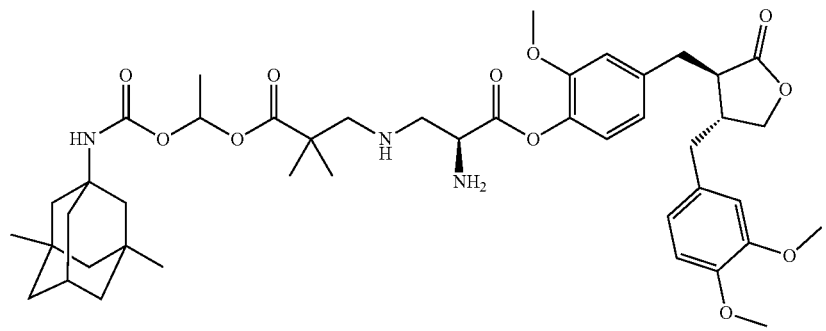 |
| A48 | 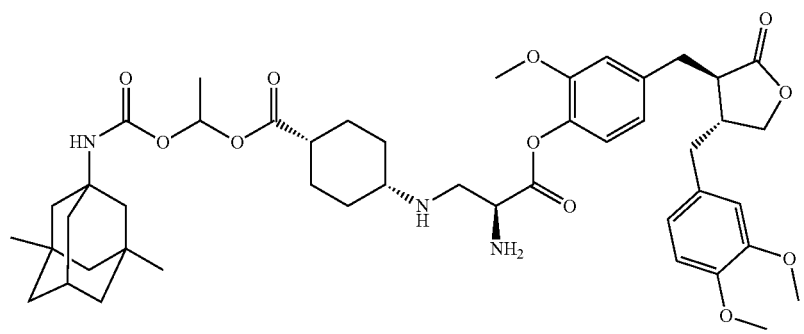 |
| A49 | 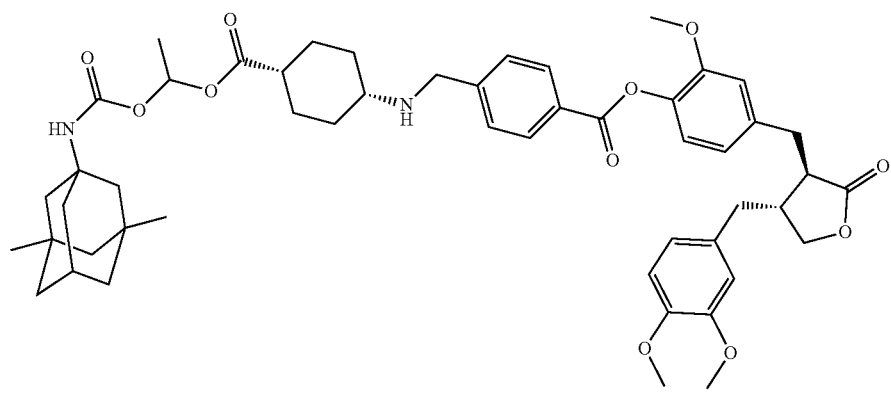 [SMILES: COc1ccc(C[C@H]2COC(=O)[C@@H]2Cc2ccc(OC(=O)c3ccc(CN[C@H]4CC[C@@H](C(=O)OC(C)OC(=O)NC56CC7CC(C)(CC(C)(C7)C5)C6)CC4)cc3)c(OC)c2)cc1OC] |
| A50 | 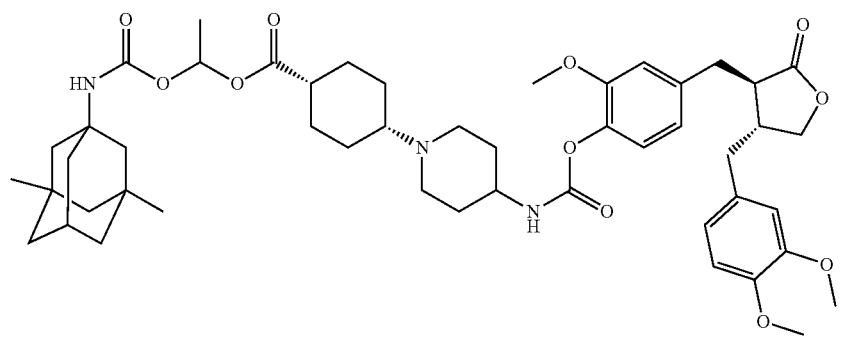 |

| No. | Conjugate Structure |
|---|---|
| A51 | 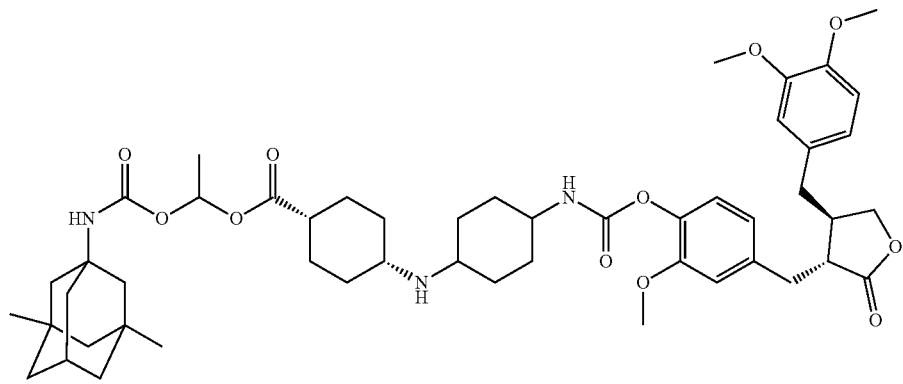 [SMILES: COc1ccc(C[C@H]2COC(=O)[C@@H]2Cc2ccc(OC(=O)NC3CCC(N[C@H]4CC[C@@H](C(=O)OC(C)OC(=O)NC56CC7CC(C)(CC(C)(C7)C5)C6)CC4)CC3)c(OC)c2)cc1OC] |
| A52 | 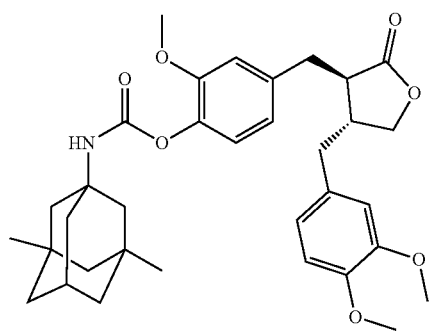 |
| A53 | 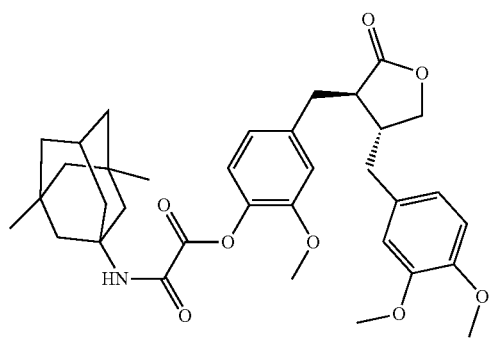 [SMILES: COc1ccc(C[C@H]2COC(=O)[C@@H]2Cc2ccc(OC(=O)C(=O)NC34CC5CC(C)(CC(C)(C5)C3)C4)c(OC)c2)cc1OC] |
| A54 | 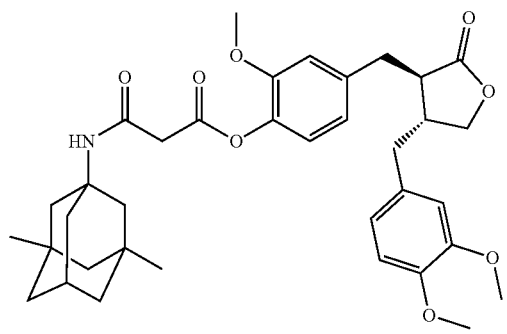 |

| No. | Conjugate Structure |
|---|---|
| A55 | 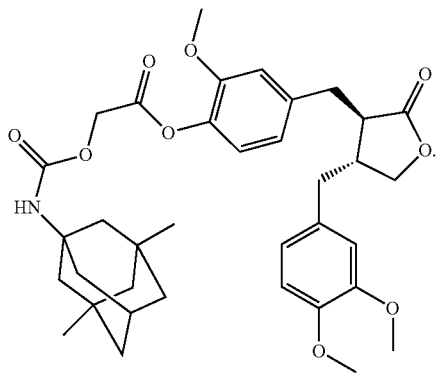 [SMILES: COc1ccc(C[C@H]2COC(=O)[C@@H]2Cc2ccc(OC(=O)COC(=O)NC34CC5CC(C)(CC(C)(C5)C3)C4)c(OC)c2)cc1OC] |

5. A pharmaceutical composition comprising the conjugate according to claim 1 and one or more pharmaceutically acceptable carriers.

6. The pharmaceutical composition according to claim 5, further comprising one or more additional agents for the treatment of a disease associated with the Aβ or Tau protein pathway.

7. A method for treating a disease associated with the Aβ or Tau protein pathway, comprising administering to a subject in need thereof a therapeutically effective amount of the conjugate according to claim 1, wherein the disease is a neurodegenerative disease.

8. The method according to claim 7, wherein the disease is Alzheimer's disease or Parkinson's disease.

9. The method according to claim 7, further comprising administering to a subject in need thereof an additional agent for the treatment of a disease associated with the Aβ or Tau protein pathway.

10. The pharmaceutical composition according to claim 6, wherein the additional agent for the treatment of a disease associated with the Aβ or Tau protein pathway is an acetylcholinesterase inhibitor.

11. The pharmaceutical composition according to claim 10, wherein the acetylcholinesterase inhibitor is donepezil, huperzine A, or tacrine.

12. A method for treating a disease associated with the Aβ or Tau protein pathway, comprising administering to a subject in need thereof a therapeutically effective amount of the pharmaceutical composition according to claim 5, wherein the disease is a neurodegenerative disease.

13. The method according to claim 9, wherein the additional agent for the treatment of a disease associated with the Aβ or Tau protein pathway is an acetylcholinesterase inhibitor.

14. The method according to claim 13, wherein the acetylcholinesterase inhibitor is donepezil, huperzine A, or tacrine.

* * * * *